(12) United States Patent
Ashcraft et al.

(10) Patent No.: US 9,133,123 B2
(45) Date of Patent: Sep. 15, 2015

(54) CERTAIN AMINO-PYRIDINES AND AMINO-TRIAZINES, COMPOSITIONS THEREOF, AND METHODS FOR THEIR USE

(75) Inventors: Luke W. Ashcraft, San Francisco, CA (US); Gustave Bergnes, Pacifica, CA (US); Scott Collibee, San Carlos, CA (US); Chihyuan Chuang, Millbrae, CA (US); Jeff Gardina, South San Francisco, CA (US); Bradley P. Morgan, Moraga, CA (US); Alex R. Muci, San Francisco, CA (US); Xiangping Qian, Foster City, CA (US); Antonio Romero, San Mateo, CA (US); Jeffrey Warrington, San Mateo, CA (US); Zhe Yang, Daly City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 158 days.

(21) Appl. No.: 13/642,227

(22) PCT Filed: Apr. 22, 2011

(86) PCT No.: PCT/US2011/033650
§ 371 (c)(1),
(2), (4) Date: Mar. 1, 2013

(87) PCT Pub. No.: WO2011/133920
PCT Pub. Date: Oct. 27, 2011

(65) Prior Publication Data
US 2013/0150368 A1 Jun. 13, 2013

Related U.S. Application Data

(60) Provisional application No. 61/327,597, filed on Apr. 23, 2010, provisional application No. 61/327,538, filed on Apr. 23, 2010, provisional application No. 61/412,299, filed on Nov. 10, 2010, provisional application No. 61/412,302, filed on Nov. 10, 2010.

(51) Int. Cl.
| | |
|---|---|
| C07D 253/07 | (2006.01) |
| C07D 401/12 | (2006.01) |
| C07D 401/14 | (2006.01) |
| C07D 417/14 | (2006.01) |
| A61K 31/53 | (2006.01) |
| A61K 31/427 | (2006.01) |
| A61K 31/4427 | (2006.01) |
| A61P 21/00 | (2006.01) |
| A61P 21/04 | (2006.01) |
| C07D 213/75 | (2006.01) |
| C07D 213/78 | (2006.01) |
| C07D 213/82 | (2006.01) |
| C07D 215/48 | (2006.01) |
| C07D 403/04 | (2006.01) |

(Continued)

(52) U.S. Cl.
CPC ............ *C07D 213/74* (2013.01); *C07D 213/75* (2013.01); *C07D 213/78* (2013.01); *C07D 213/82* (2013.01); *C07D 215/38* (2013.01); *C07D 215/48* (2013.01); *C07D 253/07* (2013.01); *C07D 401/12* (2013.01); *C07D 401/14* (2013.01); *C07D 403/04* (2013.01); *C07D 403/10* (2013.01); *C07D 417/04* (2013.01); *C07D 417/14* (2013.01)

(58) Field of Classification Search
CPC .. C07D 253/07; C07D 401/12; C07D 401/14; C07D 417/14; A61K 31/53; A61K 31/427; A61K 31/4427
USPC .......................................... 544/182; 514/242
See application file for complete search history.

(56) References Cited

U.S. PATENT DOCUMENTS

| 4,157,392 A | 6/1979 | Gullo et al. |
| 4,169,158 A | 9/1979 | Laborit |

(Continued)

FOREIGN PATENT DOCUMENTS

| CA | 2 757 188 | 10/2010 |
| EP | 0 429 344 | 5/1991 |

(Continued)

OTHER PUBLICATIONS

Bond et al. Future Med Chem. Jan. 2013; 5(1): 41-52.*

(Continued)

*Primary Examiner* — Venkataraman Balasubramanian

(57) ABSTRACT

Provided are compounds of Formula I:

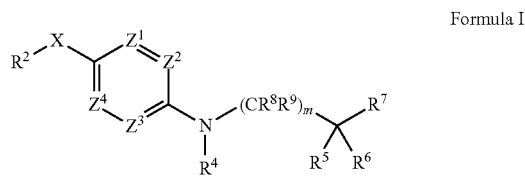

Formula I or a pharmaceutically acceptable salt thereof, wherein $R^2$, $R^4$, $R^5$, $R^6$, $R^7$, $R^8$, $R^9$, X, $Z^1$, $Z^2$, $Z^3$, $Z^4$ and m are as defined herein.

Also provided is a pharmaceutically acceptable composition comprising a compound of Formula I, or a pharmaceutically acceptable salt thereof.

Also provided are methods of using a compound of Formula I, or a pharmaceutically acceptable salt thereof.

45 Claims, No Drawings

(51) Int. Cl.
  *C07D 417/04* (2006.01)
  *C07D 213/74* (2006.01)
  *C07D 215/38* (2006.01)
  *C07D 403/10* (2006.01)

(56) References Cited

U.S. PATENT DOCUMENTS

| | | | |
|---|---|---|---|
| 4,251,658 | A | 2/1981 | Szilagyi et al. |
| 4,514,397 | A | 4/1985 | Wermuth et al. |
| 5,461,053 | A | 10/1995 | Boigegrain et al. |
| 6,297,375 | B1 | 10/2001 | Boes et al. |
| 6,780,869 | B1 | 8/2004 | Green et al. |
| 7,157,455 | B2 | 1/2007 | Bartkovitz et al. |
| 7,507,737 | B2 | 3/2009 | Edwards |
| 7,652,009 | B2 | 1/2010 | Kim et al. |
| 2003/0195221 | A1 | 10/2003 | Cai et al. |
| 2005/0187266 | A1 | 8/2005 | Su et al. |
| 2007/0173465 | A9 | 7/2007 | Monahan et al. |
| 2007/0197505 | A1 | 8/2007 | Morgan et al. |
| 2007/0197507 | A1 | 8/2007 | Morgan et al. |
| 2008/0004257 | A1* | 1/2008 | Chan et al. ............ 514/218 |
| 2008/0318899 | A1 | 12/2008 | Watterson et al. |
| 2009/0029345 | A1 | 1/2009 | Russell et al. |
| 2009/0143385 | A1 | 6/2009 | Buettelmann et al. |
| 2009/0264433 | A1 | 10/2009 | Russell et al. |
| 2009/0270398 | A1 | 10/2009 | Russell et al. |
| 2010/0029942 | A1 | 2/2010 | Cesco-Cancian |
| 2014/0206709 | A1 | 7/2014 | Yang et al. |

FOREIGN PATENT DOCUMENTS

| | | |
|---|---|---|
| EP | 1 078 632 | 2/2001 |
| EP | 2 017 261 | 1/2009 |
| WO | WO 03/044021 | 5/2003 |
| WO | WO 2005/030140 | 4/2005 |
| WO | WO 2006/066172 | 6/2006 |
| WO | WO 2006/050389 | 11/2006 |
| WO | WO 2007/003604 | 1/2007 |
| WO | WO 2007/048802 | 5/2007 |
| WO | WO 2007/075377 | 7/2007 |
| WO | WO-2007/075377 A2 | 7/2007 |
| WO | WO 2007/089336 | 8/2007 |
| WO | WO 2007/130383 | 11/2007 |
| WO | WO 2008/071646 | 6/2008 |
| WO | WO 2009/152168 | 12/2009 |
| WO | WO 2010/022121 | 2/2010 |
| WO | WO-2011/133882 A1 | 10/2011 |
| WO | WO-2011/133888 A1 | 10/2011 |
| WO | WO 2013/151938 | 10/2013 |
| WO | WO/2013/155262 | 10/2013 |

OTHER PUBLICATIONS

Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
U.S. Appl. No. 13/642,206, filed Apr. 22, 2011, Yang et al.
U.S. Appl. No. 13/642,207, filed Apr. 22, 2011, Ashcraft et al.
Allingham et al., "The structural basis of blebbistatin inhibition and specificity for myoson II." Nature Structural & Molecular Biology 12:4, pp. 378-379 (Apr. 2005).
International Search Report & Written Opinion in PCT/US2011/033605 (Jul. 6, 2011).
International Search Report & Written Opinion in PCT/US2011/033614 (Jun. 28, 2011).
Refaat et al. Bulletin of the Faculty of Pharmacy (Cairo University), 42(2), 2004, 415-423.
Bressi et al., "Adenosine Analogues as Inhibitors of *Trypanosoma brucei* Phosphoglycerate Kinase: Elucidation of a Novel Binding Mode for a 2-Amino-N6-Substituted Adenosine" J. Med. Chem. 43:4135-4150 (2000).
Contreras et al., "Aminopyridazines acetylcholinesterase inhibitors" J. Med. Chem. 42:730-741 (1999).
Cote et al., "Substituted aminopyridines as potent and selective phosphodiesterase-4 inhibitors" Bioorganic & Medicinal Chemistry Letters, 13:741-744 (2003).
Database PubChem Compound [Online] NCBI; (Jul. 31, 2006), XP002713427, Database accession No. CID9195699.
Dimauro et al., "Structure-Guided Design of Aminopyrimidine Amides as Potent, Selective Inhibitors of Lymphocyte Specific Kinase: Synthesis, Structure-Activity Relationships, and Inhibition of in Vivo T Cell Activation", J. Med. Chem. 51:1681-1694 (2008).
Hamby et al., "Structure-Activity Relationships for a Novel Series of Pyrid0[2,3-D]Pyrimidine Tyrosine Kinase Inhibitors" J. Med. Chem. 40:2296-2303 (1997).
Hiatt, WR et al. 'Efficacy and Tolerability of the Novel Fast Skeletal Muscle Troponin Activator, CK-2017357, in Patients with Claudication.' 22nd Annual Sessions of the Society for Vascular Medicine, Boston, MA, Jun. 2011 (poster presentation); [Retrieved on Aug. 20, 2013). Retrieved from the Internet at <URL: www.cytokinetics.com/pdf/4022-20110531-rev004.pdf>.
International Search Report & Written Opinion in PCT/US2013/036114 (Nov. 5, 2013).
International Search Report & Written Opinion in PCT/US2013/034824 (Jun. 13, 2013).
Ishida et al. "Novel and orally active 5-(1,3,4-oxadiazol-2-yl)pyrimidine derivatives as selective FLT3 inhibitors" Bioorganic & Medicinal Chemistry Letters, 18:5472-5477 (2008).
March et al. "Antimalarials 3 l,2,4-Triazines" J. Med. Chem. 19:845-848 (1976).
Martyn et al., "Synthesis and antiplasmodial activity of novel 2,4-diaminopyrimidine" Bioorganic & Medicinal Chemistry Letters, 20: 228-231 (2010).
Okumura et al., "Synthesis of Isokinetin, 2-N-furfurylaminopurine and its Leaf-growth Activity (Studies of Isokinetin and its Analogs. Part I)" Bulletin of the Chemical Society of Japan, 33:1471-1472 (1960).
PCT/US2011/033650. International Search Report & Written Opinion (Jun. 23, 2011).
Russell et al., "Activation of Fast Skeletal Muscle Troponin as a Potential Therapeutic Approach for Treating Neuromuscular Diseases", *Nature Medicine*, 2012;18:3:452-455.
Hwee et al., "Fast Skeletal Muscle Troponin Activator Tirasemtiv Increases Muscle Function and Performance in the B6SJL-SOD1G93A ALS Mouse Model", *PLOS One*, May 7, 2014.
Hwee et al., "Fast Skeletal Muscle Troponin Activator Tirasemtiv Increases Muscle Function and Performance in Mouse Models of Spinal Muscular Atrophy", 25th International Symposium on ALS/MND, Brussels, Belgium, Dec. 2014.
Hinken et al., "A Novel Fast Skeletal Muscle Activator, CK-2017357, Improves Muscle Function in a Rodent Model of Myasthenia Gravis", 2011 Experimental Biology Conference, Washington, DC. Apr. 2011.
A Study to Evaluate the Effects of Multiple Doses of CK-2017357 in Patients With Amyotrophic Lateral Sclerosis (ALS) (https://www.clinicaltrials.gov/ct2/show/NCT01378676?term=tirasemtiv&rank=2, Jun. 20, 2011.
Pharmacodynamic Study of CK-2017357 in Patients With Generalized Myasthenia Gravis (https://www.clinicaltrials.gov/ct2/show/NCT01268280?term=tirasemtiv&rank=3, Dec. 28, 2010.
A Study of CK-2017357 in Patients With Peripheral Artery Disease and Symptomatic Claudication (https://www.clinicaltrials.gov/ct2/show/NCT01131013?term=tirasemtiv&rank=1), May 25, 2010.

* cited by examiner

CERTAIN AMINO-PYRIDINES AND AMINO-TRIAZINES, COMPOSITIONS THEREOF, AND METHODS FOR THEIR USE

This application is a 35 USC 371 National Stage Entry of PCT/US2011/033650 filed Apr. 22, 2011, and claims the benefit of U.S. Provisional Application Nos. 61/327,538, filed Apr. 23, 2010, 61/327,597, filed Apr. 23, 2010, 61/412,299, filed Nov. 10, 2010, and 61/412,302 filed Nov. 10, 2010, each of which is incorporated by reference in its entirety for all purposes.

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II forms homo-dimers resulting in two globular head domains linked together by a long alpha-helical coiled-coiled tail to form the core of the sarcomere's thick filament. The globular heads have a catalytic domain where the actin binding and ATPase functions of myosin take place. Once bound to an actin filament, the release of phosphate (cf. ADP-Pi to ADP) signals a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament ($Ca^{2+}$ regulated) coupled with return of the catalytic domain and light chain to their starting conformation/orientation completes the catalytic cycle, responsible for intracellular movement and muscle contraction.

Tropomyosin and troponin mediate the calcium effect on the interaction on actin and myosin. The troponin complex is comprised of three polypeptide chains: troponin C, which binds calcium ions; troponin I, which binds to actin; and troponin T, which binds to tropomyosin. The skeletal troponin-tropomyosin complex regulates the myosin binding sites extending over several actin units at once.

Troponin, a complex of the three polypeptides described above, is an accessory protein that is closely associated with actin filaments in vertebrate muscle. The troponin complex acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin inhibits the interaction of actin and myosin. Skeletal troponin C is capable of binding up to four calcium molecules. Studies suggest that when the level of calcium in the muscle is raised, troponin C exposes a binding site for troponin I, recruiting it away from actin. This causes the tropomyosin molecule to shift its position as well, thereby exposing the myosin binding sites on actin and stimulating myosin ATPase activity.

Human skeletal muscle is composed of different types of contractile fibers, classified by their myosin type and termed either slow or fast fibers. Table 1 summarizes the different proteins that make up these types of muscle.

TABLE 1

| | Muscle Fiber Type | |
|---|---|---|
| | Fast skeletal | Slow Skeletal |
| Myosin Heavy Chain | IIa, (IIb*), IIx/d | Cardiac β |
| Troponin I (TnI) | TnI fast SK | TnI slow SK |
| Troponin T (TnT) | TnT fast SK | TnT slow SK |
| Troponin C (TnC) | TnC fast SK | TnC slow/cardiac |
| Tropomyosin | TM-β/TM-α/TPM 3 | TM-β/TM-αs |

*MHC IIb is not expressed in human muscle but is present in rodents and other mammals.

In healthy humans most skeletal muscles are composed of both fast and slow fibers, although the proportions of each vary with muscle type. Slow skeletal fibers, often called type I fibers, have more structural similarity with cardiac muscle and tend to be used more for fine and postural control. They usually have a greater oxidative capacity and are more resistant to fatigue with continued use. Fast skeletal muscle fibers, often called type II fibers, are classified into fast oxidative (IIa) and fast glycolytic (type IIx/d) fibers. While these muscle fibers have different myosin types, they share many components including the troponin and tropomyosin regulatory proteins. Fast skeletal muscle fibers tend to exert greater force but fatigue faster than slow skeletal muscle fibers and are functionally useful for acute, large scale movements such as rising from a chair or correcting falls.

Muscle contraction and force generation is controlled through nervous stimulation by innervating motor neurons. Each motor neuron may innervate many (approximately 100-380) muscle fibers as a contractile whole, termed a motor unit. When a muscle is required to contract, motor neurons send stimuli as nerve impulses (action potentials) from the brain stem or spinal cord to each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh). ACh triggers a second action potential in the muscle that spreads rapidly along the fiber and into invaginations in the membrane, termed t-tubules. T-tubules are physically connected to Ca2+ stores within the sarcoplasmic reticulum (SR) of muscle via the dihydropyridine receptor (DHPR). Stimulation of the DHPR activates a second Ca2+ channel in the SR, the ryanodine receptor, to trigger the release of Ca2+ from stores in the SR to the muscle cytoplasm where it can interact with the troponin complex to initiate muscle contraction. If muscle stimulation stops, calcium is rapidly taken back up into the SR through the ATP dependent Ca2+ pump, SERCA.

Muscle function can become compromised in disease by many mechanisms. Examples include the frailty associated with old age (termed sarcopenia) and cachexia syndromes associated with diseases such as cancer, heart failure, chronic obstructive pulmonary disease (COPD), and chronic kidney disease/dialysis. Severe muscular dysfunction can arise from neuromuscular diseases (such as Amyotrophic Lateral Sclerosis (ALS), spinal muscular atrophy (SMA) and myasthenia gravis) or muscular myopathies (such as muscular dystrophies). Additionally, muscle function may become compromised due to rehabilitation-related deficits, such as those associated with recovery from surgery (e.g. post-surgical muscle weakness), prolonged bed rest, or stroke rehabilitation. Additional examples of diseases or conditions where muscle function becomes compromised include peripheral vascular disease (e.g., claudication), chronic fatigue syndrome, metabolic syndrome, and obesity.

Accordingly, there is a need for the development of new compounds that modulate skeletal muscle contractility. There remains a need for agents that exploit new mechanisms of action and which may have better outcomes in terms of relief of symptoms, safety, and patient mortality, both short-term and long-term and an improved therapeutic index.

Provided is a compound of Formula I:

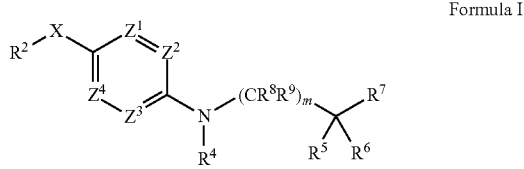

Formula I or a pharmaceutically acceptable salt thereof, wherein $R^2$, $R^4$, $R^5$, $R^6$, $R^7$, $R^8$, $R^9$, X, $Z^1$, $Z^2$, $Z^3$, $Z^4$ and m are as defined herein.

Also provided is a pharmaceutically acceptable composition comprising a compound of Formula I, or a pharmaceutically acceptable salt thereof.

Also provided are methods for treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof.

As used in the present specification, the following words and phrases are generally intended to have the meanings as set forth below, except to the extent that the context in which they are used indicates otherwise.

Throughout this application, unless the context indicates otherwise, references to a compound of Formula I includes all subgroups of Formula I defined herein, including all substructures, subgenera, preferences, embodiments, examples and particular compounds defined and/or described herein.

References to a compound of Formula I and subgroups thereof include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. "Crystalline form," "polymorph," and "novel form" may be used interchangeably herein, and are meant to include all crystalline and amorphous forms of the compound, including, for example, polymorphs, pseudopolymorphs, solvates (including hydrates), co-crystals, unsolvated polymorphs (including anhydrates), conformational polymorphs, and amorphous forms, as well as mixtures thereof, unless a particular crystalline or amorphous form is referred to. In some embodiments, references to a compound of Formula I and subgroups thereof include polymorphs, solvates, co-crystals, isomers, tautomers and/or oxides thereof. In some embodiments, references to a compound of Formula I and subgroups thereof include polymorphs, solvates, and/or co-crystals thereof. In some embodiments, references to a compound of Formula I and subgroups thereof include isomers, tautomers and/or oxides thereof. In some embodiments, references to a compound of Formula I and subgroups thereof include solvates thereof. Similarly, the term "salts" includes solvates of salts of compounds.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl. "Lower alkyl" refers to alkyl groups having 1 to 6 carbons.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Alkenyl" refers to an unsaturated branched or straight-chain alkyl group having the indicated number of carbon atoms (e.g., 2 to 8, or 2 to 6 carbon atoms) and at least one carbon-carbon double bond derived by the removal of one molecule of hydrogen from adjacent carbon atoms of the corresponding alkyl. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl). "Lower alkenyl" refers to alkenyl groups having 2 to 6 carbons.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Aralkyl" refers to a residue having the indicated number of carbon atoms (e.g., 7 to 12 or 7 to 10 carbon atoms) in which an aryl moiety is attached to the parent structure via an alkyl residue. The alkyl residue may be straight-chain or branched. Examples include benzyl, phenethyl and 1-phenylethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5- b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

"Isomers" are different compounds that have the same molecular formula. "Stereoisomers" are isomers that differ only in the way the atoms are arranged in space. "Enantiomers" are stereoisomers that are non-superimposable mirror images of each other. A 1:1 mixture of a pair of enantiomers is a "racemic" mixture. The symbol "(±)" may be used to designate a racemic mixture where appropriate. "Diastereoisomers" are stereoisomers that have at least two asymmetric atoms, but which are not mirror-images of each other. A "meso compound" or "meso isomer" is a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds disclosed and/or described herein contain one or more asymmetric centers and can thus give rise to enantiomers, diastereomers, meso isomers and other stereoisomeric forms. Unless otherwise indicated, compounds disclosed and/or described herein include all such possible enantiomers, diastereomers, meso isomers and other stereoisomeric forms, including racemic mixtures, optically pure forms and intermediate mixtures. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers.

The stereochemistry depicted in the structures of cyclic meso compounds is not absolute; rather the stereochemistry is intended to indicate the positioning of the substituents relative to one another, e.g., cis or trans. For example,

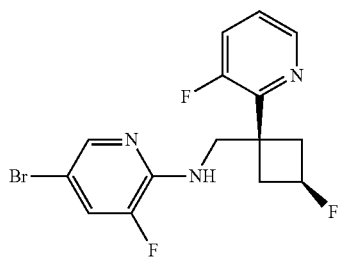 [SMILES: Fc1cc(Br)cnc1NC[C@]1(c2ncccc2F)C[C@@H](F)C1]

is intended to designate a compound wherein the fluorine and pyridyl substituents on the cyclobutyl ring are in a cis configuration to one another, while

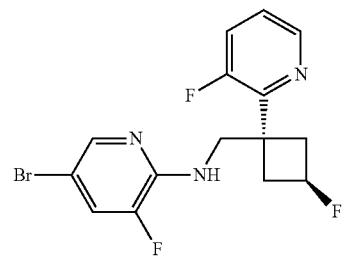 [SMILES: Fc1cc(Br)cnc1NC[C@]1(c2ncccc2F)C[C@H](F)C1]

is intended to designate a compound wherein the fluorine and pyridyl substituents on the cyclobutyl ring are in a trans configuration to one another.

When a compound can exist as one or more meso isomers, all possible meso isomers are intended to be included. For example, the compound 5-bromo-3-fluoro-N-((3-fluoro-1-(3-fluoropyridin-2-yl)cyclobutyl)methyl)pyridin-2-amine is intended to include both cis and trans meso isomers:

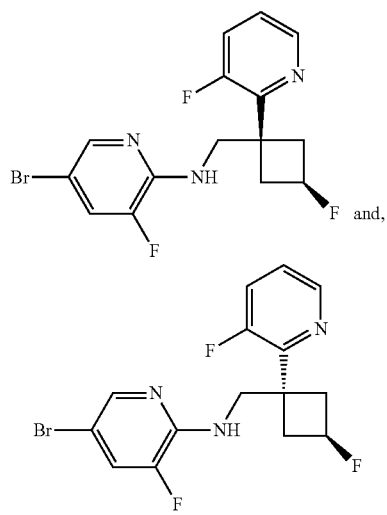

and mixtures thereof. Unless otherwise indicated, compounds disclosed and/or described herein include all possible meso isomers and mixtures thereof.

"Tautomers" are structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconverision of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to salts that retain the biological effectiveness and properties of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

A "chelate" is formed by the coordination of a compound to a metal ion at two (or more) points. The term "compound" is intended to include chelates of compounds. Similarly, "salts" includes chelates of salts and "solvates" includes chelates of solvates.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "prodrug" refers to a substance administered in an inactive or less active form that is then transformed (e.g., by metabolic processing of the prodrug in the body) into an active compound. The rationale behind administering a prodrug is to optimize absorption, distribution, metabolism, and/or excretion of the drug. Prodrugs may be obtained by making a derivative of an active compound (e.g., a compound of Formula I or another compound disclosed and/or described herein) that will undergo a transformation under the conditions of use (e.g., within the body) to form the active compound. The transformation of the prodrug to the active compound may proceed spontaneously (e.g., by way of a hydrolysis reaction) or it can be catalyzed or induced by another agent (e.g., an enzyme, light, acid or base, and/or temperature). The agent may be endogenous to the conditions of use (e.g., an enzyme present in the cells to which the prodrug is administered, or the acidic conditions of the stomach) or the agent may be supplied exogenously. Prodrugs can be obtained by converting one or more functional groups in the active compound into another functional group, which is then converted back to the original functional group when administered to the body. For example, a hydroxyl functional group can be converted to a sulfonate, phosphate, ester or carbonate group, which in turn can be hydrolyzed in vivo back to the hydroxyl group. Similarly, an amino functional group can be converted, for example, into an amide, carbamate, imine, urea, phosphenyl, phosphoryl or sulfenyl functional group, which can be hydrolyzed in vivo back to the amino group. A carboxyl functional group can be converted, for example, into an ester (including silyl esters and thioesters), amide or hydrazide functional group, which can be hydrolyzed in vivo back to the carboxyl group. Examples of prodrugs include, but are not limited to, phosphate, acetate, formate and benzoate derivatives of functional groups (such as alcohol or amine groups) present in the compounds of Formula I and other compounds disclosed and/or described herein.

The compounds disclosed and/or described herein can be enriched isotopic forms, e.g., enriched in the content of $^{2}H$, $^{3}H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The term "active agent" is used to indicate a compound that has biological activity. In some embodiments, an "active agent" is a compound having therapeutic utility. In some embodiments, the compound enhances at least one aspect of skeletal muscle function or activity, such as power output, skeletal muscle force, skeletal muscle endurance, oxygen consumption, efficiency, and/or calcium sensitivity. In some embodiments, an active agent is a compound of Formula I, or a pharmaceutically acceptable salt thereof.

The terms "patient" and "subject" refer to an animal, such as a mammal bird or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, "skeletal muscle" includes skeletal muscle tissue as well as components thereof, such as skeletal muscle fibers, the myofibrils comprising the skeletal muscle fibers, the skeletal sarcomere which comprises the myofibrils, and the various components of the skeletal sarcomere described herein, including skeletal myosin, actin, tropomyosin, troponin C, troponin I, troponin T and fragments and isoforms thereof. In some embodiments, "skeletal muscle" includes fast skeletal muscle tissue as well as components thereof, such as fast skeletal muscle fibers, the myofibrils comprising the fast skeletal muscle fibers, the fast skeletal sarcomere which comprises the myofibrils, and the various components of the fast skeletal sarcomere described herein, including fast skeletal myosin, actin, tropomyosin, troponin C, troponin I, troponin T and fragments and isoforms thereof. Skeletal muscle does not include cardiac muscle or a combination of sarcomeric components that occurs in such combination in its entirety in cardiac muscle.

As used herein, the term "therapeutic" refers to the ability to modulate the contractility of fast skeletal muscle. As used herein, "modulation" (and related terms, such as "modulate", "modulated", "modulating") refers to a change in function or efficiency of one or more components of the fast skeletal muscle sarcomere, including myosin, actin, tropomyosin, troponin C, troponin I, and troponin T from fast skeletal muscle, including fragments and isoforms thereof, as a direct or indirect response to the presence of a compound described herein, relative to the activity of the fast skeletal sarcomere in the absence of the compound. The change may be an increase in activity (potentiation) or a decrease in activity (inhibition), and may be due to the direct interaction of the compound with the sarcomere, or due to the interaction of the compound with one or more other factors that in turn affect the sarcomere or one or more of its components. In some embodiments, modulation is a potentiation of function or efficiency of one or more components of the fast skeletal muscle sarcomere, including myosin, actin, tropomyosin, troponin C, troponin I, and troponin T from fast skeletal muscle, including fragments and isoforms thereof. Modulation may be mediated by any mechanism and at any physiological level, for example, through sensitization of the fast skeletal sarcomere to contraction at lower $Ca^{2+}$ concentrations. As used herein, "efficiency" or "muscle efficiency" means the ratio of mechanical work output to the total metabolic cost.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of fast skeletal muscle. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

As used herein, "power output" of a muscle means work/cycle time and may be scaled up from PoLo/cycle time units based on the properties of the muscle. Power output may be modulated by changing, for example, activating parameters during cyclical length changes, including timing of activation (phase of activation) and the period of activation (duty cycle.)

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

Provided is a compound of Formula I:

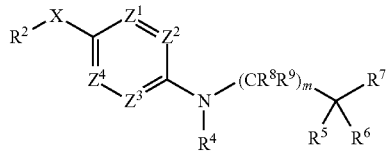

Formula I or a pharmaceutically acceptable salt thereof, wherein:

$Z^1$, $Z^2$, $Z^3$ and $Z^4$ are each independently selected from N and $CR^1$, provided that at least one of $Z^1$, $Z^2$, $Z^3$ and $Z^4$ is N and at least one of $Z^1$, $Z^2$, $Z^3$ and $Z^4$ is $CR^1$;

$R^1$, at each occurrence, is independently selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;

$R^2$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl, 5-10 membered heteroaryl and $NR^bR^c$, wherein each of the $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl groups is optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{3-8}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents;

$R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$;

$R^5$ and $R^6$ are each independently selected from hydrogen, halogen, $C_{1-6}$ alkyl and $C_{1-6}$ haloalkyl;

or alternatively, $R^5$ and $R^6$ together with the carbon atom to which they are bound form a group selected from $C_{3-8}$ cycloalkyl, $C_{3-8}$ cycloalkenyl, 3-8 membered heterocycloalkyl and 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl;

$R^7$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^8$ and $R^9$, at each occurrence, are each independently selected from hydrogen, halogen and $C_{1-6}$ alkyl;

X is selected from a bond, $-(CH_2)_p-$, $-(CH_2)_pC(O)(CH_2)_q-$, $-(CH_2)_pO(CH_2)_q-$, $-(CH_2)_pS(CH_2)_q-$, $-(CH_2)_pNR^d(CH_2)_q-$, $-(CH_2)_pC(O)O(CH_2)_q-$, $-(CH_2)_pOC(O)(CH_2)_q-$, $-(CH_2)_pNR^dC(O)(CH_2)_q-$, $-(CH_2)_pC(O)NR^d(CH_2)_q-$, $-(CH_2)_pNR^dC(O)NR^d(CH_2)_q-$, $-(CH_2)_pNR^dSO_2(CH_2)_q-$, and $-(CH_2)_pSO_2NR^d(CH_2)_q-$;

$R^a$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^b$ and $R^c$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, $C(O)OR^g$, $C(O)NR^iR^j$ and $SO_2R^g$, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^d$, at each occurrence, is independently selected from hydrogen and $C_{1-6}$ alkyl;

$R^e$, at each occurrence, is independently selected from hydrogen, CN, OH, $C_{1-6}$ alkoxy, $C_{1-6}$ alkyl and $C_{1-6}$ haloalkyl;

$R^f$, at each occurrence, is independently selected from halogen, CN, $OR^h$, $OC(O)R^h$, $OC(O)OR^h$, $OC(O)NR^iR^j$, $NR^iR^j$, $NR^dC(O)R^h$, $NR^dC(O)OR^h$, $NR^dC(O)NR^iR^j$, $NR^dC(O)C(O)NR^iR^j$, $NR^dC(S)R^h$, $NR^dC(S)OR^h$, $NR^dC(S)NR^iR^j$, $NR^dC(NR^e)NR^iR^j$, $NR^dS(O)R^h$, $NR^dSO_2R^h$, $NR^dSO_2NR^iR^j$, $C(O)R^h$, $C(O)OR^h$, $C(O)NR^iR^j$, $C(S)R^h$, $C(S)OR^h$, $C(S)NR^iR^j$, $C(NR^e)NR^iR^j$, $SR^h$, $S(O)R^h$, $SO_2R^h$, $SO_2NR^iR^j$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

or two $R^f$ substituents bound to a single carbon atom, together with the carbon atom to which they are both bound, form a group selected from carbonyl, $C_{3-8}$ cycloalkyl and 3-8 membered heterocycloalkyl;

$R^g$, at each occurrence, is independently selected from $C_{1-6}$ alkyl, $C_{1-6}$ haloalkyl, phenyl, naphthyl, and $C_{7-11}$ aralkyl, each optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^h$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

$R^i$ and $R^j$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, and $C(O)OR^g$, wherein each of the $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^k$, at each occurrence, is independently selected from halogen, CN, oxo, OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, $NHC(O)OC_{7-11}$ aralkyl, $C(O)C_{1-6}$ alkyl, $C(O)C_{7-11}$ aralkyl, $C(O)OC_{1-6}$ alkyl, $C(O)OC_{7-11}$ aralkyl, $C_{1-6}$ alkyl, $C_{1-6}$ haloalkyl, $C_{2-6}$ alkenyl, and $C_{2-6}$ alkynyl, wherein each $C_{1-6}$ alkyl, $C_{2-6}$ alkenyl, $C_{2-6}$ alkynyl, and $C_{7-11}$ aralkyl substituent is optionally substituted with 1, 2 or 3 substituents selected from OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, and $NHC(O)OC_{7-11}$ aralkyl;

m is 0, 1 or 2;

n, at each occurrence, independently is 0, 1 or 2;

p is 0, 1 or 2; and q is 0, 1 or 2.

In some embodiments of compounds of Formula I, $Z^1$ and $Z^2$ are each N, one of $Z^3$ and $Z^4$ is N, and the other of $Z^3$ and $Z^4$ is $CR^1$.

In some embodiments of compounds of Formula I, $Z^1$, $Z^2$ and $Z^3$ are each N and $Z^4$ is $CR^1$, i.e., a compound of Formula II, or a pharmaceutically acceptable salt thereof:

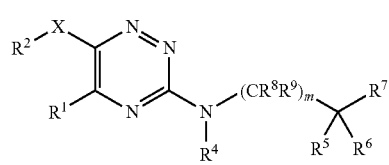

Formula II wherein $R^1$, $R^2$, $R^4$, $R^5$, $R^6$, $R^7$, $R^8$, $R^9$, X and m are as defined herein.

In some embodiments of compounds of Formula I, $Z^1$, $Z^2$ and $Z^4$ are each N and $Z^3$ is $CR^1$, i.e., a compound of Formula III, or a pharmaceutically acceptable salt thereof:

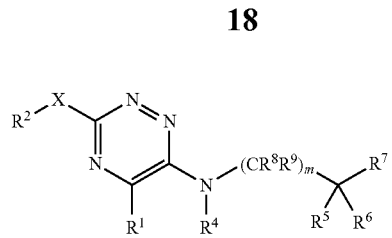

Formula III wherein $R^1$, $R^2$, $R^4$, $R^5$, $R^6$, $R^7$, $R^8$, $R^9$, X and m are as defined herein.

In some embodiments of compounds of Formula I, one of $Z^1$ and $Z^2$ is N, the other of $Z^1$ and $Z^2$ is $CR^1$, and $Z^3$ and $Z^4$ are each $CR^1$.

In some embodiments of compounds of Formula I, $Z^1$, $Z^3$ and $Z^4$ are each $CR^1$ and $Z^2$ is N, i.e., a compound of Formula IV, or a pharmaceutically acceptable salt thereof:

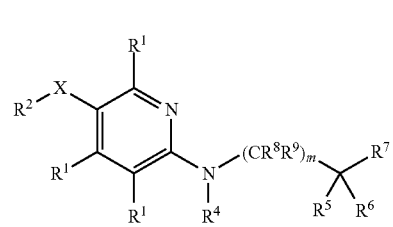

Formua IV wherein $R^1$, $R^2$, $R^4$, $R^5$, $R^6$, $R^7$, $R^8$, $R^9$, X and m are as defined herein.

In some embodiments of compounds of Formula I, $Z^2$, $Z^3$ and $Z^4$ are each $CR^1$ and $Z^1$ is N, i.e., a compound of Formula V, or a pharmaceutically acceptable salt thereof:

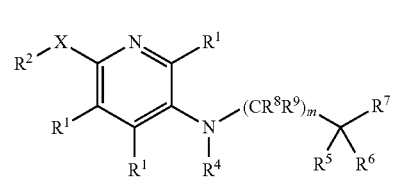

Formula V wherein $R^1$, $R^2$, $R^4$, $R^5$, $R^6$, $R^7$, $R^8$, $R^9$, X and m are as defined herein.

In some embodiments of compounds of Formula I, II, III, IV or V, m is 0, i.e., a compound of Formula II(a), III(a), IV(a) or V(a), or a pharmaceutically acceptable salt thereof:

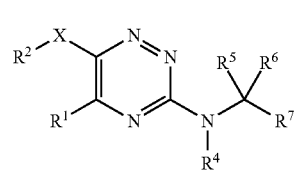

Formula II(a)

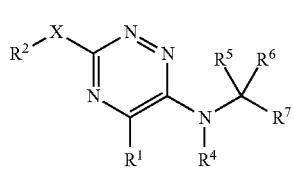

Formula III(a)

-continued

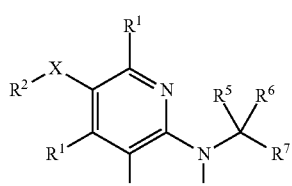
Formula IV(a)

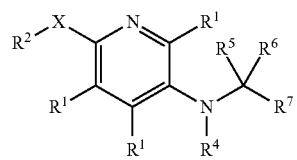
Formula V(a)

wherein $R^1$, $R^2$, $R^4$, $R^5$, $R^6$, $R^7$ and X are as defined herein.

In some embodiments of compounds of Formula I, II, III, IV or V, m is 1, i.e., a compound of Formula II(b), III(b), IV(b) or V(b), or a pharmaceutically acceptable salt thereof:

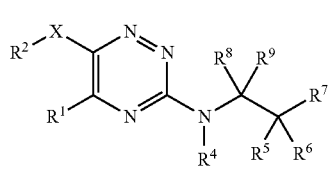
Formula II(b)

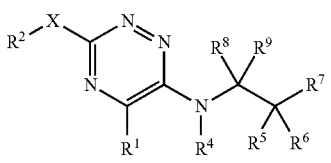
Formula III(b)

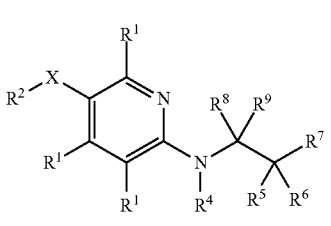
Formula IV(b)

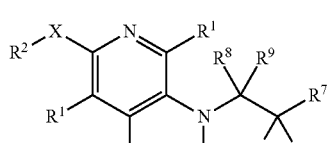
Formula V(b)

wherein $R^1$, $R^2$, $R^4$, $R^5$, $R^6$, $R^7$, $R^8$, $R^9$ and X are as defined herein.

In some embodiments of compounds of Formula I, II, II(a), II(b), III, III(a), III(b), IV, IV(a), IV(b) V, V(a) or V(b), one of $R^5$ and $R^6$ is hydrogen and the other is $C_{1-6}$ alkyl.

In some embodiments of compounds of Formula I, II, II(a), II(b), III, III(a), III(b), IV, IV(a), IV(b) V, V(a) or V(b), $R^5$ and $R^6$ are each independently $C_{1-6}$ alkyl.

In some embodiments of compounds of Formula I, II, II(a), II(b), III, III(a), III(b), IV, IV(a), IV(b) V, V(a) or V(b), $R^5$ and $R^6$ are each methyl.

In some embodiments, the compounds are of Formula II(c) or II(d), or a pharmaceutically acceptable salt thereof:

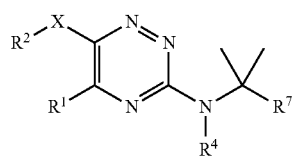
Formula II(c)

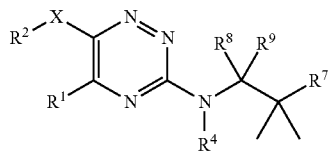
Formula II(d)

wherein $R^1$, $R^2$, $R^4$, $R^7$, $R^8$, $R^9$ and X are as defined herein.

In some embodiments, the compounds are of Formula III(c) or III(d), or a pharmaceutically acceptable salt thereof:

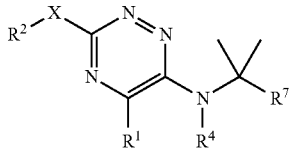
Formula III(c)

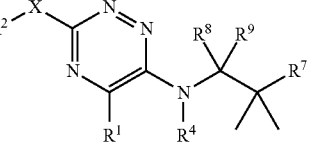
Formula III(d)

wherein $R^1$, $R^2$, $R^4$, $R^7$, $R^8$, $R^9$ and X are as defined herein.

In some embodiments, the compounds are of Formula IV(c) or IV(d), or a pharmaceutically acceptable salt thereof:

Formula IV(c)

Formula IV(d)

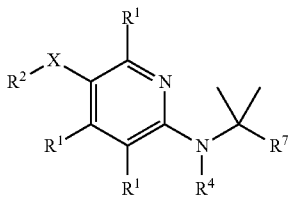

wherein $R^1$, $R^2$, $R^4$, $R^7$, $R^8$, $R^9$ and X are as defined herein.

In some embodiments, the compounds are of Formula V(c) or V(d), or a pharmaceutically acceptable salt thereof:

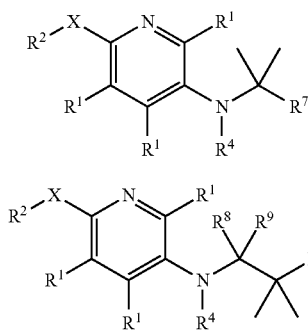

Formula V(c)

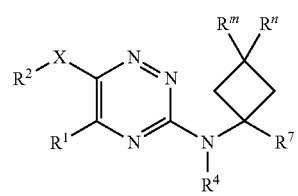

Formula V(d)

wherein $R^1$, $R^2$, $R^4$, $R^7$, $R^8$, $R^9$ and X are as defined herein.

In some embodiments of compounds of Formula I, II, II(a), II(b), III, III(a), III(b), IV, IV(a), IV(b) V, V(a) or V(b), $R^5$ and $R^6$ together with the carbon atom to which they are bound form $C_{3-8}$ cycloalkyl, $C_{3-8}$ cycloalkenyl, 3-8 membered heterocycloalkyl or 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II, II(a), II(b), III, III(a), III(b), IV, IV(a), IV(b) V, V(a) or V(b), $R^5$ and $R^6$, together with the carbon to which they are bound, form $C_{3-6}$ cycloalkyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II, II(a), II(b), III, III(a), III(b), IV, IV(a), IV(b) V, V(a) or V(b), $R^5$ and $R^6$, together with the carbon to which they are bound, form cyclopropyl, cyclobutyl, cyclopentyl or cyclohexyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II, II(a), II(b), III, III(a), III(b), IV, IV(a), IV(b) V, V(a) or V(b), $R^5$ and $R^6$, together with the carbon to which they are bound, form cyclobutyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

In some embodiments of compounds of Formula I, II, II(a), II(b), III, III(a), III(b), IV, IV(a), IV(b) V, V(a) or V(b), $R^5$ and $R^6$, together with the carbon to which they are bound, form cyclobutyl substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl, wherein the substituent and $R^7$ are in a trans configuration with respect to one another on the cyclobutyl ring.

In some embodiments of compounds of Formula I, II, II(a), II(b), III, III(a), III(b), IV, IV(a), IV(b) V, V(a) or V(b), $R^5$ and $R^6$, together with the carbon to which they are bound, form cyclobutyl substituted with one substituent selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl, wherein the substituent and $R^7$ are in a cis configuration with respect to one another on the cyclobutyl ring.

In some embodiments, the compounds are of Formula II(e) or II(f), or a pharmaceutically acceptable salt thereof:

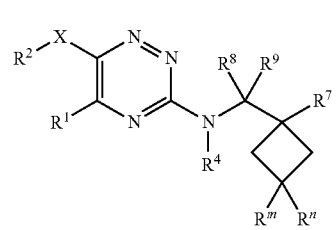

Formula II(e)

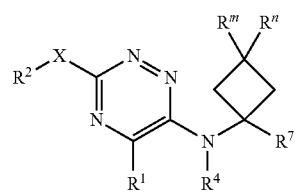

Formula II(f)

wherein $R^m$ and $R^n$ are each independently selected from hydrogen and halogen, and $R^1$, $R^2$, $R^4$, $R^7$, $R^8$, $R^9$ and X are as defined herein.

In some embodiments, the compounds are of Formula III(e) or III(f), or a pharmaceutically acceptable salt thereof:

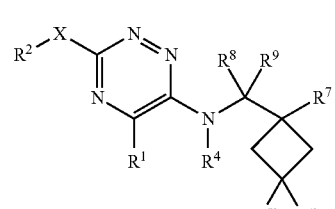

Formula III(e)

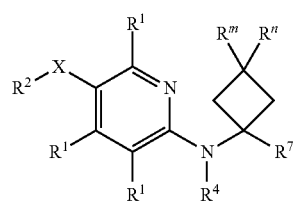

Formula III(f)

wherein $R^m$ and $R^n$ are each independently selected from hydrogen and halogen, and $R^1$, $R^2$, $R^4$, $R^7$, $R^8$, $R^9$ and X are as defined herein.

In some embodiments, the compounds are of Formula IV(e) or IV(f), or a pharmaceutically acceptable salt thereof:

Formula IV(e)

Formula IV(f)

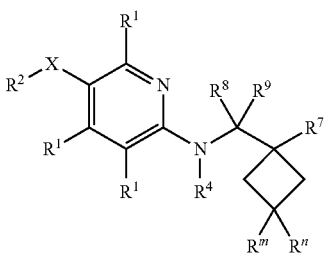

wherein R^m and R^n are each independently selected from hydrogen and halogen, and R^1, R^2, R^4, R^7, R^8, R^9 and X are as defined herein.

In some embodiments, the compounds are of Formula V(e) or V(f), or a pharmaceutically acceptable salt thereof:

Formula V(e)

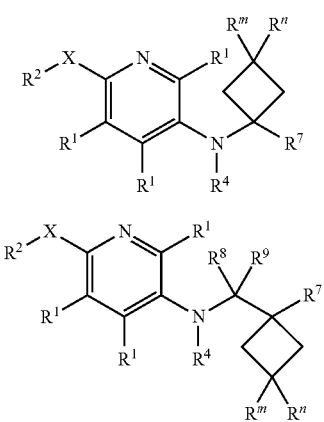

Formula V(f)

wherein R^m and R^n are each independently selected from hydrogen and halogen, and R^1, R^2, R^4, R^7, R^8, R^9 and X are as defined herein.

In some embodiments of compounds of Formula II(e), IV), III(e), III(f), IV(e), IV(f), V(e) or V(f), R^m and R^n are each hydrogen.

In some embodiments compounds of Formula II(e), IV), III(e), III(f), IV(e), IV(f), V(e) or V(f), R^m and R^n are each halogen.

In some embodiments compounds of Formula II(e), IV), III(e), III(f), IV(e), IV(f), V(e) or V(f), R^m and R^n are each fluorine.

In some embodiments of compounds of Formula II(e), IV), III(e), III(f), IV(e), IV(f), V(e) or V(f), one of R^m and R^n is hydrogen and the other is halogen. In some embodiments of such compounds, the halogen and R^7 are in a trans configuration with respect to one another on the cyclobutyl ring. In some embodiments of such compounds, the halogen and R^7 are in a cis configuration with respect to one another on the cyclobutyl ring.

In some embodiments of compounds of Formula II(e), IV), III(e), III(f), IV(e), IV(f), V(e) or V(f), one of R^m and R^n is hydrogen and the other is fluorine. In some embodiments of such compounds, the fluorine and R^7 are in a trans configuration with respect to one another on the cyclobutyl ring. In some embodiments of such compounds, the fluorine and R^7 are in a cis configuration with respect to one another on the cyclobutyl ring.

In some embodiments of compounds of Formula I, II, II(a), II(b), III, III(a), III(b), IV, IV(a), IV(b) V, V(a) or V(b), R^5 and R^6, together with the carbon atom to which they are bound, form 3-6 membered heterocycloalkyl optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), III, III(a), III(b), IV, IV(a), IV(b) V, V(a) or V(b), R^5 and R^6, together with the carbon atom to which they are bound, form aziridine, azetidine, pyrrolidine, oxirane, oxetane or tetrahydrofuran, each of which is optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), III, III(a), III(b), IV, IV(a), IV(b) V, V(a) or V(b), R^5 and R^6 are each independently C_{1-6} alkyl, or R^5 and R^6 together with the carbon atom to which they are bound form C_{3-8} cycloalkyl, C_{3-8} cycloalkenyl, 3-8 membered heterocycloalkyl or 3-8 membered heterocycloalkenyl, each optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), III, III(a), III(b), IV, IV(a), IV(b) V, V(a) or V(b), R^5 and R^6 are each methyl, or R^5 and R^6 together with the carbon atom to which they are bound form C_{3-8} cycloalkyl, C_{3-8} cycloalkenyl, 3-8 membered heterocycloalkyl or 3-8 membered heterocycloalkenyl, each optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), III, III(a), III(b), IV, IV(a), IV(b) V, V(a) or V(b), R^5 and R^6 are each independently C_{1-6} alkyl, or R^5 and R^6, together with the carbon to which they are bound, form a group selected from cyclopropyl, cyclobutyl, cyclopentyl or cyclohexyl, each optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), III, III(a), III(b), IV, IV(a), IV(b) V, V(a) or V(b), R^5 and R^6 are each methyl, or R^5 and R^6, together with the carbon to which they are bound, form cyclobutyl optionally substituted with 1, 2, 3, 4 or 5 substituents selected from halogen, CN, oxo, OR^a, OC(O)R^a, OC(O)OR^a, NR^bR^c, C(O)R^a, C(O)OR^a, C(O)NR^bR^c, S(O)R^a, SO_2R^a, SO_2NR^bR^c, C_{1-6} alkyl and C_{1-6} haloalkyl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R^7 is selected from C_{3-8} cycloalkyl, C_{3-8} cycloalkenyl, 3-8 membered heterocycloalkyl, 3-8 membered heterocycloalkenyl, C_{6-10} aryl and 5-10 membered heteroaryl, each optionally substituted with 1, 2, 3, 4 or 5 substituents selected from halogen, CN, oxo, OR^a, OC(O)R^a, OC(O)OR^a, OC(O)NR^bR^c, NR^bR^c, NR^dC(O)R^a, NR^dC(O)OR^a, NR^dC(O)NR^bR^c, NR^dC(O)C(O)NR^bR^c, NR^dC(S)R^a, NR^dC(S)OR^a, NR^dC(S)NR^bR^c, NR^dC(NR^e)NR^bR^c, NR^dS(O)R^a, NR^dSO_2R^a, NR^dSO_2NR^bR^c, C(O)R^a, C(O)OR^a, C(O)NR^bR^c, C(S)R^a, C(S)OR^a, C(S)NR^bR^c, C(NR^e)NR^bR^c, SR^a, S(O)R^a, SO_2R^a, SO_2NR^bR^c, C_{1-6} alkyl, C_{1-6} haloalkyl, C_{2-6} alkenyl, C_{2-6} alkynyl, C_{3-8} cycloalkyl, C_{3-8} cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^7$ is phenyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^7$ is selected from phenyl, 2-fluorophenyl, 3-fluorophenyl, 2,4-difluorophenyl, 3,4-difluorophenyl, 3,5-difluorophenyl, 4-fluorophenyl, 2-chlorophenyl, 3-chlorophenyl, 4-chlorophenyl, 2,4-dichlorophenyl, 3,4-dichlorophenyl, 3,5-dichlorophenyl, 2-methylphenyl, 3-methylphenyl, 2,4-dimethylphenyl, 3,4-dimethylphenyl, 3,5-dimethylphenyl, 2-(hydroxymethyl)phenyl, 3-(hydroxymethyl)phenyl, 4-(hydroxymethyl)phenyl, 2-(aminomethyl)phenyl, 3-(aminomethyl)phenyl, 4-(aminomethyl)phenyl, 2-phenol, 3-phenol, 4-phenol, 2-methoxyphenyl, 3-methoxyphenyl, 4-methoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 2-cyanophenyl, 3-cyanophenyl, 4-cyanophenyl, 2-benzamine, 3-benzamide, 4-benzamide, N-methyl-2-benzamine, N-methyl-3-benzamide, N-methyl-4-benzamide, N,N-dimethyl-2-benzamine, N,N-dimethyl-3-benzamide, and N,N-dimethyl-4-benzamide.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^7$ is 5-10 membered heteroaryl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^7$ is pyridyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^7$ is selected from 2-pyridyl, 3-pyridyl and 4-pyridyl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

In some embodiments of compounds of Formula I, II, III, IV(a), IV(b), V(a) or V(b), $R^7$ is selected from pyrid-2-yl, 3-fluoro-pyrid-2-yl, 4-fluoro-pyrid-2-yl, 5-fluoro-pyrid-2-yl, 6-fluoro-pyrid-2-yl, 3-chloro-pyrid-2-yl, 4-chloro-pyrid-2-yl, 5-chloro-pyrid-2-yl, 6-chloro-pyrid-2-yl, 3-cyano-pyrid-2-yl, 4-cyano-pyrid-2-yl, 5-cyano-pyrid-2-yl, 6-cyano-pyrid-2-yl, 3-methyl-pyrid-2-yl, 4-methyl-pyrid-2-yl, 5-methyl-pyrid-2-yl, 6-methyl-pyrid-2-yl, 3-difluoromethyl-pyrid-2-yl, 4-difluoromethyl-pyrid-2-yl, 5-difluoromethyl-pyrid-2-yl, 6-difluoromethyl-pyrid-2-yl, 3-trifluoromethyl-pyrid-2-yl, 4-trifluoromethyl-pyrid-2-yl, 5-trifluoromethyl-pyrid-2-yl, 6-trifluoromethyl-pyrid-2-yl, 3-hydroxymethyl-pyrid-2-yl, 4-hydroxymethyl-pyrid-2-yl, 5-hydroxymethyl-pyrid-2-yl, 6-hydroxymethyl-pyrid-2-yl, 3-aminomethyl-pyrid-2-yl, 4-aminomethyl-pyrid-2-yl, 5-aminomethyl-pyrid-2-yl, 6-aminomethyl-pyrid-2-yl, 3-hydroxy-pyrid-2-yl, 4-hydroxy-pyrid-2-yl, 5-hydroxy-pyrid-2-yl, 6-hydroxy-pyrid-2-yl, 3-methoxy-pyrid-2-yl, 4-methoxy-pyrid-2-yl, 5-methoxy-pyrid-2-yl, 6-methoxy-pyrid-2-yl, 3-difluoromethoxy-pyrid-2-yl, 4-difluoromethoxy-pyrid-2-yl, 5-difluoromethoxy-pyrid-2-yl, 6-difluoromethoxy-pyrid-2-yl, 3-trifluoromethoxy-pyrid-2-yl, 4-trifluoromethoxy-pyrid-2-yl, 5-trifluoromethoxy-pyrid-2-yl, 6-trifluoromethoxy-pyrid-2-yl, 3-methylthio-pyrid-2-yl, 4-methylthio-pyrid-2-yl, 5-methylthio-pyrid-2-yl, 6-methylthio-pyrid-2-yl, 3-carboxamide-pyrid-2-yl, 4-carboxamide-pyrid-2-yl, 5-carboxamide-pyrid-2-yl, 6-carboxamide-pyrid-2-yl and 3-fluoro-6-methyl-pyrid-2-yl.

In some embodiments of compounds of Formula I, II, III, IV(a), IV(b), V(a) or V(b), $R^7$ is selected from pyrid-3-yl, 2-fluoro-pyrid-3-yl, 4-fluoro-pyrid-3-yl, 5-fluoro-pyrid-3-yl, 6-fluoro-pyrid-3-yl, 2-chloro-pyrid-3-yl, 4-chloro-pyrid-3-yl, 5-chloro-pyrid-3-yl, 6-chloro-pyrid-3-yl, 2-cyano-pyrid-3-yl, 4-cyano-pyrid-3-yl, 5-cyano-pyrid-3-yl, 6-cyano-pyrid-3-yl, 2-methyl-pyrid-3-yl, 4-methyl-pyrid-3-yl, 5-methyl-pyrid-3-yl, 6-methyl-pyrid-3-yl, 2-difluoromethyl-pyrid-3-yl, 4-difluoromethyl-pyrid-3-yl, 5-difluoromethyl-pyrid-3-yl, 6-difluoromethyl-pyrid-3-yl, 2-trifluoromethyl-pyrid-3-yl, 4-trifluoromethyl-pyrid-3-yl, 5-trifluoromethyl-pyrid-3-yl, 6-trifluoromethyl-pyrid-3-yl, 2-hydroxymethyl-pyrid-3-yl, 4-hydroxymethyl-pyrid-3-yl, 5-hydroxymethyl-pyrid-3-yl, 6-hydroxymethyl-pyrid-3-yl, 2-aminomethyl-pyrid-3-yl, 4-aminomethyl-pyrid-3-yl, 5-aminomethyl-pyrid-3-yl, 6-aminomethyl-pyrid-3-yl, 2-hydroxy-pyrid-3-yl, 4-hydroxy-pyrid-3-yl, 5-hydroxy-pyrid-3-yl, 6-hydroxy-pyrid-3-yl, 2-methoxy-pyrid-3-yl, 4-methoxy-pyrid-3-yl, 5-methoxy-pyrid-3-yl, 6-methoxy-pyrid-3-yl, 2-difluoromethoxy-pyrid-3-yl, 4-difluoromethoxy-pyrid-3-yl, 5-difluoromethoxy-pyrid-3-yl, 6-difluoromethoxy-pyrid-3-yl, 2-trifluoromethoxy-pyrid-3-yl, 4-trifluoromethoxy-pyrid-3-yl, 5-trifluoromethoxy-pyrid-3-yl, 6-trifluoromethoxy-pyrid-3-yl, 2-methylthio-pyrid-3-yl, 4-methylthio-pyrid-3-yl, 5-methylthio-pyrid-3-yl, 6-methylthio-pyrid-3-yl, 2-carboxamide-pyrid-3-yl, 4-carboxamide-pyrid-3-yl, 5-carboxamide-pyrid-3-yl and 6-carboxamide-pyrid-3-yl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is selected from a bond, —(CH$_2$)$_p$—, —(CH$_2$)$_p$C(O)(CH$_2$)$_q$—, —(CH$_2$)$_p$O(CH$_2$)$_q$—, —(CH$_2$)$_p$S(CH$_2$)$_q$—, —(CH$_2$)$_p$NR$^d$(CH$_2$)$_q$—, —(CH$_2$)$_p$C(O)O(CH$_2$)$_q$—, —(CH$_2$)$_p$OC(O)(CH$_2$)$_q$—, —(CH$_2$)$_p$NR$^d$C(O)(CH$_2$)$_q$—, —(CH$_2$)$_p$C(O)NR$^d$(CH$_2$)$_q$—, —(CH$_2$)$_p$NR$^d$C(O)NR$^d$(CH$_2$)$_q$—, —(CH$_2$)$_p$NR$^d$SO$_2$(CH$_2$)$_q$—, and —(CH$_2$)$_p$SO$_2$NR$^d$(CH$_2$)$_q$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is a bond.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —O—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is selected from —CH$_2$O— and —OCH$_2$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —NR$^d$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is selected from —CH$_2$NR$^d$— and —NR$^d$CH$_2$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is selected from —NR$^d$C(O)— and —C(O)NR$^d$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is selected from —CH$_2$NR$^d$C(O)— and —C(O)NR$^d$CH$_2$—.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl, 5-10 membered heteroaryl and NR$^b$R$^c$, wherein each of the $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl groups is optionally substituted with 1, 2, 3, 4 or 5 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, $C_{1-6}$ alkyl, $C_{1-6}$ haloalkyl, $C_{2-6}$ alkenyl, $C_{2-6}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl, wherein each of the $C_{1-6}$ alkyl, $C_{2-6}$ alkenyl, $C_{2-6}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl optionally substituted with 1, 2, 3, 4 or 5 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, $C_{1-8}$ alkyl, $C_{1-8}$ haloalkyl, $C_{2-6}$ alkenyl, $C_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl, wherein each of the $C_{1-6}$ alkyl, $C_{3-8}$ alkenyl, $C_{2-6}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted with 1, 2, 3, 4 or 5 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-8}$ alkyl, $C_{1-8}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{3-8}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents; wherein at least one substituent is bonded at the meta position.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted with a substituent selected from $(CH_2)_nC(O)OR^a$ and $(CH_2)_nC(O)NR^bR^c$; and optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted with a substituent selected from C(O)OH, C(O)NH$_2$, C(O)OC$_{1-6}$ alkyl, C(O)NHC$_{1-6}$ alkyl and C(O)N(C$_{1-6}$ alkyl)$_2$; and optionally substituted with 1, 2 or 3 additional substituents selected from halogen, $C_{1-6}$ alkyl and $C_{1-6}$ haloalkyl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted at the meta position with a substituent selected from $(CH_2)_nC(O)OR^a$ and $(CH_2)_nC(O)NR^bR^c$; and optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted at the meta position with a substituent selected from $(CH_2)_nC(O)OR^a$ and $(CH_2)_nC(O)NR^bR^c$, and optionally substituted with 1, 2 or 3 additional substituents selected from halogen, hydroxyl, CN, $C_{1-6}$ alkyl and $C_{1-6}$ haloalkyl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted at the meta position with a substituent selected from C(O)OH, C(O)NH$_2$, C(O)OC$_{1-6}$ alkyl, C(O)NHC$_{1-6}$ alkyl and C(O)N(C$_{1-6}$ alkyl)$_2$; and optionally substituted with 1, 2 or 3 additional substituents selected from halogen, hydroxyl, CN, $C_{1-6}$ alkyl and $C_{1-6}$ haloalkyl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted with $(CH_2)_nNR^dC(O)R^a$, wherein $R^a$ is $C_{1-6}$ alkyl or 3-8 membered heterocycloalkyl, each optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl; and optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is phenyl substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 additional substituents selected from halogen, CN, oxo, $(CH_2)_nOR^a$, $(CH_2)_nOC(O)R^a$, $(CH_2)_nOC (O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, and (CH$_2$)$_n$5-10 membered heteroaryl; and optionally substituted with 1, 2 or 3 additional substituents selected from halogen, CN, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from 3-benzamide, N-methyl-3-benzamide, N,N-dimethyl-3-benzamide, 4-fluoro-3-benzamide, N-methyl-4-fluoro-3-benzamide, N,N-dimethyl-4-fluoro-3-benzamide, 3-benzoic acid, methyl-3-benzoate, 4-fluoro-3-benzoic acid, and methyl-4-fluoro-3-benzoate.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is 5-10 membered heteroaryl optionally substituted with 1, 2, 3, 4 or 5 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-8}$ alkyl, C$_{1-8}$ haloalkyl, C$_{2-6}$ alkenyl, C$_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl, wherein each of the C$_{1-6}$ alkyl, C$_{3-8}$ alkenyl, C$_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with 1, 2, 3 or 4 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl, wherein each of the C$_{1-6}$ alkyl, C$_{3-8}$ alkenyl, C$_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with a substituent selected from (CH$_2$)$_n$C(O)OR$^a$ and (CH$_2$)$_n$C(O)NR$^b$R$^c$; and optionally substituted with 1, 2 or 3 additional substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-8}$ alkyl, C$_{1-8}$ haloalkyl, C$_{2-6}$ alkenyl, C$_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl, wherein each of the C$_{1-6}$ alkyl, C$_{3-8}$ alkenyl, C$_{3-8}$ alkynyl, (CH$_2$)$_n$C$_{3-8}$ cycloalkyl, (CH$_2$)$_n$3-8 membered heterocycloalkyl, (CH$_2$)$_n$C$_{6-10}$ aryl and (CH$_2$)$_n$5-10 membered heteroaryl groups is optionally substituted with 1, 2, 3, 4 or 5 R$^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from pyridyl, pyrimidyl, pyrazyl, pyridazyl and triazyl, each optionally substituted with (CH$_2$)$_n$C(O)NR$^b$R$^c$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with (CH$_2$)$_n$C(O)NR$^b$R$^c$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from pyridyl, pyrimidyl, pyrazyl, pyridazyl and triazyl, each optionally substituted with (CH$_2$)$_n$C(O)NH$_2$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), R$^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nC(O)NH_2$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is $C_{1-6}$ alkyl or 3-8 membered heterocycloalkyl, each optionally substituted with 1, 2 or 3 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-8}$ alkyl, $C_{1-8}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-8}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from pyridyl, pyrimidyl, pyrazyl, pyridazyl and triazyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from indolyl, indazolyl, benzimidazolyl, benzoxazolyl and benzoisoxazolyl, each optionally substituted with 1, 2, 3 or 4 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-8}$ alkyl, $C_{1-8}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$Phenyl, $(CH_2)_n$naphthyl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from 1H-indazol-6-yl, 1H-indazol-5-yl, 1H-indazol-4-yl, 3-amino(1H-indazol-5-yl), 3-amino(1H-indazol-6-yl), 3-amino(1H-indazol-7-yl), 1-methyl(1H-indazol-6-yl), 3-methyl(1H-indazol-6-yl), 3-amino-1-methyl(1H-indazol-5-yl), 3-cyano(1H-indazol-5-yl), 3-carboxamide(1H-indazol-5-yl), 3-carboxamidine(1H-indazol-5-yl), 3-vinyl(1H-indazol-5-yl), 3-ethyl(1H-indazol-5-yl), 3-acetamide(1H-indazol-5-yl), 3-methylsulfonylamine(1H-indazol-5-yl), 3-methoxycarboxamide(1H-indazol-5-yl), 3-methylamino(1H-indazol-5-yl), 3-dimethylamino(1H-indazol-5-yl), 3-ethylamino(1H-indazol-5-yl), 3-(2-aminoethyl)amino(1H-indazol-5-yl), 3-(2-hydroxyethyl)amino(1H-indazol-5-yl), 3-[(methylethyl)amino](1H-indazol-5-yl), 6-benzimidazol-5-yl, 6-(2-methylbenzimidazol-5-yl), 2-aminobenzimidazol-5-yl, 2-hydroxybenzimidazol-5-yl, 2-acetamidebenzimidazol-5-yl, 3-aminobenzo[3,4-d]isoxazol-5-yl, 3-aminobenzo[d]isoxazol-6-yl, 3-aminobenzo[d]isoxazol-7-yl, 2-methylbenzoxazol-5-yl and 2-methylbenzoxazol-6-yl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from 3-6 membered heterocycloalkyl and 3-6 membered heterocycloalkenyl, each optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-8}$ alkyl, $C_{1-8}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{3-8}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is selected from aziridinyl, azetidinyl, pyrrolidinyl, piperidinyl, piperazinyl and morpholinyl, each optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-8}$ alkyl, $C_{1-8}$ haloalkyl, $C_{2-6}$ alkenyl, $C_{3-8}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{3-8}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is $NR^bR^c$, wherein $R^b$ and $R^c$ are as defined herein.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^2$ is $NR^bR^c$, wherein one of $R^b$ and $R^c$ is hydrogen and the other is $C_{1-6}$ alkyl optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —C(O)— and $R^2$ is $NR^bR^c$, wherein $R^b$ and $R^c$ are as defined herein.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —C(O)— and $R^2$ is $NR^bR^c$, wherein one of $R^b$ and $R^c$ is hydrogen and the other is $C_{1-6}$ alkyl optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —$(CH_2)_p$— and $R^2$ is $NR^bR^c$, wherein $R^b$ and $R^c$ are as defined herein.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), X is —$(CH_2)_p$— and $R^2$ is $NR^bR^c$, wherein one of $R^b$ and $R^c$ is hydrogen and the other is $C_{1-6}$ alkyl optionally substituted with 1, 2, 3, 4 or 5 $R^f$ substituents.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^1$, at each occurrence, is independently selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^1$, at each occurrence, is independently selected from hydrogen, halogen, CN, $C_{1-6}$ alkyl, $C_{1-6}$ haloalkyl, hydroxyl, $C_{1-6}$ alkoxy, $NH_2$, $NHC_{1-6}$ alkyl, and $N(C_{1-6}$ alkyl$)_2$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^1$, at each occurrence, is independently selected from hydrogen, halogen, CN, $CF_3$ and methyl.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^1$, at each occurrence, is hydrogen.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^4$ is hydrogen.

In some embodiments of compounds of Formula I, II, II(a), II(b), II(c), II(d), II(e), II(f), III(a), III(b), III(c), III(d), III(e), III(f), IV(a), IV(b), IV(c), IV(d), IV(e), IV(f), V(a), V(b), V(c), V(d), V(e) or V(f), $R^4$ is hydrogen and each $R^1$ is hydrogen.

In some embodiments of compounds of Formula I, II, II(b), II(d), II(f), III(b), III(d), III(f), IV(b), IV(d), IV(f), V(b), V(d) or V(f), $R^8$ and $R^9$, at each occurrence, are each independently selected from hydrogen, halogen and $C_{1-6}$ alkyl.

In some embodiments of compounds of Formula I, II, II(b), II(d), II(f), III(b), III(d), III(f), IV(b), IV(d), IV(f), V(b), V(d) or V(f), $R^8$ and $R^9$, at each occurrence, are each hydrogen.

In some embodiments, the compound is selected from the compounds in Table 2, or a pharmaceutically acceptable salt thereof.

The compounds and compositions described and/or disclosed herein modulate the contractility of the skeletal sarcomere. Specifically, the compounds modulate the troponin complex of the fast skeletal muscle sarcomere through one or more of fast skeletal myosin, actin, tropomyosin, troponin C, troponin I, and troponin T, and fragments and isoforms thereof. As used in this context, "modulate" means either increasing or decreasing activity. In some instances, the compounds described and/or disclosed herein potentiate (i.e., increase activity) of one or more of fast skeletal myosin, actin, tropomyosin, troponin C, troponin I, and troponin T, and fragments and isoforms thereof. In other instances, the compounds described and/or disclosed herein inhibit (i.e., decrease activity) of one or more of fast skeletal myosin, actin, tropomyosin, troponin C, troponin I, and troponin T, and fragments and isoforms thereof.

In both preclinical and clinical settings, activators of the fast skeletal troponin complex have been shown to amplify the response of fast skeletal muscle to nerve stimulation, resulting in an increase in muscle force development at submaximal muscle activation (see, e.g., Russell et al., "The Fast Skeletal Troponin Activator, CK-2017357, Increases Skeletal Muscle Force in vitro and in situ", 2009 Experimental Biology Conference, New Orleans, La., April 2009). Activators of the fast skeletal troponin complex have been shown to increase the sensitivity of skinned skeletal muscle fibers to calcium, and in living muscle to the frequency of stimulation, each of which results in an increase in muscle force development at sub-maximal muscle activation. Such activators have also been shown to reduce muscle fatigue and/or to increase the overall time to fatigue in normal and low oxygenated conditions (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009; Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010). The increase in muscle force in response to nerve input has been demonstrated in healthy human volunteers as well (see, e.g., Hansen et al., "CK-2017357, a Novel Activator of Fast Skeletal Muscle, Increases Isometric Force Evoked by Electrical Stimulation of the Anterior Tibialis Muscle in Healthy Male Subjects", Society for Neuroscience 40th Annual Meeting: Neuroscience 2010, November 2010). Work in additional preclinical models of muscle function suggests that activators of the fast skeletal troponin complex also cause an increase in muscle power and/or endurance. These pharmacological properties suggest this mechanism of action could have application in conditions, for example, where neuromuscular function is impaired.

Provided are methods for enhancing fast skeletal muscle efficiency in a patient in need thereof, comprising administering to said patient an effective amount of a compound or composition described and/or disclosed herein that selectively binds the troponin complex of fast skeletal muscle fiber or sarcomere. In some embodiments, the compound disclosed and/or described herein activates fast skeletal muscle fibers or sarcomeres. In some embodiments, administration of a compound disclosed and/or described herein results in an increase in fast skeletal muscle power output. In some embodiments, administration of a compound disclosed and/or described herein results in increased sensitivity of fast skeletal muscle fibers or sarcomeres to calcium ion, as compared to fast skeletal muscle fibers or sarcomeres untreated with the compound. In some embodiments, administration of a compound disclosed and/or described herein results in a lower concentration of calcium ions causing fast skeletal muscle myosin to bind to actin. In some embodiments, administration of a compound disclosed and/or described herein results in the fast skeletal muscle fiber generating force to a greater extent at submaximal levels of muscle activation.

Also provided is a method for sensitizing a fast skeletal muscle fiber to produce force in response to a lower concentration of calcium ion, comprising contacting the fast skeletal muscle fiber with a compound or composition described and/or disclosed herein that selectively binds to troponin complexes in the fast skeletal muscle sarcomere. In some embodiments, contacting the fast skeletal muscle fiber with the compound results in activation of the fast skeletal muscle fiber at a lower calcium ion concentration than in an untreated fast skeletal muscle fiber. In some embodiments, contacting the fast skeletal muscle fiber with the compound results in the production of increased force at a lower calcium ion concentration in comparison with an untreated fast skeletal muscle fiber.

Also provided is a method for increasing time to fast skeletal muscle fatigue in a patient in need thereof, comprising contacting fast skeletal muscle fibers with a compound or composition described and/or disclosed herein that selectively binds to the troponin complexes of the fast skeletal muscle fibers. In some embodiments, the compound binds to form ligand-troponin-calcium ion complexes that activate the fast skeletal muscle fibers. In some embodiments, formation of the complexes and/or activation of the fast skeletal muscle fibers results in enhanced force and/or increased time to fatigue as compared to untreated fast skeletal muscle fibers contacted with a similar calcium ion concentration.

The compounds and pharmaceutical compositions described and/or disclosed herein are capable of modulating the contractility of the fast skeletal sarcomere in vivo, and can have application in both human and animal disease. Modulation would be desirable in a number of conditions or diseases, including, but not limited to, 1) neuromuscular disorders, such as Amyotrophic Lateral Sclerosis (ALS), Spinal Muscular Atrophy (SMA), peripheral neuropathies and myasthenia gravis; 2) disorders of voluntary muscle, including muscular dystrophies, myopathies and conditions of muscle wasting, such as sarcopenia and cachexia syndromes (e.g., cachexia syndromes caused by diseases such as cancer, heart failure, chronic obstructive pulmonary disease (COPD), and chronic kidney disease/dialysis), and rehabilitation-related deficits, such as those associated with recovery from surgery (e.g. post-surgical muscle weakness) prolonged bed rest or stroke rehabilitation; 3) central nervous system (CNS) disorders in which muscle weakness, atrophy and fatigue are prominent symptoms, such as multiple sclerosis, Parkinson's disease, stroke and spinal cord injury; and 4) muscle symptoms stemming from systemic disorders, including Peripheral Vascular Disease (PVD) or Peripheral Arterial Disease (PAD) (e.g., claudication), metabolic syndrome, chronic fatigue syndrome, obesity and frailty due to aging.

The compounds and compositions described and/or disclosed herein may be used to treat neuromuscular diseases, i.e., diseases that affect any part of the nerve-muscle unit. Neuromuscular diseases include, for example: 1) diseases of the motor unit, including but not limited to Amyotrophic Lateral Sclerosis (ALS) including bulbar and primary lateral sclerosis (PLS) variants; spinal muscular atrophy types 1-4; Kennedy syndrome; post-polio syndrome; motor neuropathies including, for example, critical illness polyneuropathy; multifocal motor neuropathy with conduction block; Charcot-Marie-Tooth disease and other hereditary motor and sensory neuropathies; and Guillain-Barre Syndrome, 2) disorders of the neuromuscular junction, including myasthenia gravis, Lambert-Eaton myasthenic syndrome, and prolonged neuromuscular blockade due to drugs or toxins; and 3) peripheral neuropathies, such as acute inflammatory demyelinating polyradiculoneuropathy, diabetic neuropathy, chronic inflammatory demyelinating polyradiculoneuropathy, traumatic peripheral nerve lesions, neuropathy of leprosy, vasculitic neuropathy, dermatomyositis/polymyositis and neuropathy of Friedreich Ataxia.

The compounds and compositions described and/or disclosed herein may be used to treat disorders of voluntary muscle. Disorders of voluntary muscle include 1) muscular dystrophies (including, for example, Duchenne, Becker, Limb-Girdle, Facioscapulohumeral, limb girdle, Emery-Dreyfus, oculopharyngeal and congenital muscular dystrophies); and 2) myopathies, such as nemaline myopathy, central core disease, congenital myopathies, mitochondrial myopathies, acute myopathy; inflammatory myopathies (such as dermatomyositis/polymyositis and inclusion body myositis), endocrine myopathies (such as those associated with hyper- or hypothyroidism), Cushing's or Addison's syndrome or disease and pituitary gland disorders, metabolic myopathies (such as glycogen storage diseases, e.g., McArdle's disease, Pompe disese, etc), drug-induced myopathy (statins, ant-retroviral drugs, steroid myopathy) restrictive lung disease, sarcoidosis, Schwartz-Jampel Syndrome, focal muscular atrophies, and distal myopathies.

The compounds and compositions described and/or disclosed herein may be used to treat or Amyotrophic Lateral Sclerosis (ALS). ALS is a disease that generally arises later in life (Age 50+) and has a rapid progression from initial limb weakness to paralysis and death. Common life expectancy after diagnosis is 3-5 years. The cause of disease for most ALS patients is unknown (termed the spontaneous form) while a small proportion of patients have an inherited form (familial) of disease. The condition causes progressive death of motor neurons through causes that are not clear. Surviving motor units attempt to compensate for dying ones by innervating more fibers (termed sprouting) but this can only partially correct muscle function, as muscles are subsequently more prone to problems of coordination and fatigue. Eventually, surviving motor neurons die, resulting in complete paralysis of the affected muscle. The disease is commonly fatal through the eventual loss of innervation to the diaphragm, resulting in respiratory failure. Current treatment options for ALS are limited.

The compounds and compositions described and/or disclosed herein may be used to treat Spinal Muscular Atrophy (SMA). SMA is a genetic disorder that arises through the mutation of a protein, SMN1, that appears to be required for the survival and health of motor neurons. The disease is most common in children as the majority of patients only survive until 11-12 years of age. There is currently no available treatment for SMA.

The compounds and compositions described and/or disclosed herein may be used to treat myasthenia gravis. Myasthenia gravis is a chronic autoimmune neuromuscular disease wherein the body produces antibodies that block, alter, or destroy proteins involved in signaling at the neuromuscular junction, thus preventing muscle contraction from occurring. These proteins include nicotinic acetylcholine receptor (AChR) or, less frequently, a muscle-specific tyrosine kinase (MuSK) involved in AChR clustering (see, e.g., Drachman, N. Eng. J. of Med., 330:1797-1810, 1994). The disease is characterized by varying degrees of weakness of the skeletal (voluntary) muscles of the body. The hallmark of myasthenia gravis is muscle weakness that increases during periods of activity and improves after periods of rest. Although myasthenia gravis may affect any voluntary muscle, certain muscles, such as those that control eye and eyelid movement, facial expression, chewing, talking, and swallowing are often, but not always, involved in the disorder. The muscles that control breathing and neck and limb movements may also be affected. In most cases, the first noticeable symptom is weakness of the eye muscles. In others, difficulty in swallowing and slurred speech may be the first signs. The degree of muscle weakness involved in myasthenia gravis varies greatly among patients, ranging from a localized form, limited to eye muscles (ocular myasthenia), to a severe or generalized form in which many muscles—sometimes including those that control breathing—are affected. Symptoms, which vary in type and severity, may include a drooping of one or both eyelids (ptosis), blurred or double vision (diplopia) due to weakness of the muscles that control eye movements, unstable or waddling gait, weakness in arms, hands, fingers, legs, and neck, a change in facial expression, difficulty in swallowing and shortness of breath, and impaired speech (dysarthria). Generalized weakness develops in approximately 85% of patients.

The compounds and compositions described and/or disclosed herein may be used to treat sarcopenia, e.g., sarcopenia associated with aging or disease (e.g. HIV infection). Sarcopenia is characterized by a loss of skeletal muscle mass, quality, and strength. Clinically, a decline in skeletal muscle tissue mass (muscle atrophy) contributes to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. The changes in overall adiposity and fat distribution appear to be important factors in many common age-related diseases such as hypertension, glucose intolerance and diabetes, dyslipidemia, and atherosclerotic cardiovascular disease. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality.

The compounds and compositions described and/or disclosed herein may be used to treat cachexia. Cachexia is a state often associated with cancer or other serious diseases or conditions, (e.g, chronic obstructive pulmonary disease, heart failure, chronic kidney disease, kidney dialysis), that is characterized by progressive weight loss, muscle atrophy and fatigue, due to the deletion of adipose tissue and skeletal muscle.

The compounds and compositions described and/or disclosed herein may be used to treat muscular dystrophies. Muscular dystrophy can be characterized by progressive muscle weakness, destruction and regeneration of the muscle fibers, and eventual replacement of the muscle fibers by fibrous and fatty connective tissue.

The compounds and compositions described and/or disclosed herein may be used to treat post-surgical muscle weakness, which is a reduction in the strength of one or more muscles following surgical procedure. Weakness may be generalized (i.e. total body weakness) or localized to a specific area, side of the body, limb, or muscle.

The compounds and compositions described and/or disclosed herein may be used to treat post-traumatic muscle weakness, which is a reduction in the strength of one or more muscles following a traumatic episode (e.g. bodily injury). Weakness may be generalized (i.e. total body weakness) or localized to a specific area, side of the body, limb, or muscle.

The compounds and compositions described and/or disclosed herein may be used to treat muscle weakness and fatigue produced by peripheral vascular disease (PVD) or peripheral artery disease (PAD). Peripheral vascular disease is a disease or disorder of the circulatory system outside of the brain and heart. Peripheral artery disease (PAD), also known as peripheral artery occlusive disease (PAOD), is a form of PVD in which there is partial or total blockage of an artery, usually one leading to a leg or arm. PVD and/or PAD can result from, for example, atherosclerosis, inflammatory processes leading to stenosis, embolus/thrombus formation, or damage to blood vessels due to disease (e.g., diabetes), infection or injury. PVD and/or PAD can cause either acute or chronic ischemia, typically of the legs. The symptoms of PVD and/or PAD include pain, weakness, numbness, or cramping in muscles due to decreased blood flow (claudication), muscle pain, ache, cramp, numbness or fatigue that occurs during exercise and is relieved by a short period of rest (intermittent claudication), pain while resting (rest pain) and biological tissue loss (gangrene). The symptoms of PVD and/or PAD often occur in calf muscles, but symptoms may also be observed in other muscles such as the thigh or hip. Risk factors for PVD and/or PAD include age, obesity, sedentary lifestyle, smoking, diabetes, high blood pressure, and high cholesterol (i.e., high LDL, and/or high triglycerides and/or low HDL). People who have coronary heart disease or a history of heart attack or stroke generally also have an increased frequency of having PVD and/or PAD. Activators of the fast skeletal troponin complex have been shown to reduce muscle fatigue and/or to increase the overall time to fatigue in in vitro and in situ models of vascular insufficiency (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009; Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010).

The compounds and compositions described and/or disclosed herein may be used to treat symptoms of frailty, e.g., frailty associated with aging. Frailty is characterized by one or more of unintentional weight loss, muscle weakness, slow walking speed, exhaustion, and low physical activity.

The compounds and compositions described and/or disclosed herein may be used to treat muscle weakness and/or fatigue due to wasting syndrome, which is a condition characterized by involuntary weight loss associated with chronic fever and diarrhea. In some instances, patients with wasting syndrome lose 10% of baseline body weight within one month.

The compounds and compositions described and/or disclosed herein may be used to treat muscular diseases and conditions caused by structural and/or functional abnormalities of skeletal muscle tissue, including muscular dystrophies, congenital muscular dystrophies, congenital myopathies, distal myopathies, other myopathies (e.g., myofibrillar, inclusion body), myotonic syndromes, ion channel muscle diseases, malignant hyperthermias, metabolic myopathies, congenital myasthenic syndromes, sarcopenia, muscle atrophy and cachexia.

The compounds and compositions described and/or disclosed herein also may be used to treat diseases and conditions caused by muscle dysfunction originating from neuronal dysfunction or transmission, including amyotrophic lateral sclerosis, spinal muscular atrophies, hereditary ataxias, hereditary motor and sensory neuropathies, hereditary paraplegias, stroke, multiple sclerosis, brain injuries with motor deficits, spinal cord injuries, Alzheimer's disease, Parkinson's disease with motor deficits, myasthenia gravis and Lambert-Eaton syndrome.

The compounds and compositions described and/or disclosed herein also may be used to treat diseases and conditions caused by CNS, spinal cord or muscle dysfunction originating from endocrine and/or metabolic dysregulation, including claudication secondary to peripheral artery disease, hypothyroidism, hyper- or hypo-parathyroidism, diabetes, adrenal dysfunction, pituitary dysfunction and acid/base imbalances.

The compounds and compositions described and/or disclosed herein may be administered alone or in combination with other therapies and/or therapeutic agents useful in the treatment of the aforementioned disorders.

The compounds and compositions described and/or disclosed herein may be combined with one or more other therapies to treat ALS. Examples of suitable therapies include riluzole, baclofen, diazepam, trihexyphenidyl and amitriptyline. In some embodiments, the compounds and compositions described and/or disclosed herein are combined with riluzole to treat a subject suffering from ALS.

The compounds and compositions described and/or disclosed herein may be combined with one or more other therapies to treat myasthenia gravis. Examples of suitable therapies include administration of anticholinesterase agents (e.g., neostigmine, pyridostigmine), which help improve neuromuscular transmission and increase muscle strength; administration of immunosuppressive drugs (e.g., prednisone, cyclosporine, azathioprine, mycophenolate mofetil) which improve muscle strength by suppressing the production of abnormal antibodies; thymectomy (i.e., the surgical removal of the thymus gland, which often is abnormal in myasthenia gravis patients); plasmapheresis; and intravenous immune globulin.

The compounds and compositions described and/or disclosed herein may be combined with one or more other therapies to treat PVD or PAD (e.g., claudication). Treatment of PVD and PAD is generally directed to increasing arterial blood flow, such as by smoking cessation, controlling blood pressure, controlling diabetes, and exercising. Treatment can also include medication, such as medicines to help improve walking distance (e.g., cilostazol, pentoxifylline), antiplatelet agents (e.g., aspirin, ticlopidine, clopidogrel), anticoagulents (e.g., heparin, low molecular weight heparin, warfarin, enoxaparin) thrombolytics, antihypertensive agents (e.g., diuretics, ACE inhibitors, calcium channel blockers, beta blockers, angiotensin II receptor antagonists), and cholesterol-lowering agents (e.g., statins). In some patients, angioplasty, stenting, or surgery (e.g., bypass surgery or surgery to remove an atherosclerotic plaque) may be necessary.

Suitable therapeutic agents include, for example, anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents.

Suitable additional therapeutic agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, testosterone, insulin-derived growth factor, human growth hormone, riluzole, cannabidiol, prednisone, albuterol, non-steroidal anti-inflammatory drugs, and botulinum toxin.

Other suitable therapeutic agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890, growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 (Lilly), MK-677 (Merck), CP424391 (Pfizer) and B-HT920, growth hormone releasing factor and its analogs, growth hormone and its analogs and somatomedins including IGF-1 and IGF-2, alpha-adrenergic agonists, such as clonidine or serotonin $5-HT_D$ agonists, such as sumatriptan, agents which inhibit somatostatin or its release, such as physostigmine, pyridostigmine, parathyroid hormone, PTH(1-34), and bisphosphonates, such as MK-217 (alendronate).

Still other suitable therapeutic agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Other suitable therapeutic agents include anabolic agents, such as selective androgen receptor modulators (SARMs); antagonists of the activin receptor pathway, such as antimyostatin antibodies or soluble activin receptor decoys, including ACE-031 (Acceleron Pharmaceuticals, a soluble activin receptor type IIB antagonist), MYO-027/PFE-3446879 (Wyeth/Pfizer, an antibody myostatin inhibitor), AMG-745 (Amgen, a peptibody myostatin inhibitor), and an ActRIIB decoy receptor (see Zhou et al., Cell, 142, 531-543, Aug. 20, 2010); and anabolic steroids.

Still other suitable therapeutic agents include aP2 inhibitors, such as those disclosed in U.S. Pat. No. 6,548,529, PPAR gamma antagonists, PPAR delta agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable therapeutic agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable therapeutic agents include antiresorptive agents, hormone replacement therapies, vitamin D analogues, elemental calcium and calcium supplements, cathepsin K inhibitors, MMP inhibitors, vitronectin receptor antagonists, Src SH.sub.2 antagonists, vacuolar $H^+$-ATPase inhibitors, ipriflavone, fluoride, Tibo lone, pro stanoids, 17-beta hydroxysteroid dehydrogenase inhibitors and Src kinase inhibitors.

The above therapeutic agents, when employed in combination with the compounds and compositions disclosed and/or described herein, may be used, for example, in those amounts indicated in the Physicians' Desk Reference (PDR) or as otherwise determined by one of ordinary skill in the art.

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.05 to 100 mg/kg of body weight; in some embodiments, from about 0.10 to 10.0 mg/kg of body weight, and in some embodiments, from about 0.15 to 1.0 mg/kg of body weight. Thus, for administration to a 70 kg person, in some embodiments, the dosage range would be about from 3.5 to 7000 mg per day; in some embodiments, about from 7.0 to 700.0 mg per day, and in some embodiments, about from 10.0 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 70 mg to about 700 mg per day, and an exemplary intravenous administration dosage is from about 70 mg to about 700 mg per day, each depending upon the compound pharmacokinetics.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pa.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

The following examples serve to more fully describe the invention described herein. It is understood that these examples in no way serve to limit the true scope of this invention, but rather are presented for illustrative purposes.

EXAMPLE 1

(S)-2-(4-Fluorophenyl)propan-1-amine

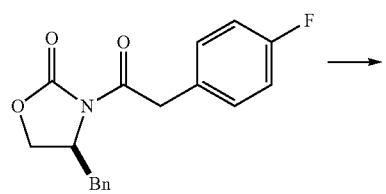

(S)-4-Benzyl-3-(2-(4-fluorophenyl)acetyl)oxazolidin-2-one

To a cooled (−78° C.) solution of (S)-4-benzyloxazolidin-2-one (10 g, 58 mmol, 1.0 equiv) in 100 mL THF was added dropwise n-BuLi (40 mL, 1.6 M in hexanes, 64 mmol, 1.1 equiv). After stirring for 30 minutes, 4-fluorophenylacetyl chloride (10 g, 0.58 mmol, 1.0 equiv) was added dropwise. After stirring for an additional 30 minutes, the reaction mixture was allowed to warm to room temperature. The reaction was quenched with saturated aq. NH$_4$Cl, extracted with dichloromethane, and washed with brine. The organic layer was then dried over sodium sulfate, filtered, and concentrated in vacuo. Purification by silica gel (10-20% EtOAc/hexanes) provided the title compound as a thick oil (14.7 g, 81%).

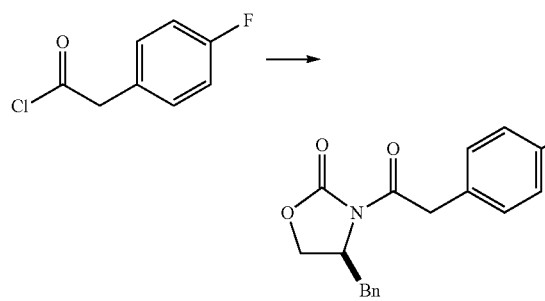

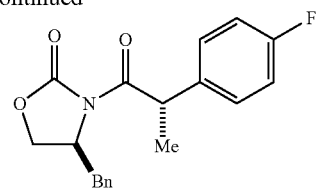

(S)-4-Benzyl-3-((S)-2-(4-fluorophenyl)propanoyl)oxazolidin-2-one

To a room-temperature solution of (S)-4-Benzyl-3-(2-(4-fluorophenyl)acetyl)oxazolidin-2-one (5.1 g, 16.3 mmol, 1.0 equiv) in dry THF (100 mL) was added iodomethane (1.0 mL, 16.2 mmol, 1.0 equiv) by syringe. The resulting mixture was cooled to −78° C., and NaHMDS (8.15 mL, 2M in THF, 16.3 mmol, 1.0 equiv) was added dropwise by syringe. After stirring for 15 minutes at −78° C., the reaction mixture was allowed to warm to room temperature. The reaction was quenched with saturated. aq. NH$_4$Cl, and diluted with EtOAc. The organic layer was washed with brine, dried over Na$_2$SO$_4$, filtered and concentrated in vacuo. Purification by silica gel chromatography (7-20% EtOAc/hexanes) provided the title compound (2.6 g, 49%).

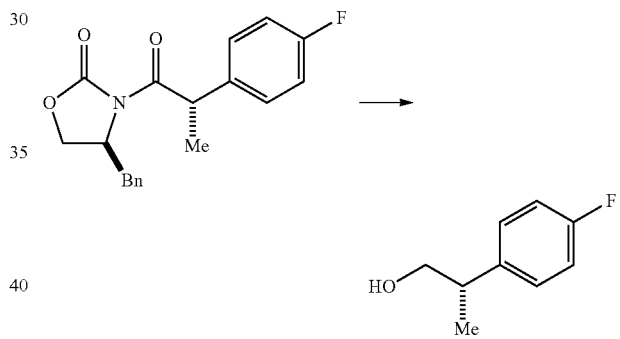

(S)-2-(4-Fluorophenyl)propan-1-ol

To a room-temperature solution of (S)-4-benzyl-3-((S)-2-(4-fluorophenyl)propanoyl)oxazolidin-2-one (1.8 g, 5.5 mmol, 1.0 equiv) in THF (18 mL) was added a solution of NaBH$_4$ (1.0 g, 26.4 mmol, 4.8 equiv) in water (6.0 mL). The reaction mixture was stirred for 3 h at room temperature and then quenched by the careful addition of aq. 1 M HCl. The reaction mixture was diluted with water and ethyl acetate. The layers were separated and the organic layer was subsequently washed with brine, dried over Na$_2$SO$_4$, filtered and concentrated in vacuo. Purification by silica gel chromatography (10-75% EtOAc/Hexanes) provided the title compound (0.824 g, 97%).

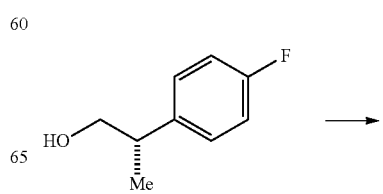

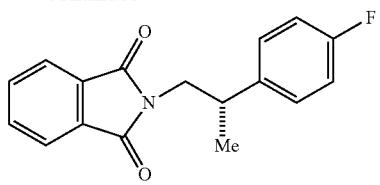

(S)-2-(2-(4-Fluorophenyl)propyl)isoindoline-1,3-dione

To a solution of (S)-2-(4-fluorophenyl)propan-1-ol (0.82 g, 5.35 mmol, 1.0 equiv), phthalimide (0.82 g, 5.6 mmol, 1.05 equiv), and triphenyl phosphine (2.1 g, 8.03 mmol, 1.5 equiv) in dry THF (18 mL) was added dropwise diethylazodicarboxylate (3.6 mL, 15% in toluene, 8.0 mmol, 1.5 equiv). The reaction mixture was stirred over 72 h and then concentrated in vacuo. Purification by silica gel chromatography (15-25% EtOAc/Hexanes) provided the title compound (0.9 g, 59%).

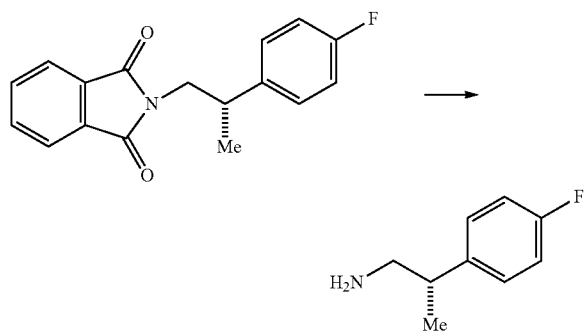

(S)-2-(4-Fluorophenyl)propan-1-amine

To a room-temperature solution of (S)-2-(2-(4-fluorophenyl)propyl)isoindoline-1,3-dione (900 mg, 3.2 mmol, 1.0 equiv) in toluene (14 mL) was added hydrazine hydrate (1.4 mL, 45 mmol, 14 equiv) by syringe. The resulting mixture was heated to 80° C. for 30 minutes and then cooled to room temperature. The resulting solution was decanted from the solid in the reaction mixture, and the solid was washed with additional toluene. The combined organic layers were combined and concentrated in vacuo to provide the title compound (491 mg, 99%), which was used without further purification.

EXAMPLE 2

2-(4-Fluorophenyl)-2-methylpropan-1-amine

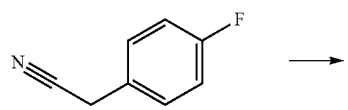

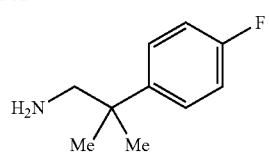

To a solution of 4-fluorophenylacetonitrile (50 g, 370 mmol, 1.0 equiv) and iodomethane (70 mL, 1.1 mol, 3 equiv) in THF (370 mL) was added KOt-Bu (124 g, 1.1 mol, 3 equiv) as a solid in portions such that the reaction mixture did not exceed 50° C. The reaction mixture was stirred overnight and then quenched by the addition of brine. The mixture was diluted with EtOAc and washed twice with brine. The organic layer was dried over $Na_2SO_4$, filtered, and concentrated in vacuo to provide 2-(4-fluorophenyl)-2-methylpropanenitrile as a yellow oil (57 g, 94%), which was used without further purification in the next step. To a solution of the nitrile in dry THF (800 mL) was added a solution of lithium aluminum hydride (210 mL, 2 M in ether, 420 mmol, 1.2 equiv). After the mixture was heated at reflux overnight, the reaction was allowed to cool to room temperature, and a Fieser and Fieser work-up (300 uL water/mmol, 1.0 mL 3N NaOH/mmol, 300 uL water/mmol) was performed. Filtration of the resulting solids provided the title compound as an orange oil (57 g, 92%).

EXAMPLE 3

(1-(4-Fluorophenyl)cyclobutyl)methanamine

A solution of 4-fluorophenylacetonitrile (6.7 g, 75 mmol, 1.5 equiv), 1,3-dibromopropane (10 mL, 50 mmol, 1 equiv), KOH (27 g, 150 mmol, 3.0 equiv), and tetrabutylammonium bromide (100 mg) in toluene (135 mL) was heated to 100° C. for 3 hours. The organic layer was separated and concentrated to dryness. Silica gel chromatography using a gradient of 0-30% EtOAc/hexanes resulted in partially purified product which was further purified by Kugelrohr distillation at 200° C. to provide 3.76 g (22 mmol) of the intermediate nitrile product as an oil. The residue was dissolved in dry THF (22 mL) and treated with a solution of lithium aluminum hydride (27 mL, 2 M in ether, 55 mmol, 2.5 equiv). The mixture was stirred at 0° C. for 2 hours followed by a Fieser and Fieser work-up (38 uL water/mmol, 118 uL 3N NaOH/mmol, 38 uL water/mmol). The organic layer was concentrated to dryness to provide the desired product (3.6 g, 40% overall) as a yellow oil.

EXAMPLE 4

(1-(6-Methoxypyridin-2-yl)cyclobutyl)methanamine

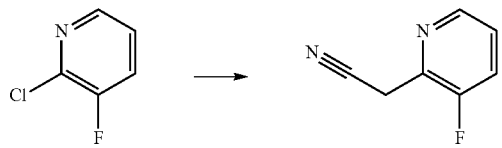 [SMILES: Fc1cccnc1Cl ; N#CCc1ncccc1F]

2-(3-Fluoropyridin-2-yl)acetonitrile

To a 0° C. solution of 2-chloro-3-fluoropyridine (3.0 g, 23 mmol, 1.0 equiv) and acetonitrile (1.3 mL, 25 mmol, 1.1 equiv) in toluene (50 mL) was added sodium hexamethyldisilazide (NaHMDS) (2.0 M in THF, 13 mL, 25 mmol, 1.1 equiv). The resulting mixture was stirred for 2 hours at 0° C. and then partitioned between EtOAc and water. The aqueous layer was extracted with EtOAc and the combined organic phases were washed with saturated NaCl, dried over Na$_2$SO$_4$ and concentrated in vacuo to provide the crude desired product as an oil which was used without further purification.

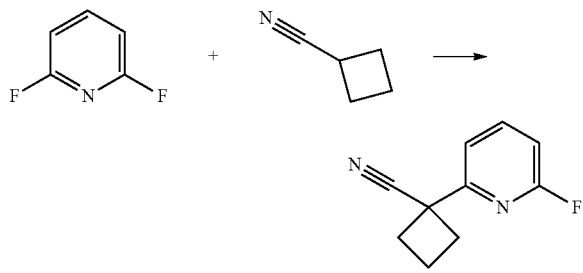

1-(6-Fluoropyridin-2-yl)cyclobutanecarbonitrile

Following the same procedure as above for 2-(3-fluoropyridin-2-yl)acetonitrile with 2,6-difluoropyridine (5.0 g, 43 mmol, 1.0 equiv), cyclobutylcarbonitrile (3.5 g, 43 mmol, 1.0 equiv) and NaHMDS (2.0 M in THF, 24 mL, 47 mmol, 1.1 equiv) in toluene (100 mL) gave the desired product (4.9 g, 64%) as a colorless oil following purification over silica gel using 25% EtOAc/hexanes as eluent.

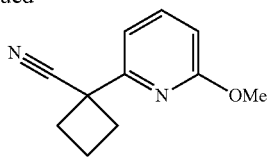

1-(6-Methoxypyridin-2-yl)cyclobutanecarbonitrile

To stirred 6.0 mL of anhydrous methanol at 0° C. under nitrogen was added sodium metal (~1 g) and the mixture stirred for 30 minutes. To this was added 1-(6-fluoropyridin-2-yl)cyclobutanecarbonitrile (1.6 g, 9.1 mmol, 1.0 equiv) and the resulting mixture heated to 75° C. for 45 minutes. The solution was cooled to room temperature and partitioned between water and EtOAc. The layers were separated, the aqueous phase was extracted with EtOAc, and the combined organic phases were washed with saturated NaCl, dried over Na$_2$SO$_4$ and concentrated in vacuo to give the desired product (1.7 g, 97%) as a colorless oil.

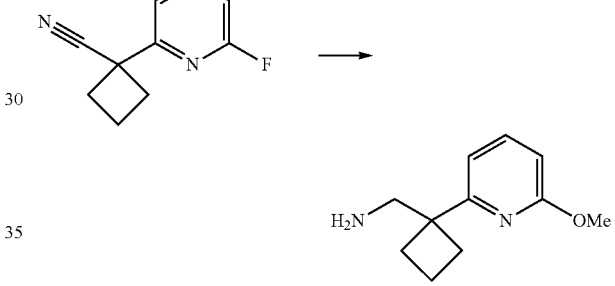

(1-(6-Methoxypyridin-2-yl)cyclobutyl)methanamine

To a stirred solution of 1-(6-methoxypyridin-2-yl)cyclobutanecarbonitrile (1.7 g, 8.8 mmol, 1.0 equiv) in THF (20 mL) was added lithium aluminum hydride solution (1.0 M in THF, 11 mL, 11 mmol, 1.1 equiv). The mixture was refluxed for 1.5 hours and allowed to cool to room temperature. Water (0.43 mL) was added slowly followed by 0.43 mL of 3 M NaOH and then three additions of 0.43 mL of water (Fieser and Fieser workup). The resulting mixture was filtered through diatomaceous earth and rinsed with THF. The combined organics were dried over Na$_2$SO$_4$ and concentrated to dryness to give the desired product (1.6 g, 97%) as a viscous oil.

EXAMPLE 5

1-(3-Fluoropyridin-2-yl)cyclobutanamine

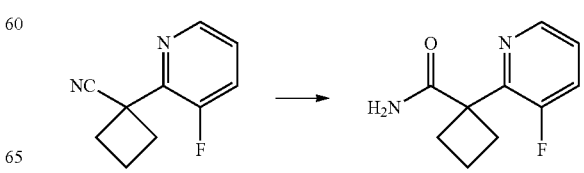

1-(3-Fluoropyridin-2-yl)cyclobutanecarboxamide

To a 250 mL round bottom flask containing DMSO (60 mL), 1-(3-fluoropyridin-2-yl)cyclobutanecarbonitrile (2.96 g, 16.8 mmol, 1.0 equiv) was added and the mixture was stirred until homogenous. Potassium carbonate (7.0 g, 50.4 mmol, 3.0 equiv) was then added and the reaction mixture was cooled to 0° C., followed by the addition of 35% hydrogen peroxide (6.5 mL). The reaction was stirred at 0° C. for 30 min and then warmed to room temperature. At this time, the reaction was diluted with water (50 mL) and ethyl acetate (100 mL). After transferring to a separatory funnel and shaking, the organic layer was separated from the aqueous layer and then washed with brine (3×50 mL). The organic layer was then dried over $Na_2SO_4$, filtered, and concentrated to give a crude solid that was purified by silica gel chromatography (10% EtOAC/hexanes) to afford 1.92 g (59%) of 1-(3-fluoropyridin-2-yl)cyclobutanecarboxamide as a white solid.

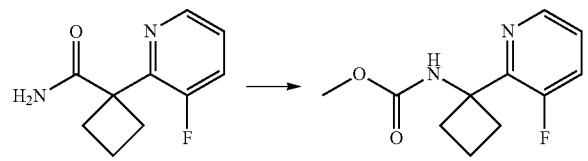 [SMILES: NC(=O)C1(c2ncccc2F)CCC1 ; COC(=O)NC1(c2ncccc2F)CCC1]

Methyl 1-(3-fluoropyridin-2-yl)cyclobutylcarbamate 1-(3-fluoropyridin-2-yl)cyclobutanecarboxamide (1.92 g, 9.88 mmol, 1.0 equiv) was dissolved in methanol (20 mL) and potassium hydroxide (1.11 g, 19.8 mmol, 2.0 equiv) was added. The mixture was sonicated until homogeneous, followed by the addition of iodosobenzene diacetate (4.77 g, 14.8 mmol, 1.5 equiv). The reaction was stirred for 20 min and then diluted with water (100 mL) and ethyl acetate (125 mL). After transferring to a separatory funnel and shaking, the organic layer was separated from the aqueous layer, and the aqueous layer was extracted with EtOAc (50 mL). The combined organic layers were then dried over $Na_2SO_4$, filtered, and concentrated to give a crude oil that was purified by silica gel chromatography (40% EtOAC/hexanes) to afford 1.47 g (67%) of methyl 1-(3-fluoropyridin-2-yl)cyclobutylcarbamate as a white solid.

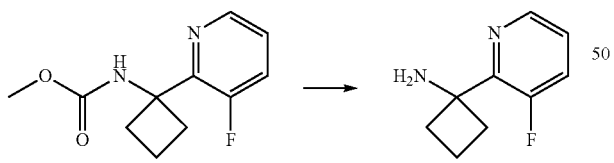

1-(3-Fluoropyridin-2-yl)cyclobutanamine

To a 20 mL microwave reaction vial was added methyl 1-(3-fluoropyridin-2-yl)cyclobutylcarbamate (1.47 g, 6.56 mmol, 1.0 equiv), ethanol (12 mL) and 3N aqueous sodium hydroxide (7 mL). The reaction mixture was heated in the microwave reactor at 150° C. for 30 min. The ethanol was evaporated under reduced pressure and the mixture was extracted with ethyl acetate (30 mL). The aqueous layer was then extracted with ethyl acetate (2×30 mL). The organic layers were combined, dried over $Na_2SO_4$, filtered, and concentrated to give 1-(3-fluoropyridin-2-yl)cyclobutanamine (1.01 g, 93%) as a crude yellow oil that was used without further purification.

EXAMPLE 6

N-(2-(4-Fluorophenyl)-2-methylpropyl)-6-(2-methylprop-1-enyl)pyridin-2-amine

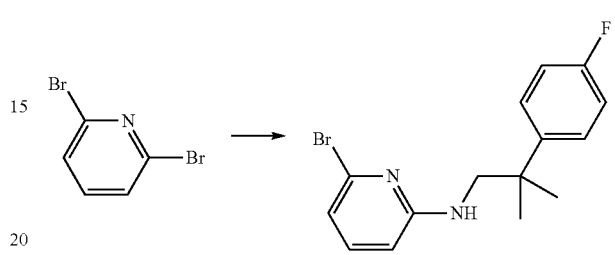

6-Bromo-N-(2-(4-fluorophenyl)-2-methylpropyl)pyridin-2-amine

To a 5 mL microwave reaction vial was added 2,6-dibromopyridine (1.25 g, 5.0 mmol, 1.0 equiv), 2-(4-fluorophenyl)-2-methylpropan-1-amine (1.06 g, 6 mmol, 1.2 equiv), DIPEA (1.9 mL, 11.0 mmol, 2.2 equiv), and acetonitrile (5 mL). The vial was sealed and heated in an oil bath at 137° C. for 48 h, concentrated, and purified by silica gel column chromatography to give 220 mg (14%) of 6-bromo-N-(2-(4-fluorophenyl)-2-methylpropyl)pyridin-2-amine as a white solid (m/z [M+H]=323).

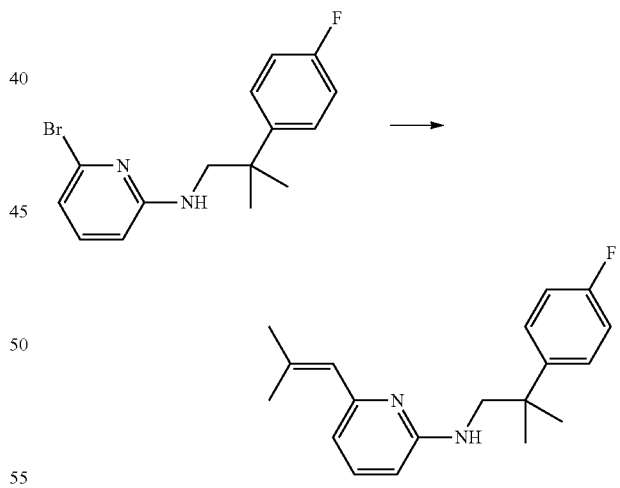

N-(2-(4-Fluorophenyl)-2-methylpropyl)-6-(2-methylprop-1-enyl)pyridin-2-amine To a 5 mL microwave reaction vessel was added 6-bromo-N-(2-(4-fluorophenyl)-2-methylpropyl)pyridin-2-amine (220 mg, 0.7 mmol, 1.0 equiv), 2-methylprop-1-enylboronic acid (100 mg, 1 mmol, 1.5 equiv), $Cl_2Pd(dppf)$ (50 mg, 70 μmol, 0.1 equiv), potassium carbonate (300 mg, 2.1 mmol, 3.0 equiv), dioxane (4 mL), and water (1 mL). The reaction was heated in a microwave reactor at 135° C. for 35 min and then diluted with saturated sodium bicarbonate (20 mL) and extracted with ethyl acetate (50 mL). The organic layer was then dried over Na₂SO₄, filtered, and concentrated to give a crude solid that was purified by reverse phase column chromatography to afford 14 mg of N-(2-(4-fluorophenyl)-2-methylpropyl)-6-(2-methylprop-1-enyl)pyridin-2-amine (m/z [M+H]=299.4).

EXAMPLE 7

4-Phenyl-N-(1-phenylcyclobutyl)pyridin-2-amine

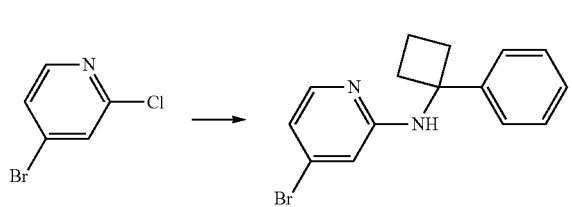 [SMILES: Clc1cc(Br)ccn1 ; Brc1ccnc(NC2(c3ccccc3)CCC2)c1]

4-Bromo-N-(1-phenylcyclobutyl)pyridin-2-amine

To a 20 dram vial was added 4-bromo-2-chloropyridine (250 mg, 5.0 mmol, 1.0 equiv), 1-phenylcyclobutanamine (1.0 g, 7 mmol, 1.4 equiv), and NMP (1 mL). The reaction was heated to 120° C., stirred for 72 h, and then diluted with water (20 mL) and ethyl acetate (50 mL). After transferring to a separatory funnel and shaking, the organic layer was separated from the aqueous layer. The organic layer was then dried over Na₂SO₄, filtered, and concentrated to give a crude solid that was purified by silica gel column chromatography, affording 139 mg (9%) of 4-bromo-N-(1-phenylcyclobutyl) pyridin-2-amine as an orange solid.

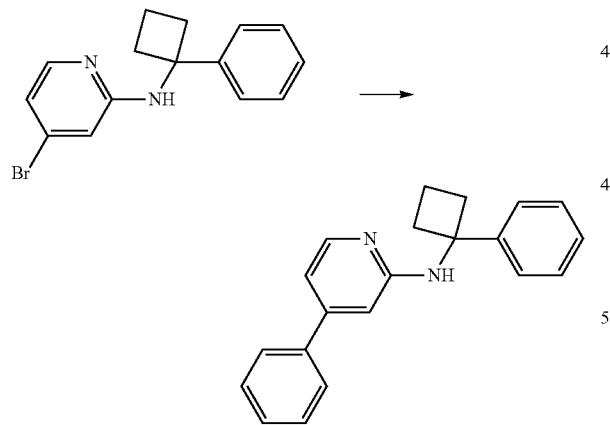

4-Phenyl-N-(1-phenylcyclobutyl)pyridin-2-amine

To a 3 mL microwave reaction vessel was added 4-bromo-N-(1-phenylcyclobutyl)pyridin-2-amine (50 mg, 165 μmol, 1.0 equiv), phenylboronic acid (30 mg, 248 μmol, 1.5 equiv), Cl₂Pd(dppf) (12 mg, 16 μmol, 0.1 equiv), potassium carbonate (57 mg, 413 μmol, 2.5 equiv), dioxane (750 μL), and water (250 μL). The reaction was heated in a microwave reactor at 140° C. for 20 min and then diluted with saturated sodium bicarbonate (20 mL) and extracted with ethyl acetate (50 mL). The organic layer was then dried over Na₂SO₄, filtered, and concentrated to give a crude solid that was purified by reverse phase column chromatography to afford 9 mg of 4-phenyl-N-(1-phenylcyclobutyl)pyridin-2-amine (m/z [M+H]=301.2).

EXAMPLE 8

5-Phenyl-N-(1-phenylcyclobutyl)pyridin-2-amine

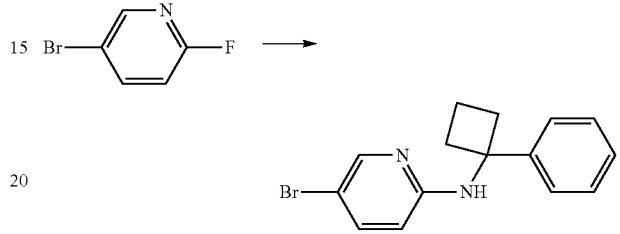

5-Bromo-N-(1-phenylcyclobutyl)pyridin-2-amine

To a 20 dram vial was added 5-bromo-2-fluoropyridine (250 mg, 5.0 mmol, 1.0 equiv), 1-phenylcyclobutanamine (1.0 g, 7 mmol, 1.4 equiv), and NMP (1 mL). The reaction was heated to 120° C., stirred for 72 h, and then diluted with water (20 mL) and extracted with ethyl acetate (50 mL). The organic layer was then dried over Na₂SO₄, filtered, and concentrated to give a crude solid that was purified by silica gel column chromatography to give 102 mg (26%) of 5-bromo-N-(1-phenylcyclobutyl)pyridin-2-amine as a pale yellow solid.

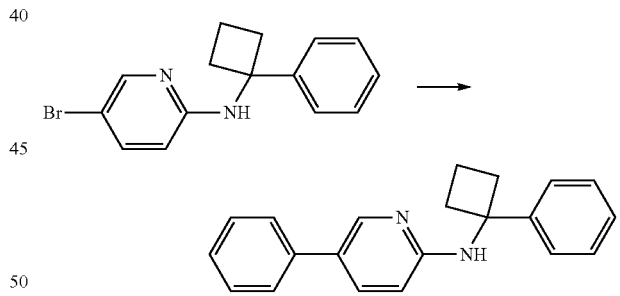

5-Phenyl-N-(1-phenylcyclobutyl)pyridin-2-amine

To a 3 mL microwave reaction vessel was added 5-bromo-N-(1-phenylcyclobutyl)pyridin-2-amine (102 mg, 340 μmol, 1.0 equiv), phenylboronic acid (59 mg, 505 μmol, 1.5 equiv), Cl₂Pd(dppf) (25 mg, 34 μmol, 0.1 equiv), potassium carbonate (116 mg, 842 μmol, 2.5 equiv), dioxane (1 mL) and water (500 μL). The reaction was heated in a microwave reactor at 140° C. for 20 min and then diluted with saturated sodium bicarbonate (20 mL) and extracted with ethyl acetate (50 mL). The organic layer was then dried over Na₂SO₄, filtered, and concentrated to give a crude solid that was purified by silica gel column chromatography (10% EtOAc/hexanes), affording 27 mg of 5-phenyl-N-(1-phenylcyclobutyl)pyridin-2-amine as a white solid (m/z [M+H]=301.2).

EXAMPLE 9

1-(6-(2-(4-Fluorophenyl)-2-methylpropylamino)pyridin-3-yl)ethane-1,2-diol

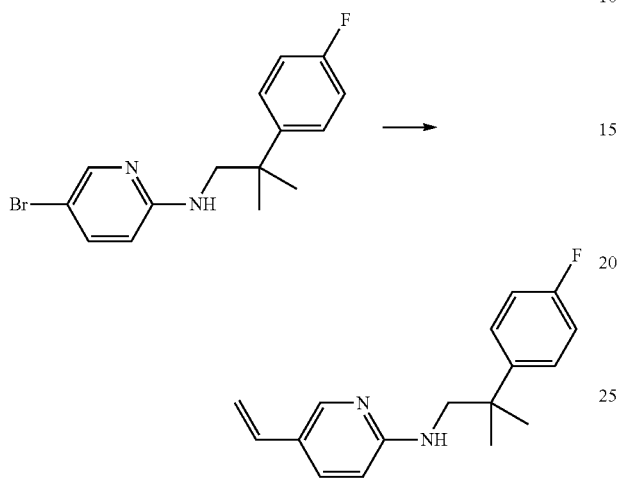

N-(2-(4-Fluorophenyl)-2-methylpropyl)-5-vinylpyridin-2-amine

To a 5 mL microwave reaction vessel was added 5-bromo-N-(2-(4-fluorophenyl)-2-methylpropyl)pyrimidin-2-amine (255 mg, 0.8 mmol, 1.0 equiv), 2,4,6-trivinyl-1,3,5,2,4,6-trioxatriborinane (285 mg, 1.2 mmol, 1.5 equiv), Cl$_2$Pd(dppf) (58 mg, 79 µmol, 0.1 equiv), potassium carbonate (1.2 mL of a 2N aqueous solution, 2.4 mmol, 3.0 equiv), and dioxane (4 mL). The reaction was heated in a microwave reactor at 115° C. for 20 min. The aqueous layer was removed from the reaction, and the organic layer was directly purified by reverse phase column chromatography to give 158 mg (73%) of N-(2-(4-fluorophenyl)-2-methylpropyl)-5-vinylpyridin-2-amine.

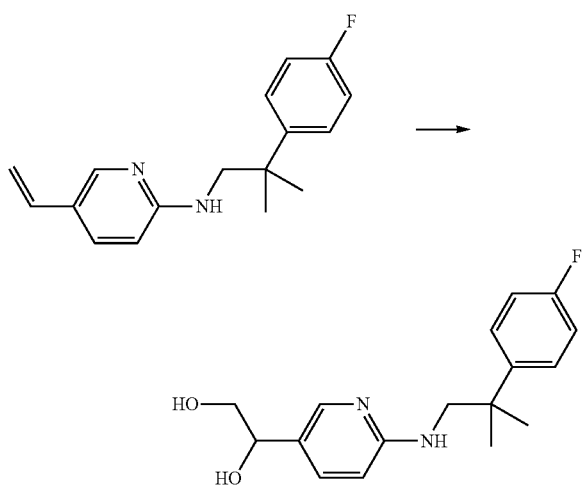

1-(6-(2-(4-Fluorophenyl)-2-methylpropylamino)pyridin-3-yl)ethane-1,2-diol

N-(2-(4-fluorophenyl)-2-methylpropyl)-5-vinylpyridin-2-amine (158 mg, 0.6 mmol, 1.0 equiv) was added to a foil-covered 20 dram vial and then dissolved in a 50% THF/water mixture (6 mL). Osmium tetraoxide (15 mg, 0.06 mmol, 0.1 equiv) and morpholine N-oxide (103 mg, 0.9 mmol, 1.5 equiv) were added, and the reaction was stirred for 1 h. Additional THF (3 mL) was added, and the reaction was stirred for 3 h. The reaction mixture was then diluted with water (10 mL) and extracted with ethyl acetate (30 mL). The organic layer was dried over Na$_2$SO$_4$, filtered, and concentrated to give a crude solid that was purified by reverse phase column chromatography to give 129 mg (86%) of 1-(6-(2-(4-fluorophenyl)-2-methylpropylamino)pyridin-3-yl)ethane-1,2-diol (m/z [M+H]=305).

EXAMPLE 10

N-(2-(6-(2-(4-Fluorophenyl)-2-methylpropylamino)pyridin-3-yl)ethyl)-methanesulfonamide

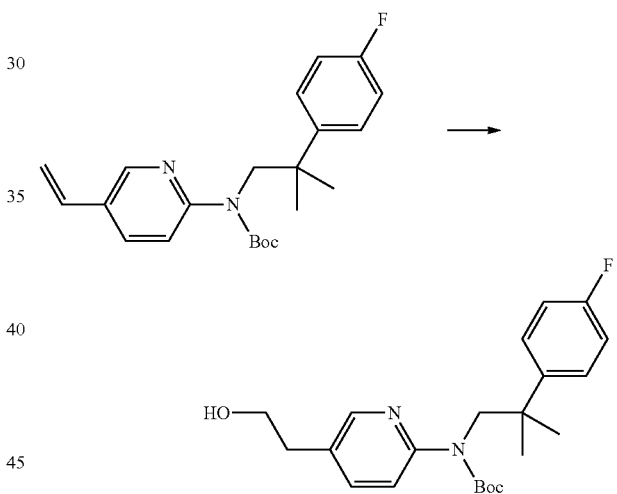

tert-Butyl 2-(4-fluorophenyl)-2-methylpropyl(5-(2-hydroxyethyl)pyridin-2-yl)carbamate To a 20 dram vial was added tert-butyl 2-(4-fluorophenyl)-2-methylpropyl(5-vinylpyridin-2-yl)carbamate (2.4 g, 6.4 mmol, 1.0 equiv) and THF (20 mL). Borane (7.7 mL, 7.7 mmol, 4.0 equiv) was added slowly, and the reaction was heated to 35° C. and stirred for 45 min. The reaction was then cooled to 0° C. followed by the addition of a 50% ethanol/THF mixture (25 mL), 2N sodium hydroxide (13 mL, 25.8 mmol, 4.0 equiv), and 30% hydrogen peroxide (15 mL). The reaction was stirred for 1 h, diluted with brine (10 mL), and extracted with ethyl acetate (20 mL). The organic layer was dried over Na$_2$SO$_4$, filtered, concentrated, and then purified by reverse phase column chromatography to give 414 mg (17%) of tert-butyl 2-(4-fluorophenyl)-2-methylpropyl(5-(2-hydroxyethyl)pyridin-2-yl)carbamate.

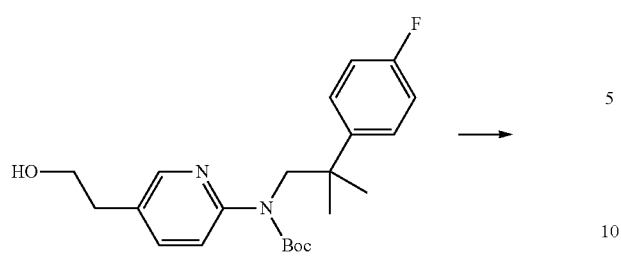

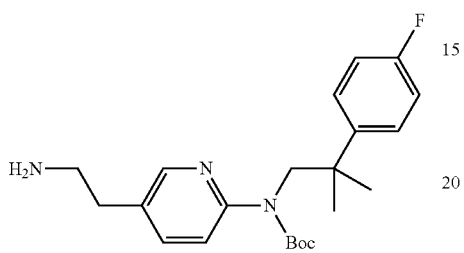

tert-Butyl-5-(2-aminoethyl)pyridin-2-yl(2-(4-fluorophenyl)-2-methylpropyl)-carbamate Methanesulfonyl chloride (87 μL, 1.1 mmol, 1.1 equiv) dissolved in 2 mL ethyl acetate was added to a 20 dram vial. To this stirring mixture was added a mixture of tert-butyl-2-(4-fluorophenyl)-2-methylpropyl(5-(2-hydroxyethyl)pyridin-2-yl)-carbamate (414 mg, 1.1 mmol, 1.0 equiv), TMEDA (167 μL, 1.1 mmol, 1.1 equiv), and ethyl acetate (3 mL) in a dropwise manner. The reaction was stirred for 1 h. The reaction mixture was then filtered and washed with saturated sodium bicarbonate and brine. The organic layer was dried over Na$_2$SO$_4$, filtered, and concentrated. The resultant solid was dissolved in DMF (4 mL), followed by the addition of sodium azide (139 mg, 2.1 mmol, 2.0 equiv). The reaction was stirred for 24 h, then diluted with water (10 mL) and extracted with ethyl acetate (20 mL). The organic layer was dried over Na$_2$SO$_4$, filtered, and concentrated. The crude solid was dissolved in methanol, followed by the addition of 10% palladium on carbon (80 mg), potassium carbonate (100 mg). The reaction was stirred under 45 psi of hydrogen for 24 h, filtered, and concentrated to give tert-butyl 5-(2-aminoethyl)pyridin-2-yl(2-(4-fluorophenyl)-2-methylpropyl)carbamate.

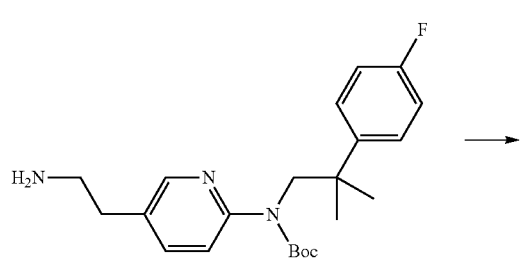

N-(2-(6-(2-(4-Fluorophenyl)-2-methylpropylamino)pyridin-3-yl)ethyl)-methanesulfonamide To a 20 dram vial was added tert-butyl 5-(2-aminoethyl)pyridin-2-yl(2-(4-fluorophenyl)-2-methylpropyl)carbamate (140 mg, 0.34 mmol, 1.0 equiv), TEA (87 μL, 0.67 mmol, 2.0 equiv, THF (3 mL), and methanesulfonyl chloride (29 μL, 0.37 mmol, 1.1 equiv). The reaction was stirred for 2 h and then concentrated, followed by the addition of MeOH (1 mL) and 4N HCl/dioxane (3 mL). The reaction was stirred for 1 h, concentrated, and then purified by preparative TLC (5% MeOH/CH$_2$Cl$_2$) to give 5 mg of N-(2-(6-(2-(4-fluorophenyl)-2-methylpropylamino)pyridin-3-yl)ethyl)-methanesulfonamide (m/z [M+H]=366).

EXAMPLE 11

6-(2-(4-Fluorophenyl)-2-methylpropylamino)nicotinamide

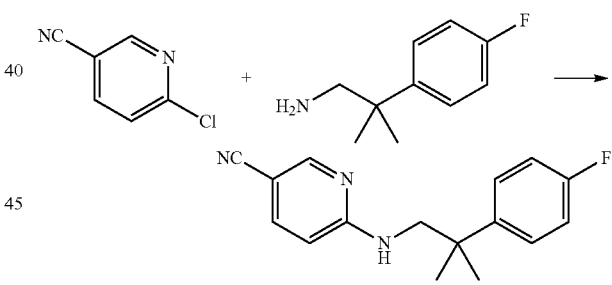

6-(2-(4-Fluorophenyl)-2-methylpropylamino)nicotinonitrile

To a solution of 6-chloronicotinonitrile (200 mg, 1.46 mmol, 1.0 equiv) and 2-(4-fluorophenyl)-2-methylpropan-1-amine (290 mg, 1.75 mmol, 1.2 equiv) in isopropanol (3 mL) in a microwave vial equipped with a stir bar was added potassium carbonate (720 mg, 2.19 mmol, 1.5 equiv). The vial was fitted with a microwave vial cap and heated to 120° C. for 20 min. The reaction mixture was filtered to remove the solid potassium carbonate and concentrated in vacuo. After the residue was redissolved in EtOAc and water, the organic layer was washed with brine, dried over sodium sulfate, and concentrated in vacuo. Purification by silica gel chromatography (1%-3% MeOH/DCM) provided the title compound as a beige solid (104 g, 27%), (m/z [M+H]=270.1).

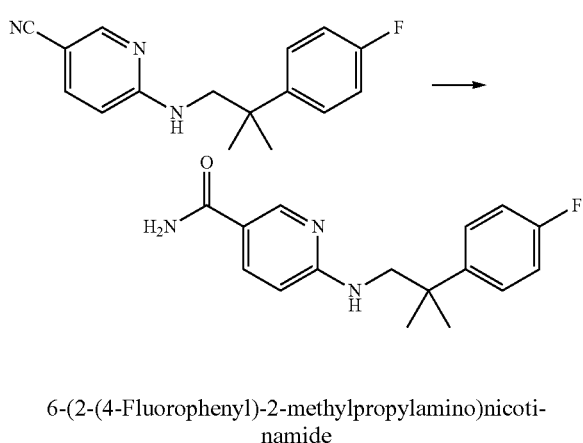

6-(2-(4-Fluorophenyl)-2-methylpropylamino)nicotinamide

To a cooled (0° C.) suspension of 6-(2-(4-fluorophenyl)-2-methylpropylamino)nicotinonitrile (75 mg, 0.28 mmol, 1.0 equiv) and $K_2CO_3$ (50 mg, 0.36 mmol, 1.3 equiv) in DMSO (1 mL) was added aq. $H_2O_2$ (250 uL, 30% by wt., 2.6 mmol, 9 equiv) by syringe. The reaction was allowed to warm to RT and stirred for 30 minutes. The resulting mixture was diluted with EtOAc and washed three times with satd. aq. LiCl and once with brine. The resulting solution was dried over sodium sulfate, filtered, and concentrated in vacuo. Purification by silica gel chromatography (2%-10% MeOH/DCM) provided the title compound as an off-white foam (54 mg, 77%), (m/z [M+H]=288.1).

EXAMPLE 12

Methyl (6-(2-(4-fluorophenyl)-2-methylpropylamino)pyridin-3-yl)methylcarbamate

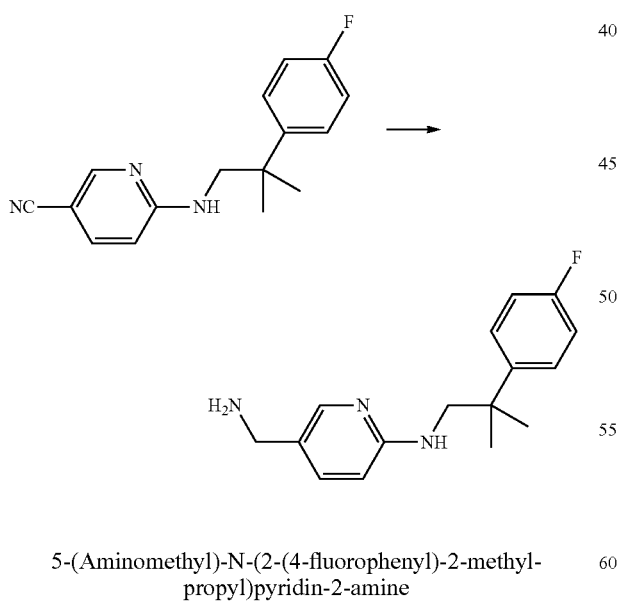

5-(Aminomethyl)-N-(2-(4-fluorophenyl)-2-methylpropyl)pyridin-2-amine

To a 100 mL round bottom flask was added 6-(2-(4-fluorophenyl)-2-methylpropylamino)nicotinonitrile (1.0 g, 3.7 mmol, 1.0 equiv) and THF (15 mL), followed by the addition of 1M lithium aluminum hydride/THF (14.8 mL, 14.8 mmol, 4.0 equiv). The reaction was heated to reflux for 3 h and allowed to cool to rt. The reaction mixture was then quenched by the sequential slow addition water (0.6 mL), 3N NaOH (0.6 mL), and water (1.7 mL). The resultant precipitate was filtered and the filtrate was then dried ($Na_2SO_4$) and concentrated to give 1.0 g (99%) of 5-(aminomethyl)-N-(2-(4-fluorophenyl)-2-methylpropyl)pyridin-2-amine.

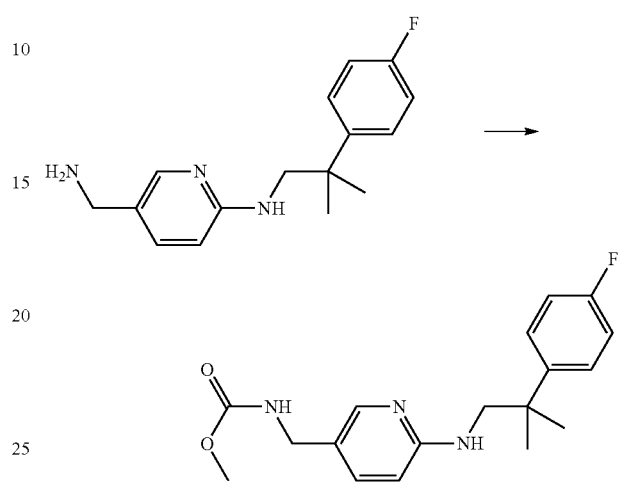

Methyl (6-(2-(4-fluorophenyl)-2-methylpropylamino)pyridin-3-yl)methylcarbamate

To a 20 dram vial was added 5-(aminomethyl)-N-(2-(4-fluorophenyl)-2-methylpropyl)pyridin-2-amine (100 mg, 0.37 mmol, 1.0 equiv), DIPEA (57 mg, 0.44 mmol, 1.2 equiv) and $CH_2Cl_2$ (1.2 mL). The mixture was cooled to 0° C., and methyl carbamate (35 mg, 0.4 mmol, 1.0 equiv) was then added. The reaction was allowed to warm to rt and stirred for 2 h. The reaction mixture was then diluted with water (2 mL) and extracted with ethyl acetate (15 mL). The organic layer was dried over $Na_2SO_4$, filtered, and concentrated to give a crude solid that was purified by silica gel column chromatography, affording 20 mg of methyl (6-(2-(4-fluorophenyl)-2-methylpropylamino)pyridin-3-yl)methylcarbamate (m/z [M+H]=332).

EXAMPLE 13

Preparation of 3-(6-(2-(4-fluorophenyl)-2-methylpropylamino)-1,2,4-triazin-3-yl)benzamide

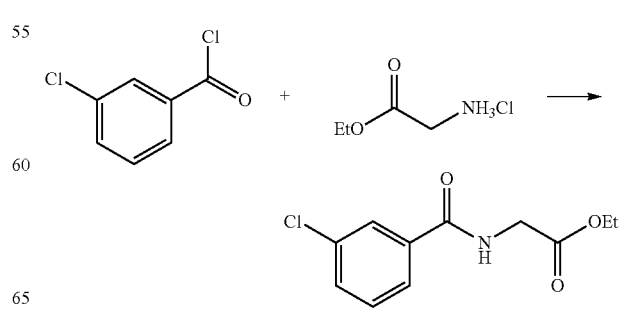

Ethyl 2-(3-chlorobenzamido)acetate

To a stirred solution of 3-chlorobenzoyl chloride (6.0 mL, 58 mmol) in dichloromethane (150 mL) were added ethyl glycinate hydrochloride (10 g, 72 mmol) and triethylamine (20 mL, 142 mmol). After stirring for 1 h, the mixture was diluted with saturated NaHCO₃ and the aqueous layer extracted twice with dichloromethane. The combined organic layers were dried over Na₂SO₄ and evaporated to dryness in vacuo to give the desired product (9.8 g) as a white solid which was taken on without purification.

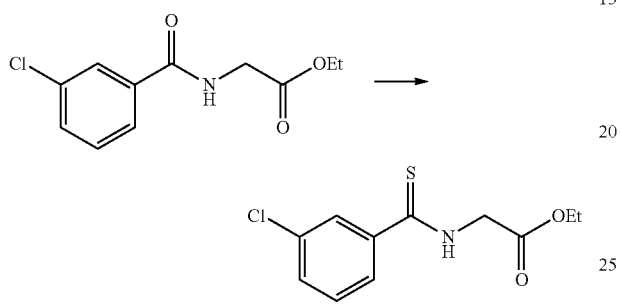

Ethyl 2-(3-chlorophenylthioamido)acetate

To a stirred solution of ethyl 2-(3-chlorobenzamido)acetate (9.8 g, 40 mmol) in toluene (150 mL) was added phosphorus pentasulfide (18 g, 42 mmol), and the mixture was heated to 120° C. for 1 h. The mixture was filtered, evaporated to dryness, and purified using silica gel chromatography (0-100% EtOAc/hexanes) as eluent gave 7.0 g of crude product which was carried forward without further purification

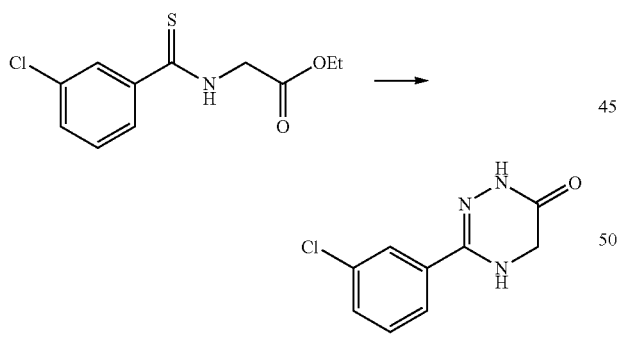

3-(3-Chlorophenyl)-4,5-dihydro-1,2,4-triazin-6(1H)-one

To a solution of ethyl 2-(3-bromophenylthioamido)acetate (~40 mmol) in ethanol (100 mL) was added hydrazine hydrate (5 mL). The mixture was heated to 90° C. for 2 h and allowed to cool to room temperature. Concentration in vacuo gave a yellow solid that was purified over silica gel using 10% MeOH/DCM as eluent to give the desired product (7.0 g) as an off-white solid.

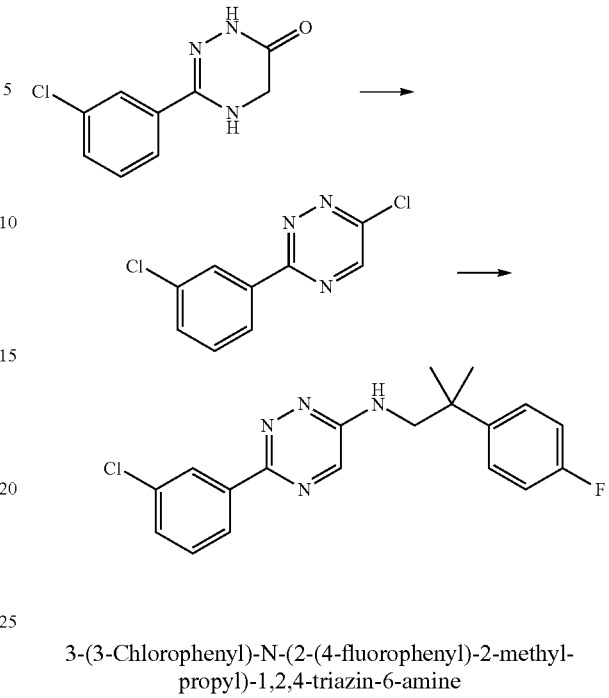

3-(3-Chlorophenyl)-N-(2-(4-fluorophenyl)-2-methylpropyl)-1,2,4-triazin-6-amine To a solution of 3-(3-chlorophenyl)-4,5-dihydro-1,2,4-triazin-6(1H)-one (6.0 g, 29 mmol) dissolved in dioxane (75 mL) was added MnO₂ (10 g, 120 mmol). The mixture was stirred at 90° C. for 18 h. After filtering through diatomaceous earth and rinsing with hot dioxane, the combined organics were evaporated to dryness in vacuo. The crude residue (⅓ was used) was dissolved in POCl₃ (10 mL, 108 mmol) and heated to 70° C. for 2.5 h. The mixture was allowed to cool to rt and evaporated to dryness in vacuo. The residue was dissolved in EtOAc/ether (1:1) and washed with 1 M NaOH. The organic phase was evaporated to dryness and dissolved in NMP (5.0 mL) in a microwave vial. Potassium carbonate (1.0 g) was added followed by (2-(4-fluorophenyl)-2-methylpropan-1-amine (2.0 g, 12 mmol), and the mixture was heated in a microwave reactor to 165° C. for 20 min. The solution was diluted with EtOAc and washed with saturated NaCl (4×), dried over Na₂SO₄, and evaporated to dryness. Purification using silica gel chromatography (0-35% EtOAc/hexanes) gave the desired product (430 mg) as an orange film.

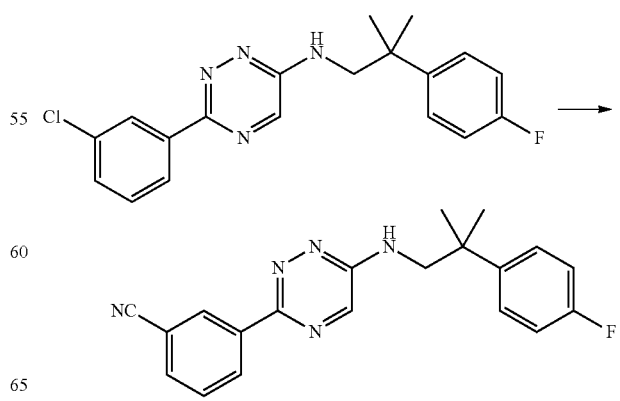

3-(6-(2-(4-Fluorophenyl)-2-methylpropylamino)-1,2,4-triazin-3-yl)benzonitrile To a microwave vial containing NiBr₂ (280 mg, 1.3 mmol) and NaCN (120 mg, 2.5 mmol) was added a solution of 3-(3-chlorophenyl)-N-(2-(4-fluorophenyl)-2-methylpropyl)-1,2,4-triazin-6-amine (450 mg, 1.3 mmol) in NMP (4.0 mL). The vial was purged with nitrogen and sealed. The mixture was heated to 200° C. in a microwave for 25 min and allowed to cool to room temperature. The solution was diluted with EtOAc/ether (1:1), washed with water (3×), dried over Na₂SO₄ and evaporated to dryness. Purification using silica gel chromatography (0-65% EtOAc/hexanes) gave the desired product (220 mg) as an off white foam.

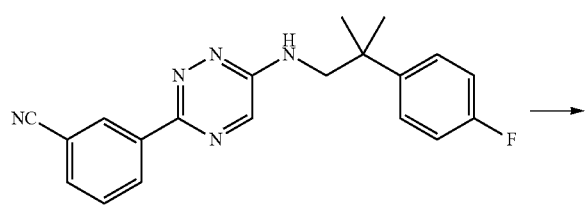

3-(6-(2-(4-fluorophenyl)-2-methylpropylamino)-1,2,4-triazin-3-yl)benzamide

To a solution of 3-(6-(2-(4-fluorophenyl)-2-methylpropylamino)-1,2,4-triazin-3-yl)benzonitrile (220 mg, 0.60 mmol) in DMSO (3.0 mL) was added K₂CO₃ (300 mg, 2.2 mmol) and 30% hydrogen peroxide (0.60 mL, 7.5 mmol). The mixture was stirred 24 h and partitioned between EtOAc and water. The aqueous layer was extracted with EtOAc (2×) and the combined organics were dried over Na₂SO₄ and evaporated to dryness in vacuo. Purification using silica gel chromatography (0-100% EtOAc/hexanes) gave the desired product (17 mg), m/z=366.1 [M+H].

EXAMPLE 14

Preparation of 5-(3-(2-(4-fluorophenyl)-2-methylpropylamino)-1,2,4-triazin-6-yl)-1H-indazol-3-amine

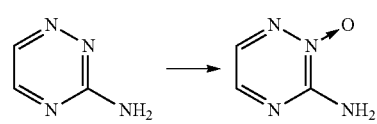 [SMILES: Nc1nccnn1 ; Nc1nccn[n+]1[O-]]

3-Amino-1,2,4-triazin-2-oxide

To a solution of 1,2,4-triazin-3-amine (2.8 g, 30 mmol) in CH₃CN (25 mL) was added portionwise mCPBA (14 g, 81 mmol). The mixture was refluxed for 2 h and then evaporated to dryness. The residue was mixed with ether and filtered to give the desired product as a yellow solid that was used in the next step without purification.

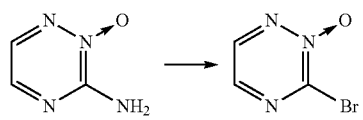 [SMILES: Nc1nccn[n+]1[O-] ; [O-][n+]1nccnc1Br]

3-Bromo-1,2,4-triazin-2-oxide

To a solution of 48% (wt/wt) HBr (100 mL) was added 1,2,4-triazin-3-amine-2-oxide (30 mmol), and the mixture was stirred at rt. A solution of NaNO₂ (30 g, 430 mmol) in water (40 mL) was added slowly, and the mixture was stirred for 1 h. The reaction was quenched by the addition of an excess of saturated NaHCO₃ and extracted with dichloromethane. The combined organic layers were evaporated to dryness. Purification using silica gel chromatography (EtOAc/hexanes) gave 1.3 g of the intermediate bromide product.

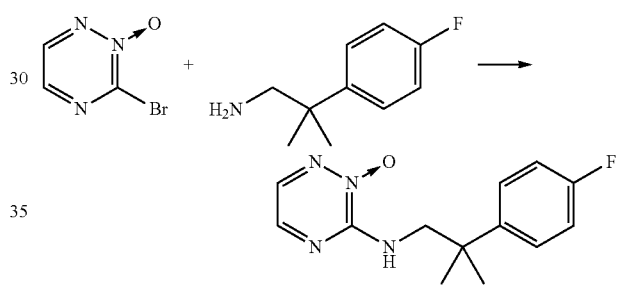

N-(2-(4-Fluorophenyl)-2-methylpropyl)-1,2,4-triazin-3-amine-2-oxide

A solution of 3-bromo-1,2,4-triazin-2-oxide (2.0 g, 11 mmol), (2-(4-fluorophenyl)-2-methylpropan-1-amine (3.0 g, 17 mmol), and diisopropylethylamine (3.0 mL, 17 mmol) in CH₃CN (20 mL) was stirred at rt for 24 h. The solvents were removed and the residue dissolved in EtOAc. The solution was washed with saturated NaHCO₃, dried over Na₂SO₄, and evaporated to dryness. The residue was mixed with ether and then filtered to give the desired product (1.2 g) as a yellow solid.

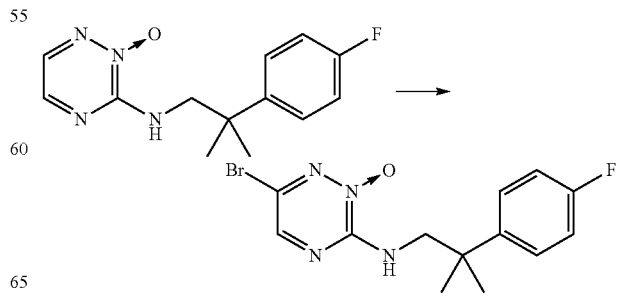

6-Bromo-N-(2-(4-fluorophenyl)-2-methylpropyl)-1,2,4-triazin-3-amine-2-oxide

To a solution of N-(2-(4-fluorophenyl)-2-methylpropyl)-1,2,4-triazin-3-amine-2-oxide (1.2 g, 7.4 mmol) in a 1:1 mixture of dichloromethane and CH₃CN (40 mL) was added Br₂ (1.0 mL, 19 mmol). The mixture was stirred at room temperature for 72 h. The solvents were evaporated and the residue was dissolved in ether. The solution was filtered through a plug of silica gel and the solvents evaporated to give the desired product (1.5 g, 58%) as an orange sticky solid.

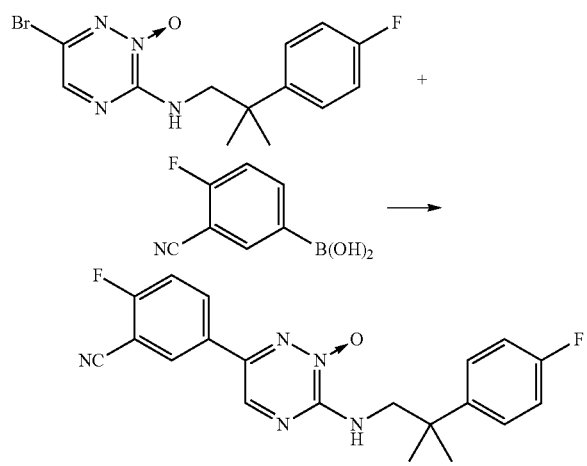

2-Fluoro-5-(3-(2-(4-fluorophenyl)-2-methylpropylamino)-1,2,4-triazin-2-oxide-6-yl)benzonitrile To a solution of 6-bromo-N-(2-(4-fluorophenyl)-2-methylpropyl)-1,2,4-triazin-3-amine-2-oxide (0.48 g, 1.4 mmol, 1.0 equiv), 3-cyano-4-fluorophenylboronic acid (0.35 g, 2.1 mmol), and K₂CO₃ (0.5 g, 3.6 mmol) in DMF (2 mL) was added Pd(dppf)Cl₂ (0.10 g, 0.13 mmol). The mixture was stirred at 75° C. for 4 h and then quenched by addition of excess saturated NaHCO₃. The mixture was extracted with EtOAc and the organic layer was concentrated. Purification using silica gel chromatography (1-40% EtOAc/hexanes) gave the desired product (0.38 g) as a yellow solid.

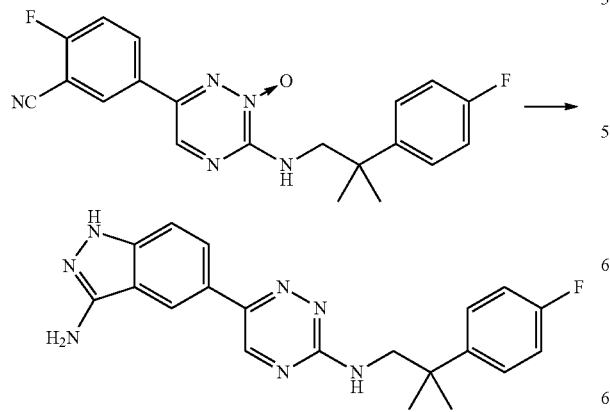

5-(3-(2-(4-fluorophenyl)-2-methylpropylamino)-1,2,4-triazin-6-yl)-1H-indazol-3-amine A stirred solution of 2-fluoro-5-(3-(2-(4-fluorophenyl)-2-methylpropylamino)-1,2,4-triazin-2-oxide-6-yl)benzonitrile (0.18 g, 0.47 mmol) and hydrazine (0.1 mL, 2.0 mmol) in n-butanol (0.5 mL) was sealed and heated to 119° C. for 1 h. The solvents were removed and the residue dissolved in benzylamine with a minimal amount of CH₃CN. The mixture was sealed and stirred at 177° C. overnight. The mixture was loaded directly onto a reverse phase HPLC for purification using a gradient of CH₃CN/water to give the desired product (28 mg), m/z=378.1 [M+H].

EXAMPLE 15

Preparation of 4-fluoro-3-(3-(2-(3-fluoropyridin-2-yl)propan-2-ylamino)-1,2,4-triazin-6-yl)benzamide

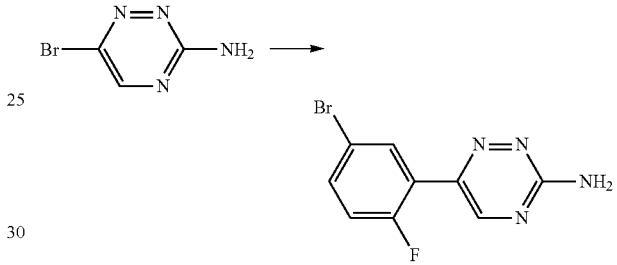

6-(5-Bromo-2-fluorophenyl)-1,2,4-triazin-3-amine

6-Bromo-1,2,4-triazin-3-amine (9.1 g, 40.8 mmol), 5-bromo-2-fluorophenylboronic acid (98.9 g, 40.8 mmol), (dppf)PdCl₂ (3.0 g, 4.0 mmol), nitrogen-sparged dioxane (81.6 mL), and aq. 2 N K₂CO₃ (17 mL) were combined and heated in a round bottom flask at 90° C. for 4 h. The hot mixture was filtered through a pad of celite and diluted with EtOAc and washed with water. Concentration followed by trituration with DCM afforded a tan solid (4.5 g), m/z=269.0 [M+H].

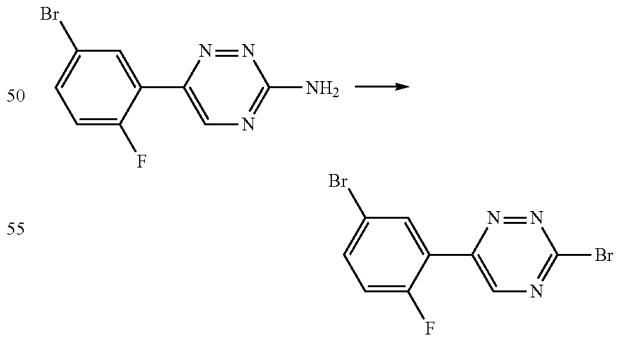

3-Bromo-6-(5-bromo-2-fluorophenyl)-1,2,4-triazine 6-(5-Bromo-2-fluorophenyl)-1,2,4-triazin-3-amine (4.5 g, 16.7 mmol) was dissolved in 25 mL of bromoform and heated to 80° C. Isoamyl nitrite (9.8 g, 83.5 mmol) was then added and stirred at 85° C. for 1 h. The reaction mixture was then concentrated and silica gel chromatography afforded a yellow solid (4.4 g), m/z=331.1 [M+H].

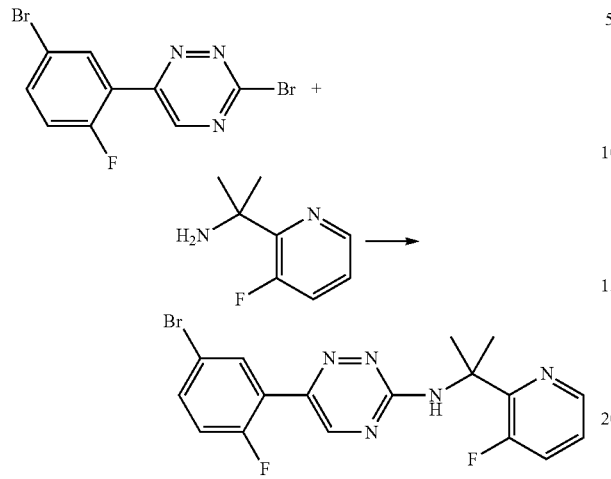

6-(5-Bromo-2-fluorophenyl)-N-(2-(2-fluorophenyl)propan-2-yl)-1,2,4-triazin-3-amine 3-Bromo-6-(5-bromo-2-fluorophenyl)-1,2,4-triazine (2.8 g, 8.4 mmol), 2-(2-fluorophenyl)propan-2-amine (2.0 g, 12.6 mmol), $K_2CO_3$ (2.3 g, 16.8 mmol) and $CH_3CN$ (20 mL) was heated to 90° C. The reaction mixture was diluted with EtOAc and washed with satd. aq. $NaHCO_3$ and brine. The organic layer was dried over sodium sulfate, filtered, concentrated, and purified using silica gel chromatography to afford a yellow solid (2.3 g), m/z=406.1 [M+H].

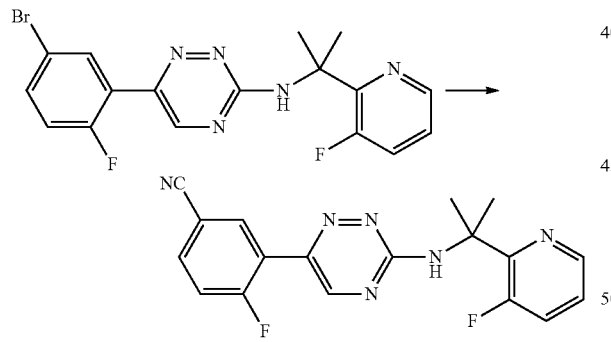

4-Fluoro-3-(3-(2-(2-fluorophenyl)propan-2-ylamino)-1,2,4-triazin-6-yl)benzonitrile 6-(5-Bromo-2-fluorophenyl)-N-(2-(2-fluorophenyl)propan-2-yl)-1,2,4-triazin-3-amine (2.2 g, 5.6 mmol), zinc cyanide (0.72 g, 6.2 mmol), $Pd(PPh_3)_4$ (2.9 g, 2.8 mmol), and DMF (20 mL) were combined and heated in a round bottom flask at 100° C. for 2 h. The reaction mixture was diluted with EtOAc and washed with satd. aq. $NaHCO_3$ and brine. The organic layer was dried over sodium sulfate, filtered, concentrated and purified using silica gel chromatography to provide a yellow solid (1.7 g), m/z=352.1 [M+H].

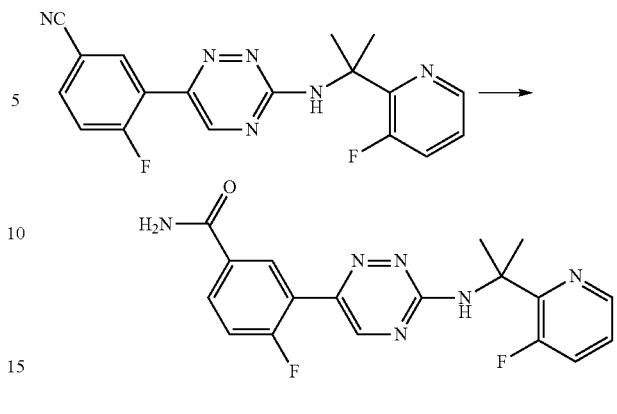

4-Fluoro-3-(3-(2-(3-fluoropyridin-2-yl)propan-2-ylamino)-1,2,4-triazin-6-yl)benzamide 4-Fluoro-3-(3-(2-(2-fluorophenyl)propan-2-ylamino)-1,2,4-triazin-6-yl)benzonitrile (4.0 g, 11.3 mmol), $K_2CO_3$ (6.2 g, 21.2 mmol), and DMSO (113 mL) were combined in a round bottom flask and cooled to 0° C. $H_2O_2$ (38 mL of 35% solution) was then added dropwise and the reaction was warmed to rt and stirred for 1 h. The reaction mixture was diluted with EtOAc and washed with satd. aq. $NaHCO_3$ and brine. The organic layer was dried over sodium sulfate, filtered, concentrated, and purified using silica gel chromatography to afford a white solid (3.3 g), m/z=371.1 [M+H].

EXAMPLE 16

Preparation of (1-(6-Methoxypyridin-2-yl)cyclobutyl)methanamine

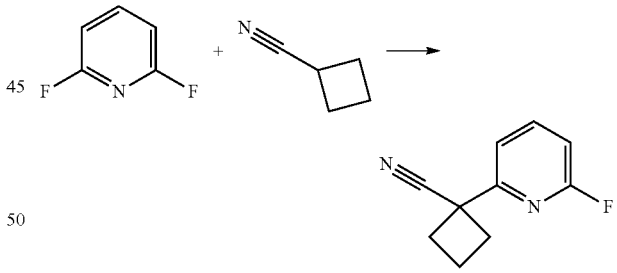

1-(6-Fluoropyridin-2-yl)cyclobutanecarbonitrile

To a 0° C. solution of 2,6-difluoropyridine (5.0 g, 43 mmol), cyclobutanecarbonitrile (3.5 g, 43 mmol), and toluene (100 mL) was added sodium hexamethyldisilazide (NaHMDS, 2.0 M in THF, 24 mL, 47 mmol). The resulting mixture was warmed to rt and stirred for 2 h. The mixture was then diluted with EtOAc (200 mL) and water (100 mL). The aqueous layer was extracted with EtOAc and the combined organic phases were washed with brine, dried over $Na_2SO_4$, concentrated, and purified using silica gel chromatography to provide the desired product (4.9 g) as a colorless oil.

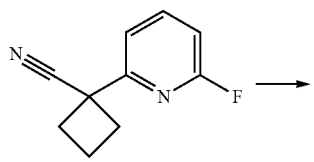

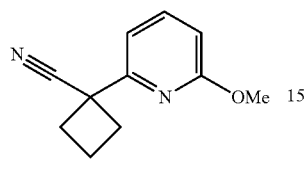

1-(6-Methoxypyridin-2-yl)cyclobutanecarbonitrile

To anhydrous methanol (6 mL) at 0° C. under nitrogen was added sodium metal (ca 1 g) and the mixture stirred for 30 min. 1-(6-fluoropyridin-2-yl)cyclobutanecarbonitrile (1.6 g, 9.1 mmol) was then added, and the resulting mixture heated to 75° C. for 45 min. The solution was cooled to room temperature and partitioned between water and EtOAc. The layers were separated, the aqueous phase was extracted with EtOAc, and the combined organic phases were washed with brine, dried over $Na_2SO_4$, and concentrated in vacuo to give the desired product (1.7 g) as an oil.

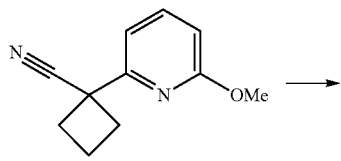

(1-(6-Methoxypyridin-2-yl)cyclobutyl)methanamine

To a stirred solution of 1-(6-methoxypyridin-2-yl)cyclobutanecarbonitrile (1.7 g, 8.8 mmol) in THF (20 mL) was added lithium aluminum hydride solution (1.0 M in THF, 11 mL, 11 mmol). The mixture was refluxed for 1.5 h and allowed to cool to room temperature. Water (0.43 mL) was slowly added, followed by 0.43 mL of 3 M NaOH, and then three additions of 0.43 mL of water. The resulting mixture was filtered through diatomaceous earth and rinsed with THF. The combined organics were dried over $Na_2SO_4$ and concentrated to dryness to give the desired product (1.6 g) as a viscous oil.

EXAMPLE 17

Preparation of 1-(3-Fluoropyridin-2-yl)cyclobutanamine Example 5(a)

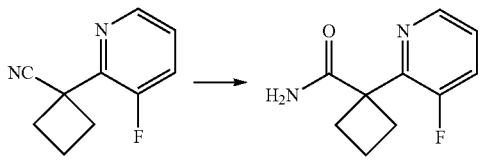 [SMILES: N#CC1(c2ncccc2F)CCC1 ; NC(=O)C1(c2ncccc2F)CCC1]

1-(3-Fluoropyridin-2-yl)cyclobutanecarboxamide

To a 250 mL round bottom flask was added DMSO (60 mL) and 1-(3-fluoropyridin-2-yl)cyclobutanecarbonitrile (2.96 g, 16.8 mmol), and the mixture was stirred until homogenous. Potassium carbonate (7.0 g, 50.4 mmol) was then added and the reaction mixture was cooled to 0° C., followed by the addition of 35% hydrogen peroxide (6.5 mL). The reaction was stirred at 0° C. for 30 min and then warmed to rt. At this time, the reaction was diluted with water (50 mL) and ethyl acetate (100 mL). After transferring to a separatory funnel and shaking, the organic layer was separated from the aqueous layer and then washed with brine (3×50 mL). The organic layer was then dried over $Na_2SO_4$, filtered, and concentrated to give a crude solid that was purified by silica gel chromatography (10% EtOAC/hexanes) to afford 1.92 g of 1-(3-fluoropyridin-2-yl)cyclobutanecarboxamide as a white solid.

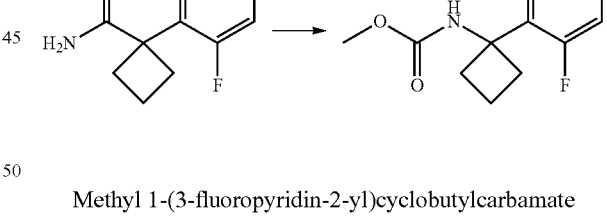

Methyl 1-(3-fluoropyridin-2-yl)cyclobutylcarbamate 1-(3-fluoropyridin-2-yl)cyclobutanecarboxamide (1.92 g, 9.88 mmol) was dissolved in methanol (20 mL) and potassium hydroxide (1.11 g, 19.8 mmol, 2.0 equiv) was added. The mixture was sonicated until homogeneous, followed by the addition of iodosobenzene diacetate (4.77 g, 14.8 mmol). The reaction was stirred for 20 min and then diluted with water (100 mL) and ethyl acetate (125 mL). After transferring to a separatory funnel and shaking, the organic layer was separated from the aqueous layer, and the aqueous layer was extracted with EtOAc (50 mL). The combined organic layers were then dried over $Na_2SO_4$, filtered, and concentrated to give a crude oil that was purified by silica gel chromatography (40% EtOAC/hexanes) to afford 1.47 g of methyl 1-(3-fluoropyridin-2-yl)cyclobutylcarbamate as a white solid.

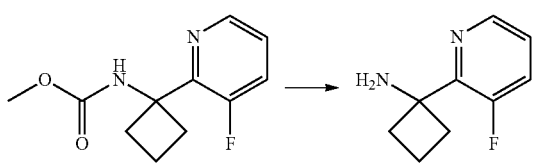 [SMILES: COC(=O)NC1(c2ncccc2F)CCC1 ; NC1(c2ncccc2F)CCC1]

1-(3-Fluoropyridin-2-yl)cyclobutanamine

To a 20 mL microwave reaction vial was added methyl 1-(3-fluoropyridin-2-yl)cyclobutylcarbamate (1.47 g, 6.56 mmol), ethanol (12 mL) and 3N aqueous sodium hydroxide (7 mL). The reaction mixture was heated in the microwave reactor at 150° C. for 30 min. The ethanol was evaporated under reduced pressure and the mixture was extracted with ethyl acetate (30 mL). The aqueous layer was then extracted with ethyl acetate (2×30 mL). The organic layers were combined, dried over Na$_2$SO$_4$, filtered, and concentrated to give 1-(3-fluoropyridin-2-yl)cyclobutanamine (1.01 g) as a crude yellow oil that was used in the next reaction step without further purification.

EXAMPLE 18

Preparation of trans-3-Fluoro-1-(3-fluoropyridin-2-yl)cyclobutyl)methanamine

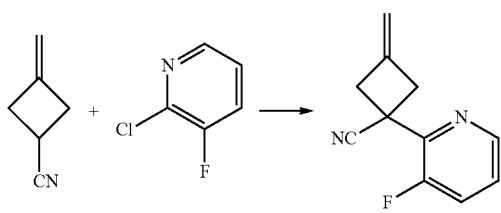

1-(3-Fluoropyridin-2-yl)-3-methylenecyclobutanecarbonitrile

To a solution of 3-methylenecyclobutanecarbonitrile (150 g, 1.61 mol, 1 equiv) and 2-chloro-3-fluoropyridine (212 g, 1.61 mmol, 1 equiv) in toluene (1 L) was added NaHMDS (2 M in THF, 885 mL, 1.1 equiv) dropwise at 0-10° C. Upon completion of addition, the reaction mixture was warmed to rt, stirred overnight, and quenched with NH$_4$Cl$_{(sat.)}$ solution. The organic layer was washed with water (2×500 mL) and brine (500 mL), dried over Na$_2$SO$_4$, filtered, and concentrated to give the crude title compound (272 g) which was used in next step without further purification, m/z=189.1 [M+H].

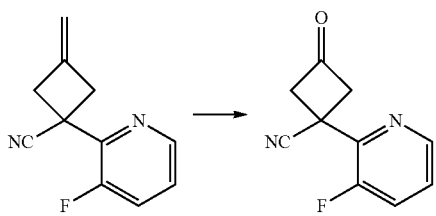

1-(3-Fluoropyridin-2-yl)-3-oxocyclobutanecarbonitrile

To a mixture of 1-(3-fluoropyridin-2-yl)-3-methylenecyclobutanecarbonitrile (272 g, 1.45 mol) and RuCl$_3$.H$_2$O (9.0 g, 0.044 mol) in DCM (1 L), acetonitrile (1 L), and water (1.5 L) mixture was added solid NaIO$_4$ (1235 g, 5.8 mol) portionwise at 10-30° C. Upon the completion of addition, the reaction was stirred 1 h at 15° C. and overnight at rt. The solid precipitate was filtered off and washed with DCM (2×1000 mL). The organic layer was washed with water (2×500 mL) and brine (500 mL), dried over Na$_2$SO$_4$, and concentrated to provide a crude title compound as a dark solid (238 g), m/z=191.1 [M+H].

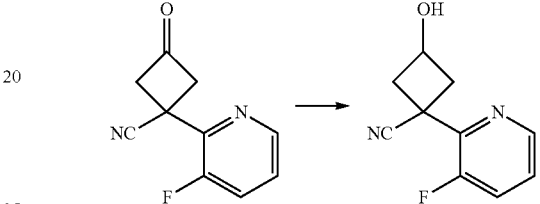

1-(3-Fluoropyridin-2-yl)-3-hydroxycyclobutanecarbonitrile

To a solution of 1-(3-fluoropyridin-2-yl)-3-oxocyclobutanecarbonitrile (231 g, 1.22 mol) in a mixture of DCM (2 L) and MeOH (200 mL) was added NaBH$_4$ portionwise at −78° C. The reaction mixture was stirred at −78° C. for 1 h and quenched with a mixture of methanol and water (1/1). The organic layer was washed with water (500 mL×3), dried over Na$_2$SO$_4$, and concentrated. The residue was purified on silica gel (50% EtOAc/hexanes) to provide the title compound as an amber oil (185.8 g) m/z=193.2 [M+H].

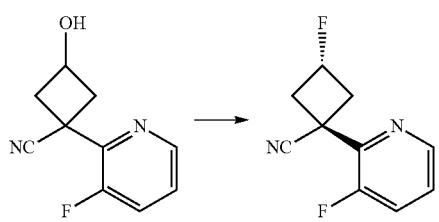 [SMILES: N#CC1(c2ncccc2F)CC(O)C1 ; N#C[C@]1(c2ncccc2F)C[C@H](F)C1]

trans-3-Fluoro-1-(3-fluoropyridin-2-yl)cyclobutanecarbonitrile

To a solution of 1-(3-fluoropyridin-2-yl)-3-hydroxycyclobutanecarbonitrile (185 g, 0.96 mol) in DCM (1 L) was added DAST portionwise at 0-10° C. Upon the completion of addition, the reaction was refluxed for 6 h. The reaction was cooled to rt and poured onto sat. NaHCO$_3$ solution. The mixture was separated and the organic layer was washed with water, dried over Na$_2$SO$_4$, and concentrated. The residue was purified on silica gel (100% DCM) to provide the title compound as a brown oil (116 g, 62%) in a 8:1 trans:cis mixture. The above brown oil (107 g) was dissolved in toluene (110 mL) and hexanes (330 mL) at 70° C. The solution was cooled to 0° C. and stirred at 0° C. overnight. The precipitate was filtered and washed with hexanes to provide the trans isomer as a white solid (87.3 g), m/z=195.1 [M+H].

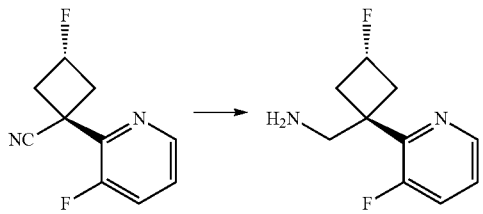 [SMILES: N#C[C@]1(c2ncccc2F)C[C@H](F)C1 ; NC[C@]1(c2ncccc2F)C[C@H](F)C1]

trans-3-Fluoro-1-(3-fluoropyridin-2-yl)cyclobutyl)
methanamine

A mixture of trans-3-fluoro-1-(3-fluoropyridin-2-yl)cyclobutanecarbonitrile (71 g, 0.37 mol) and Raney nickel (~7 g) in 7N ammonia in methanol (700 mL) was charged with hydrogen (60 psi) for 2 days. The reaction was filtered through a celite pad and washed with methanol. The filtrate was concentrated under high vacuum to provide the title compound as a light green oil (70 g), m/z=199.2 [M+H].

EXAMPLE 19

Preparation of 4-fluoro-3-(3-(((trans)-3-fluoro-1-(3-fluoropyridin-2-yl)cyclobutyl)methylamino)-1,2,4-triazin-6-yl)-N-methylbenzamide

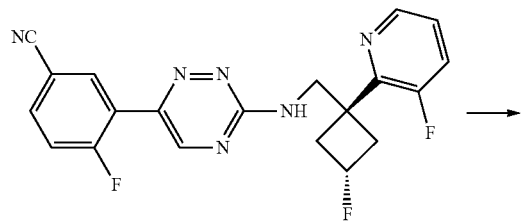

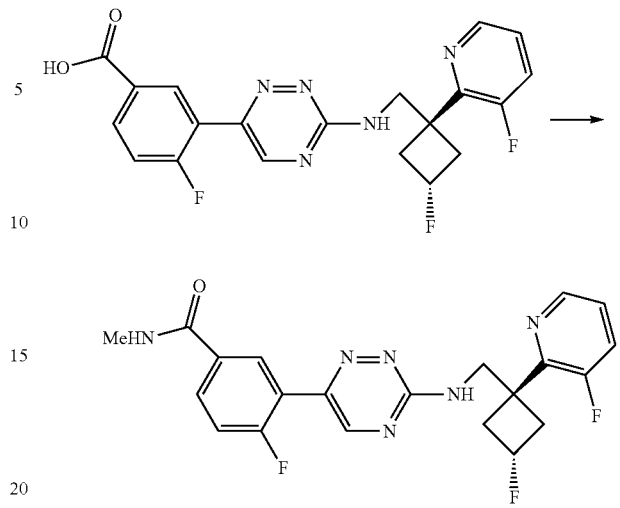

4-Fluoro-3-(3-(((trans)-3-fluoro-1-(3-fluoropyridin-2-yl)cyclobutyl)methylamino)-1,2,4-triazin-6-yl)-N-methylbenzamide 4-Fluoro-3-(3-(((trans)-3-fluoro-1-(3-fluoropyridin-2-yl)cyclobutyl)methylamino)-1,2,4-triazin-6-yl)benzoic acid (0.5 g, 1.2 mmol) was diluted in 18 mL DMF and treated with HBTU (1.8 g, 4.8 mmol), HOBT (0.65 g, 4.8 mmol), methyl amine hydrochloride (0.32 g, 4.8 mmol), and DIEA (8.4 mL, 48 mmol). The mixture was stirred at 24° C. for 30 min, diluted with EtOAc, washed with water and brine, concentrated, and purified using reverse phase chromatography to afford a tan solid (0.25 g, (m/z [M−H]=429.3).

EXAMPLE 20

Preparation of 1-(3-chloropyridin-2-yl)-3,3-difluorocyclobutanecarbonitrile

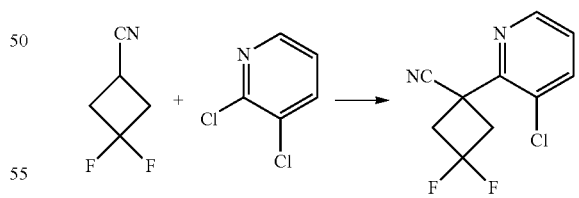

4-Fluoro-3-(3-(((trans)-3-fluoro-1-(3-fluoropyridin-2-yl)cyclobutyl)methylamino)-1,2,4-triazin-6-yl)
benzoic acid 4-Fluoro-3-(3-(((trans)-3-fluoro-1-(3-fluoropyridin-2-yl)cyclobutyl)methylamino)-1,2,4-triazin-6-yl)benzonitrile (1.3 g, 74.5 mmol) was diluted in 20 mL of concentrated HCl and heated in a microwave reactor at 110° C. for 30 min. The mixture was then concentrated and carried on to next step without further purification, (m/z [M−H]=414.1).

To a 100 mL round bottom flask was added 2,3-dichloropyridine (2.9 g, 20 mmol), 3,3-difluorocyclobutanecarbonitrile (2.1 g, 18 mmol), and toluene (50 mL). The mixture was cooled to ° C. and sodium hexamethyldisilazide (NaHMDS, 2.0 M in THF, 11 mL, 22 mmol) was added. The reaction mixture was warmed to rt and stirred for 2 h. The mixture was then diluted with EtOAc (20 mL) and water (20 mL). The aqueous layer was extracted with EtOAc and the combined organic phases were washed with brine, dried over Na₂SO₄, and concentrated to provide the desired product (3.4 g) as a colorless oil.

EXAMPLE 21

Preparation of 4-fluoro-3-(3-(((trans)-3-fluoro-1-(3-fluoropyridin-2-yl)cyclobutyl)methylamino)-1,2,4-triazin-6-yl)-2-hydroxybenzamide

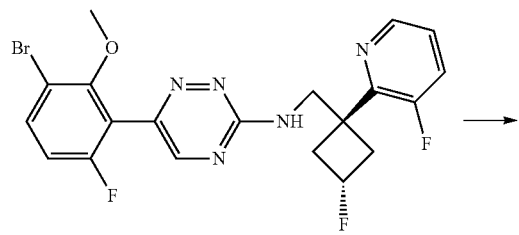

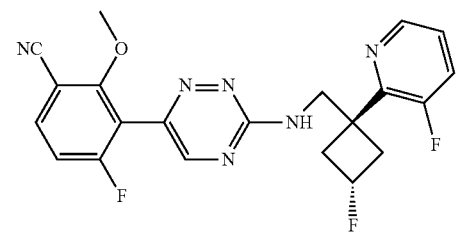

4-Fluoro-3-(3-(((trans)-3-fluoro-1-(3-fluoropyridin-2-yl)cyclobutyl)methylamino)-1,2,4-triazin-6-yl)-2-methoxybenzonitrile 6-(3-Bromo-6-fluoro-2-methoxyphenyl)-N-(((trans)-3-fluoro-1-(3-fluoropyridin-2-yl)cyclobutyl)methyl)-1,2,4-triazin-3-amine (448 mg, 0.93 mmol), zinc cyanide (131 mg, 1.1 mmol), Pd(PPh₃)₄ (296 mg, 0.3 mmol), and DMF (5 mL) were combined and heated to 100° C. for 2 h. The reaction mixture was cooled and filtered through Celite. The reaction mixture was then diluted with EtOAc and washed with satd. aq. NaHCO₃ and brine. The organic layer was dried over sodium sulfate, filtered, concentrated, and purified using silica gel chromatography to afford 4-fluoro-3-(3-(((trans)-3-fluoro-1-(3-fluoropyridin-2-yl)cyclobutyl)methylamino)-1,2,4-triazin-6-yl)-2-methoxybenzonitrile (229 mg).

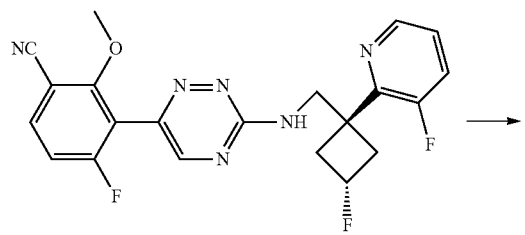

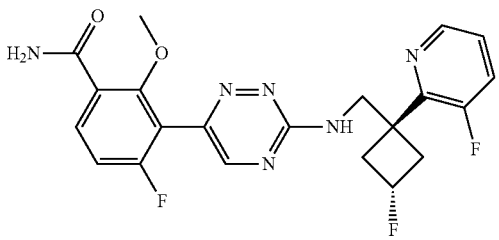

4-Fluoro-3-(3-(((trans)-3-fluoro-1-(3-fluoropyridin-2-yl)cyclobutyl)methylamino)-1,2,4-triazin-6-yl)-2-methoxybenzamide 4-Fluoro-3-(3-(((trans)-3-fluoro-1-(3-fluoropyridin-2-yl)cyclobutyl)methylamino)-1,2,4-triazin-6-yl)-2-methoxybenzonitrile (229 mg, 0.54 mmol), K₂CO₃ (200 mg, 1.4 mmol), and DMSO (5 mL) were combined in a round bottom flask and cooled to 0° C. H₂O₂ (1 mL of 35% solution) was then added dropwise and the reaction was warmed to rt and stirred for 1 h. The reaction mixture was diluted with EtOAc and washed with satd. aq. NaHCO₃ and brine. The organic layer was dried over sodium sulfate, filtered, concentrated, and purified using silica gel chromatography to afford 210 mg of 4-fluoro-3-(3-(((trans)-3-fluoro-1-(3-fluoropyridin-2-yl)cyclobutyl)methylamino)-1,2,4-triazin-6-yl)-2-methoxybenzamide.

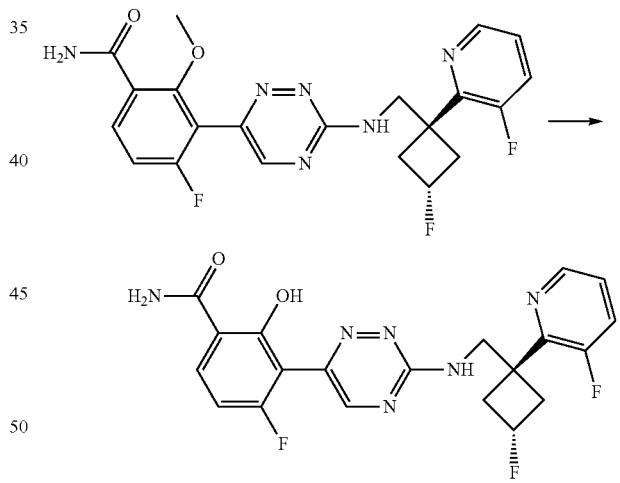

4-Fluoro-3-(3-(((trans)-3-fluoro-1-(3-fluoropyridin-2-yl)cyclobutyl)methylamino)-1,2,4-triazin-6-yl)-2-hydroxybenzamide Lithium iodide (1 g), pyridine (20 mL), and 4-fluoro-3-(3-(((trans)-3-fluoro-1-(3-fluoropyridin-2-yl)cyclobutyl)methylamino)-1,2,4-triazin-6-yl)-2-methoxybenzamide (210 mg) were added to a round bottom flask. The reaction was heated to 125° C. and stirred for 2 h. The reaction was concentrated, mixed with methanol, filtered, and purified using reverse phase chromatography to afford 24 mg of 4-fluoro- 3-(3-(((trans)-3-fluoro-1-(3-fluoropyridin-2-yl)cyclobutyl) methylamino)-1,2,4-triazin-6-yl)-2-hydroxybenzamide, m/z=430.1 [M+H].

EXAMPLE 22

Preparation of N-((2-(3-(((trans)-3-fluoro-1-(3-fluoropyridin-2-yl)cyclobutyl)methylamino)-1,2,4-triazin-6-yl)thiazol-5-yl)methyl)acetamide

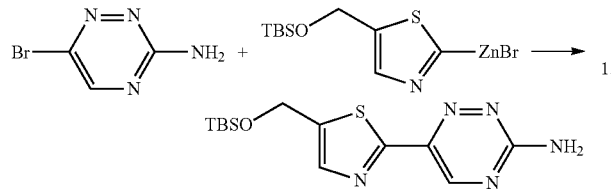

6-(5-((tert-Butyldimethylsilyloxy)methyl)thiazol-2-yl)-1,2,4-triazin-3-amine

Diisopropylamine (13.7 mL, 98 mmol) and THF (100 mL) were added to a round bottom flask. The mixture was cooled to −78° C. and n-BuLi (2.5 M, 40 mL, 100 mmol) was added. The reaction was stirred for 30 min, followed by the addition of (5-((tert-butyldimethylsilyloxy)methyl)thiazol-2-yl) (17.1 g, 75 mmol). The reaction was stirred to 30 min followed by the addition of zinc bromide (18 g, 69 mmol). The reaction was stirred for 1 h at −78° C. and then warmed to rt.

In a separate flask was added 6-bromo-1,2,4-triazin-3-amine (10.0 g, 57.5 mmol), (PPh₃)₄Pd (12.1 g, 11.5 mmol), and THF (200 mL). The mixture was heated to 80° C., followed by the dropwise addition (1 h) of (5-((tert-butyldimethylsilyloxy)methyl)thiazol-2-yl)zinc(II) bromide prepared in the step above. The reaction was then cooled to rt, filtered through a silica pad, concentrated, and then purified using silica gel chromatography to afford 6.7 g the title compound as a light yellow solid.

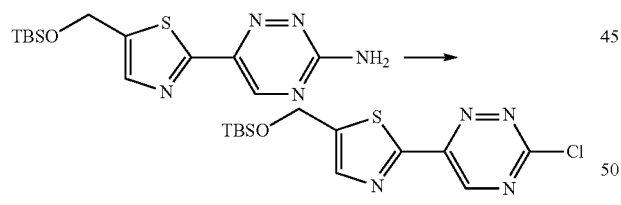

5-((tert-Butyldimethylsilyloxy)methyl)-2-(3-chloro-1,2,4-triazin-6-yl)thiazole

To a vial was added 6-(5-((tert-butyldimethylsilyloxy)methyl)thiazol-2-yl)-1,2,4-triazin-3-amine (2.5 g, 10.7 mmol), tetrabutylammonium chloride (6.3 g, 27.7 mmol) and dichloroethane (25 mL). The mixture was heated to 75° C., followed by the addition of t-butyl nitrite (3.3 mL, 27.7 mmol). The reaction was stirred at 75° C. for 3 h, followed by cooling to rt, quenching with brine (200 mL). The reaction was extracted four times with CH₂Cl₂. The combined organic layers were dried over Na₂SO₄, concentrated, and purified using silica gel chromatography to afford the 1.1 g of the title compound as an off-white solid.

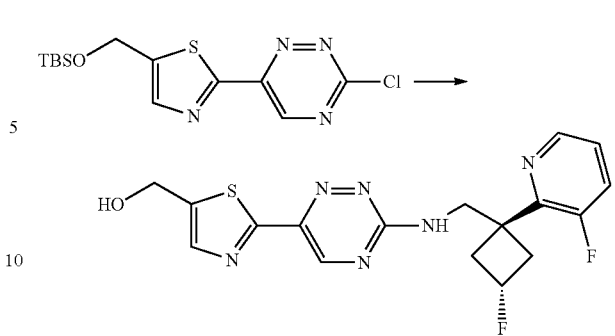

(2-(3-(((trans)-3-Fluoro-1-(3-fluoropyridin-2-yl) cyclobutyl)methylamino)-1,2,4-triazin-6-yl)thiazol-5-yl)methanol To a round bottom flask was added 5-((tert-butyldimethylsilyloxy)methyl)-2-(3-chloro-1,2,4-triazin-6-yl)thiazole (1.1 g, 3.2 mmol), trans-3-fluoro-1-(3-fluoropyridin-2-yl)cyclobutyl)methanamine (870 mg, 4.3 mmol), potassium carbonate (1.3 g, 9.4 mmol), and CH₃CN (11 mL). The reaction mixture was heated to 80° C. and stirred for 2 h. The reaction was then diluted with EtOAc, filtered, and concentrated. The crude residue was suspended in methanol and concentrated HCl (1 mL) was added. The reaction was stirred for 30 min and then concentrated. The crude oil was dissolved in ethyl acetate (50 mL) and washed twice with saturated sodium carbonate (50 mL). The organic layers were dried over Na₂SO₄, concentrated, and purified using silica gel chromatography to afford 470 mg of the title compound as an off-white solid.

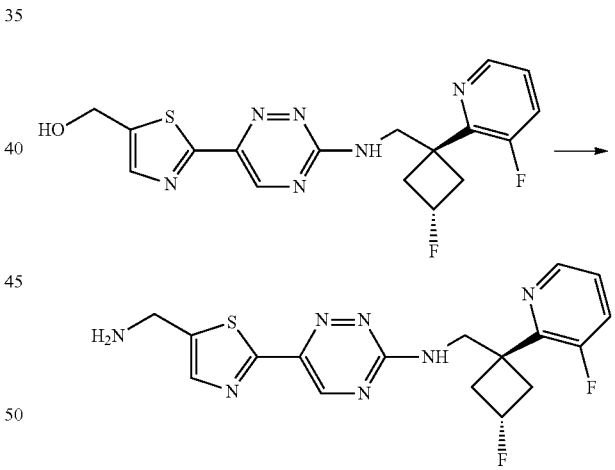

6-(5-(Aminomethyl)thiazol-2-yl)-N-(((trans)-3-fluoro-1-(3-fluoropyridin-2-yl)cyclobutyl)methyl)-1,2,4-triazin-3-amine To a vial containing (2-(3-(((trans)-3-fluoro-1-(3-fluoropyridin-2-yl)cyclobutyl)methylamino)-1,2,4-triazin-6-yl) thiazol-5-yl)methanol (457 mg, 1.17 mmol) was added triphenylphosphine (460 mg, 1.75 mmol), phthalimide (257 mg, 1.75 mmol), DIPEA (1 mL), and THF (10 mL). Diisopropylazodicarboxylate (350 mg, 1.75 mmol) was then added, and the reaction was stirred for 30 min. The reaction was quenched with saturated sodium bicarbonate solution (10 mL) and extracted three times with ethyl acetate (50 mL). The organic layers were dried over Na₂SO₄, concentrated, and purified using silica gel chromatography to afford 670 mg of 2-((2-(3-(((trans)-3-fluoro-1-(3-fluoropyridin-2-yl)cyclobutyl)methylamino)-1,2,4-triazin-6-yl)thiazol-5-yl)methyl)isoindoline-1,3-dione as an off-white solid. This solid was dissolved in methanol (10 mL) and hydrazine (1 mL). The reaction was stirred for 12 h, concentrated, and then purified using reverse phase chromatography to afford 250 mg of 6-(5-(aminomethyl)thiazol-2-yl)-N-(((trans)-3-fluoro-1-(3-fluoropyridin-2-yl)cyclobutyl)methyl)-1,2,4-triazin-3-amine.

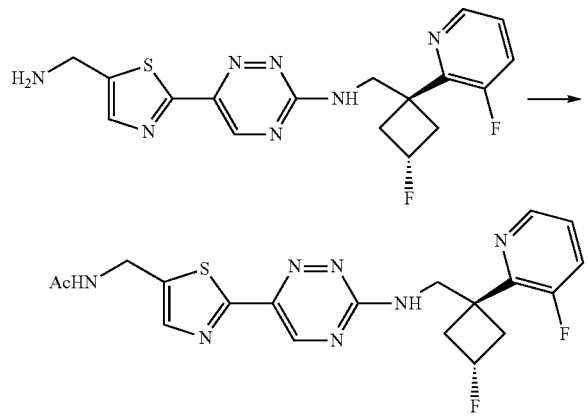

N-((2-(3-(((trans)-3-fluoro-1-(3-fluoropyridin-2-yl)cyclobutyl)methylamino)-1,2,4-triazin-6-yl)thiazol-5-yl)methyl)acetamide To a stirring solution of 6-(5-(aminomethyl)thiazol-2-yl)-N-(((trans)-3-fluoro-1-(3-fluoropyridin-2-yl)cyclobutyl)methyl)-1,2,4-triazin-3-amine (250 mg, 643 µmol) in CH₂Cl₂ (10 mL) was added acetic anhydride (324 mg, 3.2 µmol). The reaction was stirred for 30 min, followed by quenched with saturated sodium bicarbonate solution (10 mL) and extracted three times with CH₂Cl₂ (50 mL). The organic layers were dried over Na₂SO₄, concentrated, and purified using reverse phase chromatography to afford 224 mg of N-((2-(3-(((trans)-3-fluoro-1-(3-fluoropyridin-2-yl)cyclobutyl)methylamino)-1,2,4-triazin-6-yl)thiazol-5-yl)methyl)acetamide as a white solid, m/z=432.1 [M+H].

EXAMPLE 23

Preparation of 2-(3-(2-(3-(difluoromethoxy)pyridin-2-yl)propan-2-ylamino)-1,2,4-triazin-6-yl)thiazole-5-carboxamide

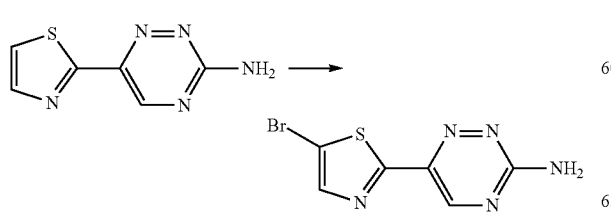

6-(5-Bromothiazol-2-yl)-1,2,4-triazin-3-amine

To a vial was added 6-(thiazol-2-yl)-1,2,4-triazin-3-amine (600 mg, 3.4 mmol), methanol (1.2 mL), water (0.6 mL). The mixture was cooled to 0° C. and bromine (816 mg, 5.1 mmol) was added. The reaction was stirred for 45 min and then quenched with saturated sodium bicarbonate solution (20 mL) and extracted three times with ethyl acetate (50 mL). The organic layers were dried over Na₂SO₄, concentrated, and purified using silica gel chromatography to afford 320 mg of 6-(5-bromothiazol-2-yl)-1,2,4-triazin-3-amine as an off-white solid.

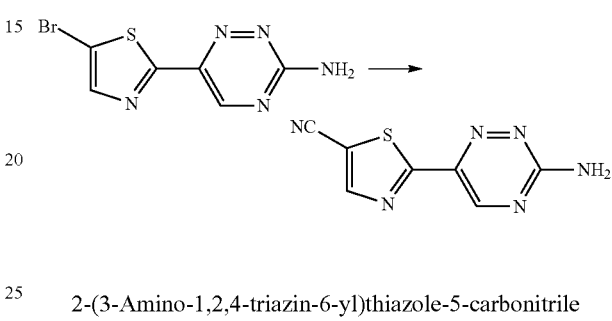

2-(3-Amino-1,2,4-triazin-6-yl)thiazole-5-carbonitrile 6-(5-Bromothiazol-2-yl)-1,2,4-triazin-3-amine (300 mg, 1.15 mmol), zinc cyanide (340 mg, 2.30 mmol), Pd(PPh₃)₄ (133 mg, 0.13 mmol), and DMF (5 mL) were combined and heated to 160° C. for 12 h. The reaction mixture was cooled, diluted with CH₂Cl₂ (30 mL), filtered through silica gel, eluted with EtOAc, and concentrated. The crude product was then purified using silica gel chromatography to afford 30 mg of 2-(3-amino-1,2,4-triazin-6-yl)thiazole-5-carbonitrile.

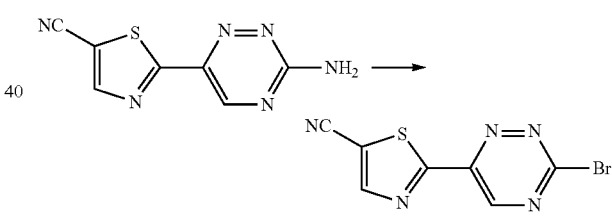

2-(3-Bromo-1,2,4-triazin-6-yl)thiazole-5-carbonitrile 2-(3-Amino-1,2,4-triazin-6-yl)thiazole-5-carbonitrile (30 mg, 0.15 mmol) was dissolved in 1 mL of bromoform and heated to 90° C. Isoamyl nitrite (88 mg, 0.75 mmol) was added and stirred at 90° C. for 2 h. The reaction mixture was then concentrated and used directly in the next reaction.

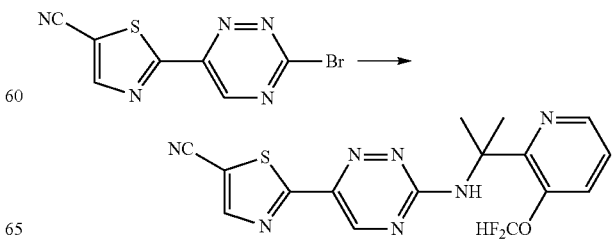

2-(3-(2-(3-(Difluoromethoxy)pyridin-2-yl)propan-2-ylamino)-1,2,4-triazin-6-yl)thiazole-5-carbonitrile To a scintillation vial was added 2-(3-bromo-1,2,4-triazin-6-yl)thiazole-5-carbonitrile (directly from above reaction), 2-(3-(difluoromethoxy)pyridin-2-yl)propan-2-amine (100 mg, 500 µmol), and CH$_3$CN (2 mL). The reaction was heated to 90° C. and stirred for 12 h. The reaction was then concentrated and purified using silica gel chromatography to afford 15 mg of 2-(3-(2-(3-(difluoromethoxy)pyridin-2-yl)propan-2-ylamino)-1,2,4-triazin-6-yl)thiazole-5-carbonitrile.

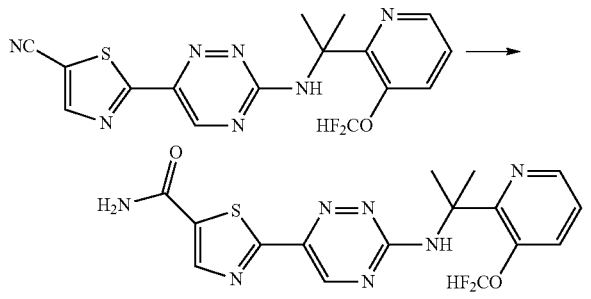

2-(3-(2-(3-(Difluoromethoxy)pyridin-2-yl)propan-2-ylamino)-1,2,4-triazin-6-yl)thiazole-5-carboxamide 2-(3-(2-(3-(difluoromethoxy)pyridin-2-yl)propan-2-ylamino)-1,2,4-triazin-6-yl)thiazole-5-carbonitrile (15 mg, 38 µmol), K$_2$CO$_3$ (50 mg, 0.35 mmol), and DMSO (1 mL) were combined in a vial and cooled to 0° C. H$_2$O$_2$ (0.1 mL of 35% solution) was then added and the reaction was warmed to rt and stirred for 1 h. Acetic acid (0.1 mL) was added, and the reaction was filtered and then purified using reverse phase chromatography to afford 23 mg of 2-(3-(2-(3-(difluoromethoxy)pyridin-2-yl)propan-2-ylamino)-1,2,4-triazin-6-yl)thiazole-5-carboxamide as a white solid, m/z=408.3 [M+H].

EXAMPLE 24

Preparation of 3-(5-Fluoro-6-(((trans)-3-fluoro-1-(3-fluoropyridin-2-yl)cyclobutyl)methylamino)pyridin-3-yl)benzamide

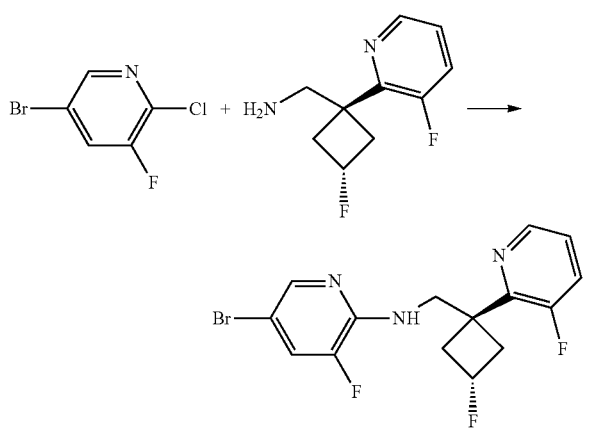

5-Bromo-3-fluoro-N-(((trans)-3-fluoro-1-(3-fluoropyridin-2-yl)cyclobutyl)methyl)pyridin-2-amine To a microwave tube was added 5-bromo-2-chloro-3-fluoropyridine (1.5 g, 7.4 mmol), ((trans)-3-fluoro-1-(3-fluoropyridin-2-yl)cyclobutyl)methanamine (2.2 g, 11.1 mmol), and DIPEA (4.9 mL, 29.7 mmol). The tube was sealed, heated at 110° C., and stirred for 12 h. The reaction was then directly purified using silica gel chromatography to afford 2.5 g of 5-bromo-3-fluoro-N-(((trans)-3-fluoro-1-(3-fluoropyridin-2-yl)cyclobutyl)methyl)pyridin-2-amine as a white solid.

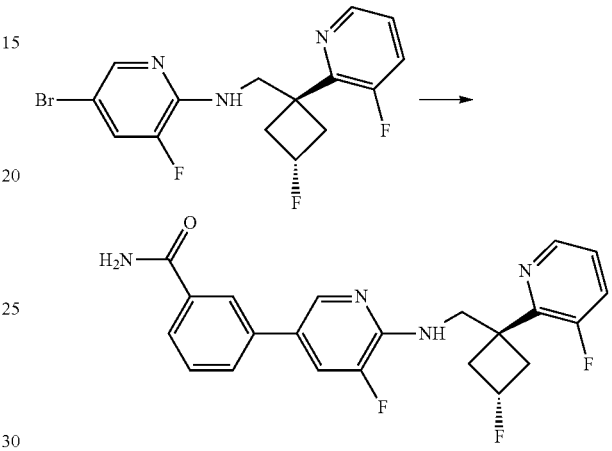

3-(5-Fluoro-6-(((trans)-3-fluoro-1-(3-fluoropyridin-2-yl)cyclobutyl)methylamino)pyridin-3-yl)benzamide 5-Bromo-3-fluoro-N-(((trans)-3-fluoro-1-(3-fluoropyridin-2-yl)cyclobutyl)methyl)pyridin-2-amine (1.0 g, 2.6 mmol), 3-carbamoylphenylboronic acid (0.54 g, 3.2 mmol), potassium carbonate (1.5 g, 10.8 mmol), and methanol (25 mL) was added to a 100 mL round bottom flask and then degassed with nitrogen for 5 min. Silica-supported 1,1'-Bis(diphenylphosphino)ferrocene (1.0 g, 0.28 mmol/g) was added, and the reaction was refluxed in methanol for 2 h. The reaction mixture was then filtered, concentrated, and purified using silica gel chromatography to afford 2.0 g of the title compound as a solid, m/z=413.3 [M+H].

EXAMPLE 25

Preparation and Assay of Fast Skeletal Myofibrils

Preparation of Fast Skeletal Myofibrils
Rabbit skeletal myofibrils were prepared based upon the method of Herrmann et al. (Biochem. 32(28):7255-7263 (1993). Myofibrils were prepared from rabbit psoas muscle purchased from Pel-Freez Biologicals (Arkansas) within 2 days of ordering, stored on ice. Minced muscle was homogenized in 10 volumes of ice-cold "standard" buffer (50 mM Tris, pH 7.4, 0.1 M potassium acetate, 5 mM KCl, 2 mM DTT, 0.2 mM PMSF, 10 µM leupeptin, 5 µM pepstatin, and 0.5 mM sodium azide) containing 5 mM EDTA and 0.5% Triton X-100 using an Omni-Macro homogenizer. Myofibrils were recovered by low speed centrifugation (3000 rpm for 10 minutes) and washed 2 times in the Triton X-100 containing buffer to ensure removal of cellular membrane. Following the Triton washes, myofibrils were washed 3 times in "standard"

buffer containing 2 mM magnesium acetate. A final wash in assay buffer (12 mM PIPES, pH 6.8, 60 mM KCl, 1 mM DTT) was performed and brought to 10% sucrose for flash freezing in liquid nitrogen and storage at −80° C.

Activation of Fast Skeletal Myofibrils.

Fast fiber activators were identified by measuring the enzymatic activity of muscle myofibril preparations using the proprietary PUMA™ (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been mechanically homogenized and washed with a detergent (triton X-100) to remove cellular membranes. This preparation retained all of the sarcomeric components in a native conformation and the enzymatic activity was still regulated by calcium. Compounds were tested using a myofibril suspension and a level of calcium sufficient to increase enzymatic activity of the myofibrils to 25% of their maximal rate (termed pCa25). Enzymatic activity was tracked via a pyruvate kinase and lactate dehydrogenase-coupled enzyme system. This assay regenerates myosin-produced ADP into ATP by oxidizing NADH, producing an absorbance change at 340 nm. The buffering system was 12 mM Pipes, 2 mM $MgCl_2$, 1 mM DTT at pH 6.8 (PM12 buffer). Data was reported as AC1.4, which is the concentration at which the compound increased the enzymatic activity by 40%. The results are summarized in Table 2 below.

EXAMPLE 26

Preparation and Assay of Sarcomeric Proteins from Skeletal Muscle

Powder Preparation
1. Volumes are given per about 1000 g of the minced muscle.
2. Pre-cut and boil cheesecloth for 10 min in water. Drain and dry.
3. Mince chicken breast in a prechilled meat grinder.
4. Extract with stirring in 2 L of 0.1 M KCl, 0.15 M K-phosphate, pH 6.5 for 10 min at 4° C. Spin 5000 rpm, 10 min, 4° C. in JLA. Collect the pellet.
5. Extract pellets with stirring with 2 L of 0.05 M $NaHCO_3$ for 5 min. Spin 5000 rpm, 10 min, 4° C. in JLA. Collect the pellet. Repeat the extraction once more.
6. Extract the filtered residue with 2 L of 1 mM EDTA, pH 7.0 for 10 min with stirring.
7. Extract with 2 L of $H_2O$ for 5 min with stirring. Spin 10000 rpm, 15 min, 4° C. in JLA. Carefully collect the pellet, part of which will be loose and gelatinous.
8. Extract 5 times with acetone (2 L of acetone for 10 min each with stirring). Squeeze through cheesecloth gently. All acetone extractions are performed at room temperature. Acetone should be prechilled to 4° C.
9. Drying: Place the filtered residue spread on a cheesecloth in a large glass tray and leave in a hood overnight. When the residue is dry, put in a wide mouth plastic bottle and store at 20° C.

Alternate Powder Preparation
(See Zot & Potter (1981) Prep. Biochem. 11(4) pp. 381-395)
1. Dissect left ventricles of the cardiac muscle. Remove as much of the pericardial tissue and fat as possible. Grind in a prechilled meat grinder. Weigh.
2. Prepare 5 volumes of Extract buffer (see below). Homogenize the meat in a blender, 4 times 15 sec on blend with 15 secs in between. Do this with 1 volume (weight/volume) of buffer taken from the 5 volumes already prepared. Add the homogenate back to the extract buffer and stir until well mixed (5 minutes).
3. Filter through one layer of cheesecloth in large polypropylene strainer. Resuspend back into 5 volumes of extract buffer as above.
4. Repeat Step 3 four more times. At the end, do not resuspend in extraction buffer but proceed to Step 5. The pellets should be yellow white.
5. Resuspend in 3 volumes (according to original weight) of 95% cold ethanol. Stir for 5 min and squeeze through cheesecloth as above, repeat two more times.
6. Weigh squeezed residue and then resuspend in 3 volumes (new weight/volume) of cold diethyl ether.
7. Repeat Step 6a total of three times.
8. Leave overnight in a single layer on a cheesecloth in a glass tray.
9. When dry, collect the powder, weigh and store in a wide-mouth jar at 4° C.

EXTRACT BUFFER: 50 mM KCl, 5 mM Tris pH 8.0 Prepare as 50 times concentrate. For 2 L: 250 mM Tris pH 8.0. Tris Base (121.14 g/mol, 60.6 g), pH to 8.0 with conc. HCl, then add 2.5 M KCl (74.55 g/mol, 372 g).

Actin Preparation
1. Extract powder (as described above) with 20 ml buffer A (see below, add BME and ATP just prior to use in each of the following steps) per gram of powder (200 ml per 10 g). Use a large 4 L beaker for 150 g of powder. Mix vigorously to dissolve powder. Stir at 4° C. for 30 min.
2. Separate extract from the hydrated powder by squeezing through several layers of cheesecloth. Cheesecloth should be pre-sterilized by microwaving damp for 1-2 min.
3. Re-extract the residue with the same volume of buffer A and combine extracts.
4. Spin in JLA10 rotor(s) for 1 hr at 10K rpm (4° C.). Collect supernatant through 2 layers of cheesecloth.
5. Add ATP to 0.2 mM and $MgCl_2$ to 50 mM. Stir on stir plate at 4° C. for 60 minutes to allow actin to polymerize/form para-crystals.
6. Slowly add solid KCl to 0.6 M (45 g/l). Stir at 4° C. for 30 min.
7. Spin in JLA10 rotor(s) at 10K rpm for 1 hr.
8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.
9. Dialyze against buffer A with 4 changes over 48 hour period.
10. Collect dialyzed actin and spin in the 45Ti rotor at 40K rpm for 1.5 hr (4° C.).
11. Collect supernatant (G-Actin). Save a sample for gel analysis and determination of protein concentration.
12. To polymerize G-actin for storage, add KCl to 50 mM (from 3 M stock), $MgCl_2$ to 1 mM, and $NaN_3$ to 0.02% (from 10% stock). Store at 4° C. Do not freeze.

Buffer A: 2 mM tris/HCl, 0.2 mM $CaCl_2$, 0.5 mM (36 µl/L) 2-mercaptoethanol, 0.2 mM $Na_2$ ATP (added fresh), and 0.005% Na-azide; pH 8.0.

Purification of Skeletal Muscle Myosin
(See Margossian, S. S. and Lowey, S. (1982) Methods Enzymol. 85, 55-123; and Goldmann, W. H. and Geeves, M. A. (1991) Anal. Biochem. 192, 55-58)

Solution A: 0.3 M KCl, 0.15 M potassium phosphate, 0.02 M EDTA, 0.005 M MgCl$_2$, 0.001 M ATP, pH 6.5.
Solution B: 1 M KCl, 0.025 M EDTA, 0.06 M potassium phosphate, pH 6.5.
Solution C: 0.6 M KCl, 0.025 M potassium phosphate, pH 6.5.
Solution D: 0.6 M KCl, 0.05 M potassium phosphate, pH 6.5.
Solution E: 0.15 M potassium phosphate, 0.01 M EDTA, pH 7.5.
Solution F: 0.04 M KCl, 0.01 M potassium phosphate, 0.001 M DTT, pH 6.5.
Solution G: 3 M KCl, 0.01 M potassium phosphate, pH 6.5.
All procedures are carried out at 4° C.

1. Obtain approx. 1000 g skeletal muscle, such as rabbit skeletal muscle.
2. Grind twice; extract with 2 L solution A for 15 min while stirring; add 4 L cold H$_2$O, filter through gauze; dilute with cold H$_2$O to ionic strength of 0.04, (about 10-fold); let settle for 3 h; collect precipitate at 7,000 rpm in GSA rotor for 15 min.
3. Disperse pellet in 220 ml solution B; dialyze overnight against 6 L solution C; slowly add ~400 ml equal volume cold distilled H$_2$O; stir for 30 min; centrifuge at 10,000 rpm for 10 min in GSA rotor.
4. Centrifuge supernatant at 19,000 rpm for 1 h.
5. Dilute supernatant to ionic strength of 0.04 (~8-fold); let myosin settle overnight; collect about 5-6 L fluffy myosin precipitate by centrifuging at 10,000 rpm for 10 min in GSA rotor.
6. Resuspend pellet in minimal volume of solution G; dialyze overnight against 2 L solution D; centrifuge at 19,000 rpm for 2 h, in cellulose nitrate tubes; puncture tubes and separate myosin from fat and insoluble pellet.
7. Dilute supernatant to 5-10 mg/ml and dialyze against solution E extensively, load onto DEAE-sephadex column.
8. Pre-equilibrate with solution E; apply 500-600 g myosin at 30 ml/h; wash with 350 ml solution E; elute with linear gradient of 0-0.5 M KCl in solution E (2×1 liter); collect 10 ml fractions; pool myosin fractions (>0.1 M KCl); concentrate by overnight dialysis against solution F; centrifuge at 25,000 rpm for 30 min; store as above.
9. The myosin is then cut with chymotrypsin or papain in the presence of EDTA to generate the S1 fragment which is soluble at the low salt conditions optimal for ATPase activity (Margossian, supra).

Preparation and Assay

Myosin is prepared by precipitation from salt extracts of rabbit psoas muscle, and a soluble S1 fraction is prepared by digestion with chymotrypsin (Margossian and Lowey, 1982).

Actin is purified by first preparing an ether powder of cardiac muscle (Zot H G and Potter J D. (1981) Preparative Biochemistry 11:381-395) as described above. Subsequently, actin is cycled between the filamentous and soluble state through rounds of centrifugation and dialysis (Spudich J A and Watt S. (1971) J. Biol. Chem. 246:4866-4871).

Tropomyosin is extracted from the ether powder and separated from the other proteins based on pH dependent precipitations followed by successive ammonium sulfate cuts at 53% and 65% (Smillie L B. (1981) Methods Enzymol 85 Pt B:234-41). The troponins are isolated as an intact complex of TnC, TnT, and TnI. Ether powder is extracted in a high salt buffer. Successive ammonium sulfate cuts of 30% and 45% are done; the precipitate is solubilized by dialysis into a low salt buffer and then further purified on a DEAE Toyopearl column with a 25-350 mM KCl gradient. There is no measurable ATPase in any of the components except for myosin which naturally had a very low basal ATPase in the absence of actin.

Prior to screening, the actin, tropomyosin, and troponin complex are mixed together in the desired ratio (e.g., 7:1:1) to achieve maximal calcium regulation of the actin filament. The screen is conducted at a concentration that gives 25% activation. This calcium concentration is in the physiological range during muscle contraction.

To measure the generation of ADP during the reaction, a pyruvate kinase/lactate dehydrogenase/NADH coupled enzyme system (PK/LDH) is added to the actin. The myosin is kept separately, and added to the regulated thin filaments to initiate the reaction. Oxidation of NADH is monitored in real time, so that kinetic curves are obtained. Compounds are dissolved in DMSO and spotted onto the bottoms of 384 well plates at 10 to 40 µg/ml final concentration.

Using procedures similar to those described herein, utilizing reagents and intermediates commercially available (e.g., Sigma-Aldrich) or readily synthesized by one of skill in the art, the compounds in Table 2 were synthesized, characterized and tested. AC1.4 values were determined according to the procedure described in Example 25, and the reported median AC1.4 values are as follows: A=<1 uM; B=1-10 uM; C=10-20 uM; D=>20 uM.

TABLE 2

| Compound | Structure | m/z (M + H) | Mean AC1.4 |
|---|---|---|---|
| (6-bromo(2-pyridyl))[2-(4-fluorophenyl)-2-methylpropyl]amine | 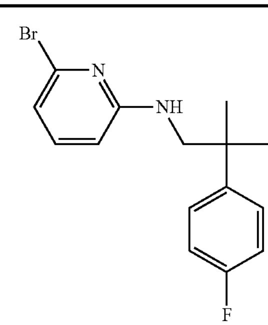 | 323.0 | C |

TABLE 2-continued

| Compound | Structure | m/z (M + H) | Mean AC1.4 |
|---|---|---|---|
| [2-(4-fluorophenyl)-2-methylpropyl][6-(2-methylprop-1-enyl)(2-pyridyl)]amine | 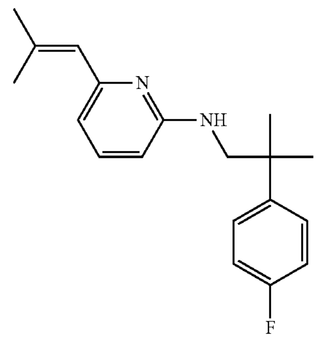 [SMILES: CC(C)=Cc1cccc(NCC(C)(C)c2ccc(F)cc2)n1] | 299.4 | D |
| [6-(4-fluorophenyl)(2-pyridyl)][2-(4-fluorophenyl)-2-methylpropyl]amine | 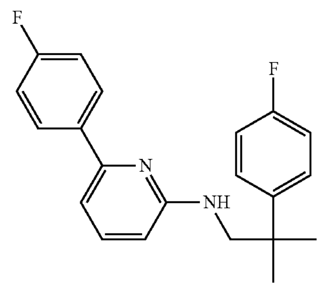 [SMILES: CC(C)(CNc1cccc(-c2ccc(F)cc2)n1)c1ccc(F)cc1] | 339.1 | D |
| [4-(4-fluorophenyl)(2-pyridyl)][2-(4-fluorophenyl)-2-methylpropyl]amine | 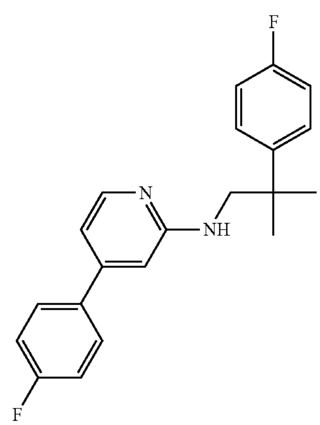 [SMILES: CC(C)(CNc1cc(-c2ccc(F)cc2)ccn1)c1ccc(F)cc1] | 339.1 | D |
| 4-(6-{[2-(4-fluorophenyl)-2-methylpropyl]amino}-3-pyridyl)benzamide | 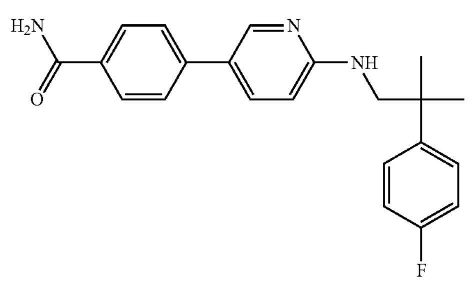 [SMILES: CC(C)(CNc1ccc(-c2ccc(C(N)=O)cc2)cn1)c1ccc(F)cc1] | 364.0 | B |
| 3-(6-{[2-(4-fluorophenyl)-2-methylpropyl]amino}-3-pyridyl)benzamide | 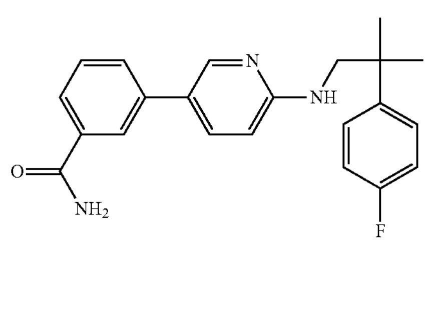 [SMILES: CC(C)(CNc1ccc(-c2cccc(C(N)=O)c2)cn1)c1ccc(F)cc1] | 364.0 | A |

TABLE 2-continued

| Compound | Structure | m/z (M + H) | Mean AC1.4 |
|---|---|---|---|
| 6-{[2-(4-fluorophenyl)-2-methylpropyl]amino}pyridine-3-carbonitrile | 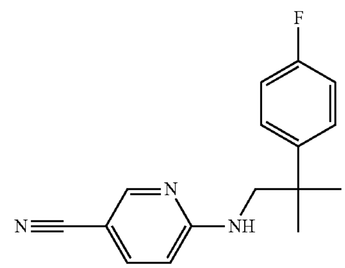 [SMILES: CC(C)(CNc1ccc(C#N)cn1)c1ccc(F)cc1] | 270.1 | C |
| 3-(6-{[2-(4-fluorophenyl)ethyl]amino}-3-pyridyl)benzamide | 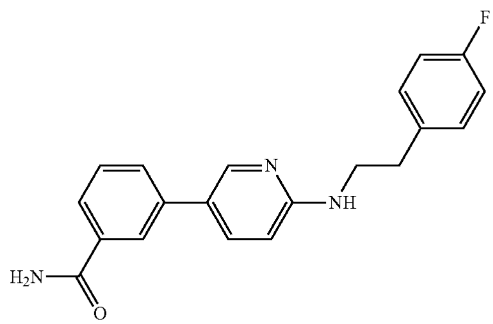 [SMILES: NC(=O)c1cccc(-c2ccc(NCCc3ccc(F)cc3)nc2)c1] | 336.1 | D |
| 6-{[2-(4-fluorophenyl)-2-methylpropyl]amino}pyridine-3-carboxamide | 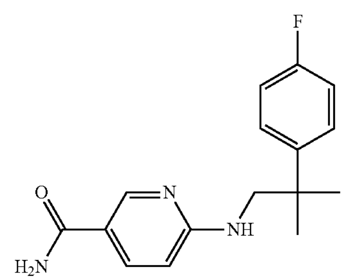 [SMILES: CC(C)(CNc1ccc(C(N)=O)cn1)c1ccc(F)cc1] | 288.1 | C |
| N-[(6-{[2-(4-fluorophenyl)-2-methylpropyl]amino}(3-pyridyl))methyl]methoxycarboxamide | 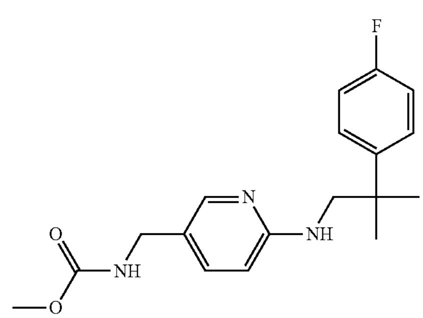 [SMILES: COC(=O)NCc1ccc(NCC(C)(C)c2ccc(F)cc2)nc1] | 332.0 | D |
| tert-butyl 2-[(5-bromo-2-pyridyl)amino]acetate | 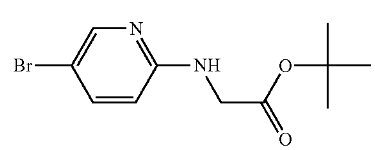 [SMILES: CC(C)(C)OC(=O)CNc1ccc(Br)cn1] | 288.0 | D |

TABLE 2-continued

| Compound | Structure | m/z (M + H) | Mean AC1.4 |
|---|---|---|---|
| 3-{6-[2-(4-fluorophenyl)acetylamino]-3-pyridyl}benzamide | 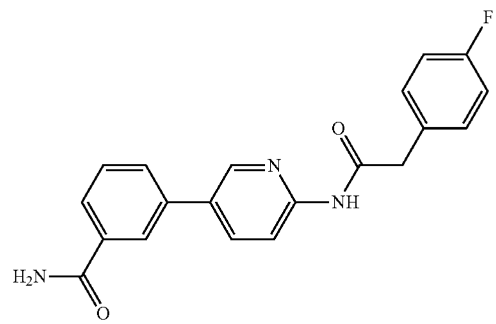 [SMILES: NC(=O)c1cccc(-c2ccc(NC(=O)Cc3ccc(F)cc3)nc2)c1] | 350.1 | D |
| 1-(6-{[2-(4-fluorophenyl)-2-methylpropyl]amino}-3-pyridyl)ethane-1,2-diol | 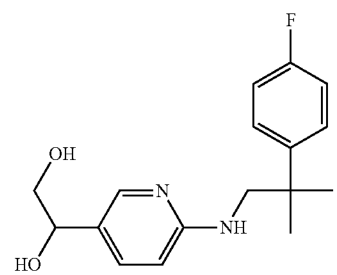 [SMILES: CC(C)(CNc1ccc(C(O)CO)cn1)c1ccc(F)cc1] | 305.0 | D |
| 3-(6-{[(2S)-2-(4-fluorophenyl)propyl]amino}-3-pyridyl)benzamide | 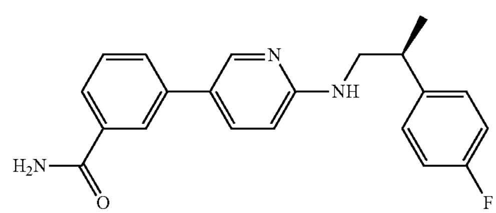 [SMILES: C[C@H](CNc1ccc(-c2cccc(C(N)=O)c2)cn1)c1ccc(F)cc1] | 350.0 | B |
| 3-(6-{[(2R)-2-(4-fluorophenyl)propyl]amino}-3-pyridyl)benzamide | 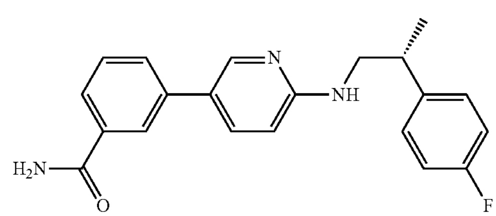 [SMILES: C[C@@H](CNc1ccc(-c2cccc(C(N)=O)c2)cn1)c1ccc(F)cc1] | 350.0 | B |
| 3-(6-{[2-(4-fluorophenyl)-2-methylpropyl]amino}-3-pyridyl)propane-1,2-diol | 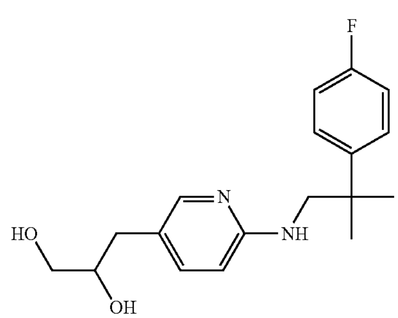 [SMILES: CC(C)(CNc1ccc(CC(O)CO)cn1)c1ccc(F)cc1] | 319.0 | D |

TABLE 2-continued

| Compound | Structure | m/z (M + H) | Mean AC1.4 |
|---|---|---|---|
| N-[2-(6-{[2-(4-fluorophenyl)-2-methylpropyl]amino}(3-pyridyl))ethyl]methoxycarboxamide | 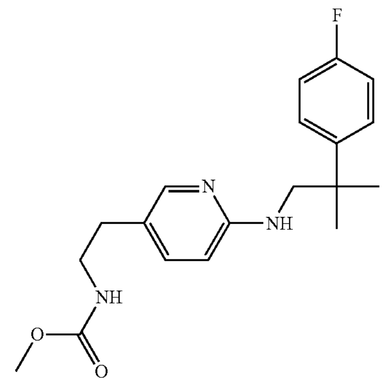 [SMILES: COC(=O)NCCc1ccc(NCC(C)(C)c2ccc(F)cc2)nc1] | 346.0 | D |
| [2-(6-{[2-(4-fluorophenyl)-2-methylpropyl]amino}(3-pyridyl)ethyl](methylsulfonyl)amine | 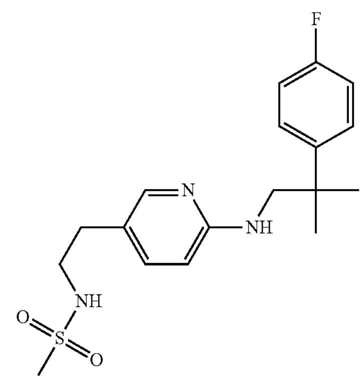 [SMILES: CC(C)(CNc1ccc(CCNS(C)(=O)=O)cn1)c1ccc(F)cc1] | 366.0 | D |
| N-[2-(6-{[2-(4-fluorophenyl)-2-methylpropyl]amino}-3-pyridyl)ethyl]acetamide | 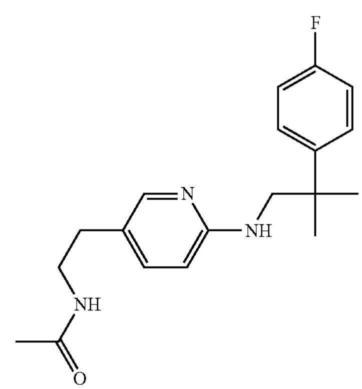 [SMILES: CC(=O)NCCc1ccc(NCC(C)(C)c2ccc(F)cc2)nc1] | 330.0 | D |
| 2-{[2-(4-fluorophenyl)-2-methylpropyl]amino}quinoline-6-carboxamide | 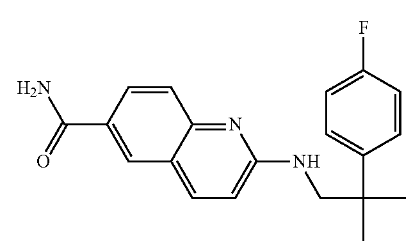 [SMILES: CC(C)(CNc1ccc2cc(C(N)=O)ccc2n1)c1ccc(F)cc1] | 338.1 | B |

TABLE 2-continued

| Compound | Structure | m/z (M + H) | Mean AC1.4 |
|---|---|---|---|
| (4-phenyl(2-pyridyl))(phenylcyclobutyl)amine | 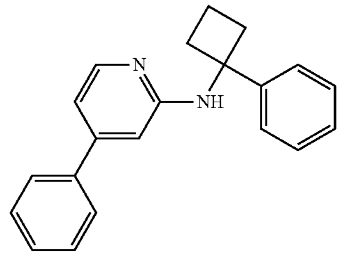 [SMILES: c1ccc(-c2ccnc(NC3(c4ccccc4)CCC3)c2)cc1] | 301.2 | C |
| (6-phenyl(2-pyridyl))(phenylcyclobutyl)amine | 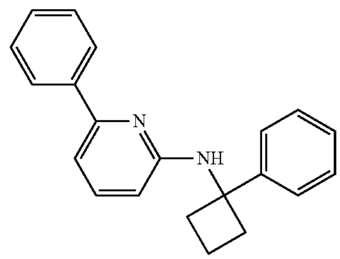 [SMILES: c1ccc(-c2cccc(NC3(c4ccccc4)CCC3)n2)cc1] | 301.2 | D |
| (5-phenyl(2-pyridyl))(phenylcyclobutyl)amine | 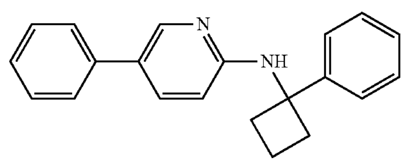 [SMILES: c1ccc(-c2ccc(NC3(c4ccccc4)CCC3)nc2)cc1] | 301.2 | B |
| 3-[5-fluoro-6-({[3-fluoro-1-(3-fluoro(2-pyridyl))cyclobutyl]methyl}amino)-3-pyridyl]benzamide | 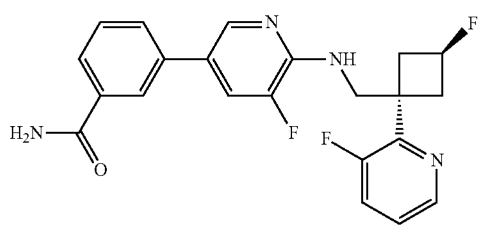 [SMILES: NC(=O)c1cccc(-c2cnc(NC[C@]3(c4ncccc4F)C[C@H](F)C3)c(F)c2)c1] | 413.3 | B |
| 3-(3-{[2-(4-fluorophenyl)-2-methylpropyl]amino}-1,2,4-triazin-6-yl)benzamide | 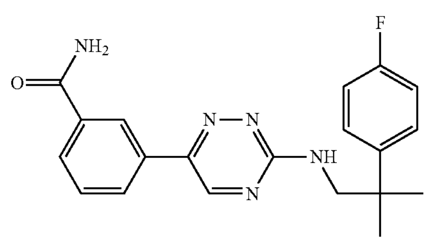 [SMILES: CC(C)(CNc1ncc(-c2cccc(C(N)=O)c2)nn1)c1ccc(F)cc1] | 366.1 | B |
| [6-(3-amino(1H-indazol-5-yl))(1,2,4-triazin-3-yl)][2-(4-fluorophenyl)-2-methylpropyl]amine | 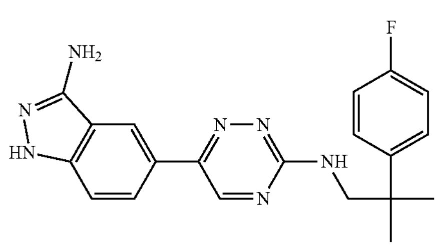 [SMILES: CC(C)(CNc1ncc(-c2ccc3[nH]nc(N)c3c2)nn1)c1ccc(F)cc1] | 378.1 | A |

TABLE 2-continued

| Compound | Structure | m/z (M + H) | Mean AC1.4 |
|---|---|---|---|
| 3-(6-{[2-(4-fluorophenyl)-2-methylpropyl]amino}-1,2,4-triazin-3-yl)benzamide | 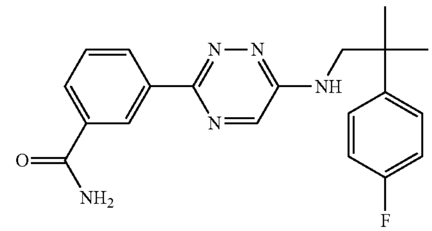 [SMILES: CC(C)(CNc1cnc(-c2cccc(C(N)=O)c2)nn1)c1ccc(F)cc1] | 366.1 | B |
| 3-[6-({[(4-fluorophenyl)cyclobutyl]methyl}amino)-1,2,4-triazin-3-yl]benzamide | 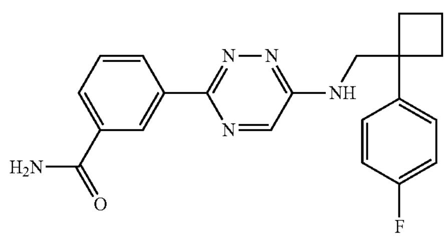 [SMILES: NC(=O)c1cccc(-c2ncc(NCC3(c4ccc(F)cc4)CCC3)nn2)c1] | 378.1 | A |
| 2-fluoro-5-(3-{[2-(4-fluorophenyl)-2-methylpropyl]amino}(1,2,4-triazin-6-yl))benzamide | 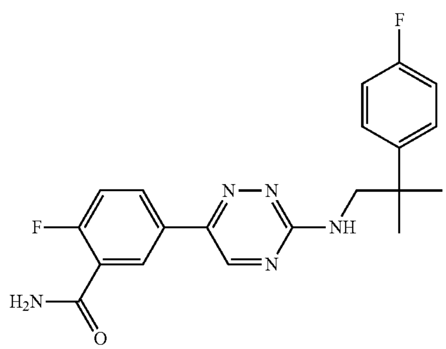 [SMILES: CC(C)(CNc1ncc(-c2ccc(F)c(C(N)=O)c2)nn1)c1ccc(F)cc1] | 369.1 | D |
| 2-fluoro-5-[3-({[(3-fluoro(2-pyridyl))cyclobutyl]methyl}amino)(1,2,4-triazin-6-yl)]benzenecarbonitrile | 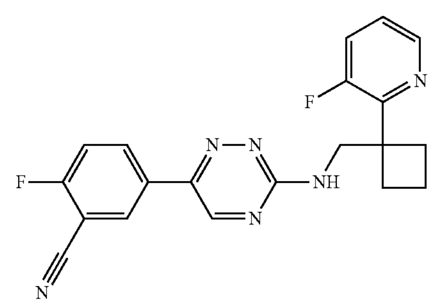 [SMILES: N#Cc1cc(-c2cnc(NCC3(c4ncccc4F)CCC3)nn2)ccc1F] | 379.1 | C |
| (6-(1H-indazol-5-yl)(1,2,4-triazin-3-yl)){[(3-fluoro(2-pyridyl))cyclobutyl]methyl}amine | 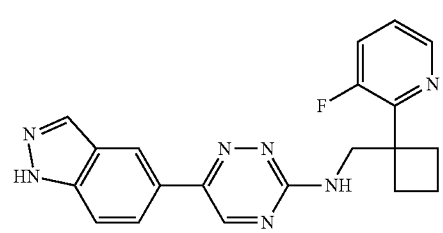 [SMILES: Fc1cccnc1C1(CNc2ncc(-c3ccc4[nH]ncc4c3)nn2)CCC1] | 376.1 | B |
| [6-(3-amino(1H-indazol-5-yl))(1,2,4-triazin-3-yl)]{[(3-fluoro(2-pyridyl))cyclobutyl]methyl}amine | 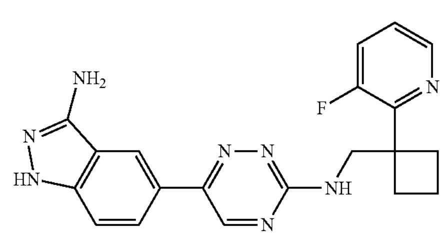 [SMILES: Nc1n[nH]c2ccc(-c3cnc(NCC4(c5ncccc5F)CCC4)nn3)cc12] | 391.1 | B |

TABLE 2-continued

| Compound | Structure | m/z (M + H) | Mean AC1.4 |
|---|---|---|---|
| (6-(1H-indazol-5-yl)(1,2,4-triazin-3-yl))[2-(3-fluoro(2-pyridyl))-2-methylpropyl]amine | 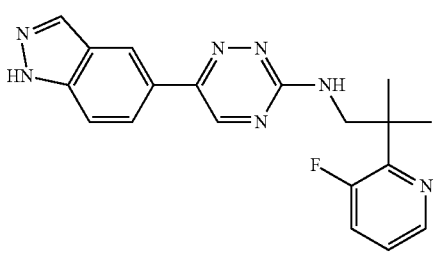 [SMILES: CC(C)(CNc1ncc(-c2ccc3[nH]ncc3c2)nn1)c1ncccc1F] | 364.2 | C |
| 4-fluoro-3-(3-{[(3-fluoro(2-pyridyl))cyclobutyl]amino}(1,2,4-triazin-6-yl))benzamide | 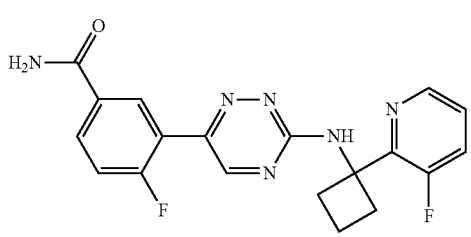 [SMILES: NC(=O)c1ccc(F)c(-c2cnc(NC3(c4ncccc4F)CCC3)nn2)c1] | 383.2 | B |
| 3-{3-[(tert-butyl)amino](1,2,4-triazin-6-yl)}-4-fluorobenzamide | 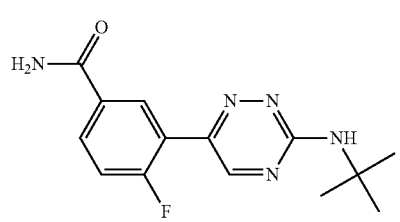 [SMILES: CC(C)(C)Nc1ncc(-c2cc(C(N)=O)ccc2F)nn1] | 290.1 | D |
| 4-fluoro-3-(3-{[(4-fluorophenyl)cyclobutyl]amino}(1,2,4-triazin-6-yl))benzamide | 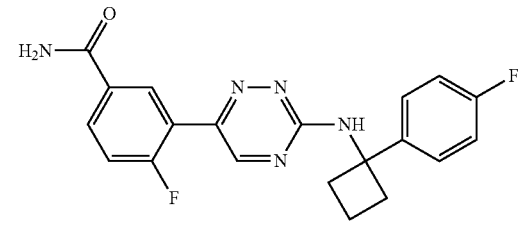 [SMILES: NC(=O)c1ccc(F)c(-c2cnc(NC3(c4ccc(F)cc4)CCC3)nn2)c1] | 382.1 | B |
| 4-fluoro-3-(3-{[1-(4-fluorophenyl)-isopropyl]amino}(1,2,4-triazin-6-yl))benzamide | 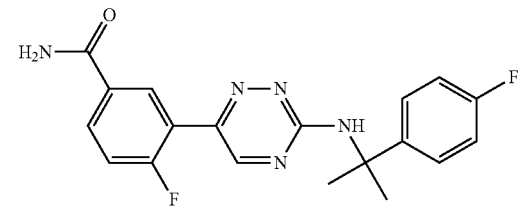 [SMILES: CC(C)(Nc1ncc(-c2cc(C(N)=O)ccc2F)nn1)c1ccc(F)cc1] | 370.2 | A |
| 3-[3-({[6-(difluoromethoxy)(2-pyridyl)]cyclobutyl}amino)(1,2,4-triazin-6-yl)]-4-fluorobenzamide | 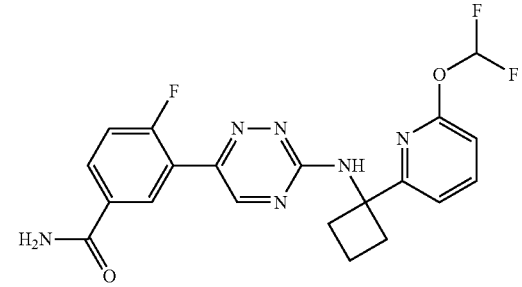 [SMILES: NC(=O)c1ccc(F)c(-c2cnc(NC3(c4cccc(OC(F)F)n4)CCC3)nn2)c1] | 431.1 | A |

TABLE 2-continued

| Compound | Structure | m/z (M + H) | Mean AC1.4 |
|---|---|---|---|
| [6-(4-bromophenyl)(1,2,4-triazin-3-yl)]{[(3-fluoro(2-pyridyl))cyclobutyl]methyl}amine | 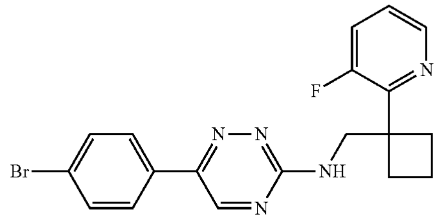 [SMILES: Fc1cccnc1C1(CNc2ncc(-c3ccc(Br)cc3)nn2)CCC1] | 415.1 | C |
| 3-[3-({1-[6-(difluoromethoxy)(2-pyridyl)]-isopropyl}amino)(1,2,4-triazin-6-yl)]-4-fluorobenzamide | 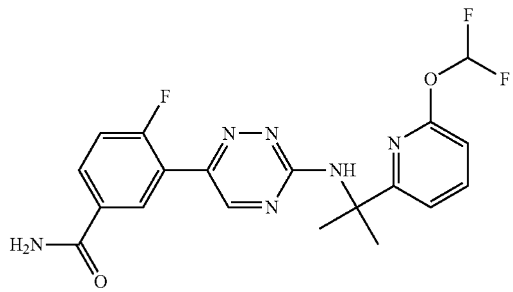 [SMILES: CC(C)(Nc1ncc(-c2cc(C(N)=O)ccc2F)nn1)c1cccc(OC(F)F)n1] | 419.1 | A |
| [6-(4-aminophenyl)(1,2,4-triazin-3-yl)]{[(3-fluoro(2-pyridyl))cyclobutyl]methyl}amine | 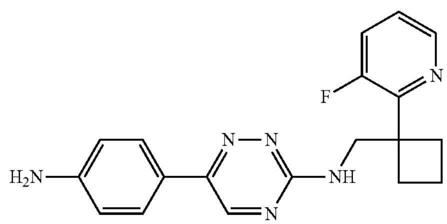 [SMILES: Nc1ccc(-c2cnc(NCC3(c4ncccc4F)CCC3)nn2)cc1] | 350.1 | B |
| {[6-(difluoromethoxy)(2-pyridyl)]cyclobutyl}[6-(5-bromo-2-fluorophenyl)(1,2,4-triazin-3-yl)]amine | 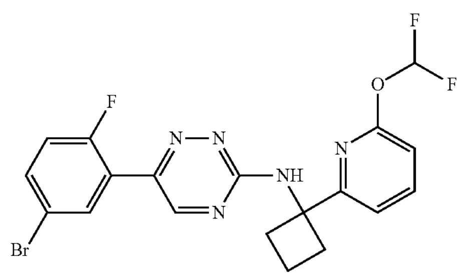 [SMILES: Fc1ccc(Br)cc1-c1cnc(NC2(c3cccc(OC(F)F)n3)CCC2)nn1] | 467.1 | B |
| 4-fluoro-3-(3-{[1-(3-fluoro(2-pyridyl))-isopropyl]amino}(1,2,4-triazin-6-yl))benzamide | 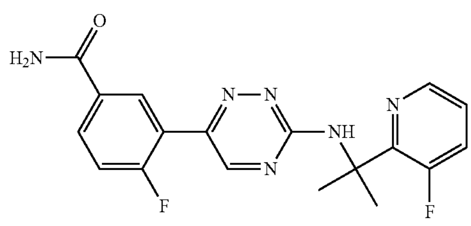 [SMILES: CC(C)(Nc1ncc(-c2cc(C(N)=O)ccc2F)nn1)c1ncccc1F] | 371.1 | B |
| 4-fluoro-3-(3-{[(3-fluoro(2-pyridyl))ethyl]amino}(1,2,4-triazin-6-yl))benzamide | 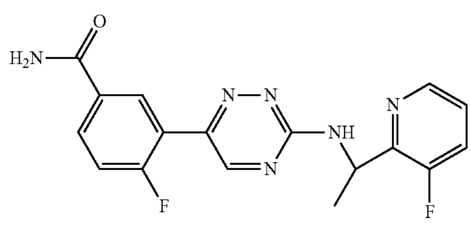 [SMILES: CC(Nc1ncc(-c2cc(C(N)=O)ccc2F)nn1)c1ncccc1F] | 357.1 | C |

TABLE 2-continued

| Compound | Structure | m/z (M + H) | Mean AC1.4 |
|---|---|---|---|
| 3-[3-({[6-(difluoromethoxy)(2-pyridyl)]methyl}amino)(1,2,4-triazin-6-yl)]-4-fluorobenzamide | 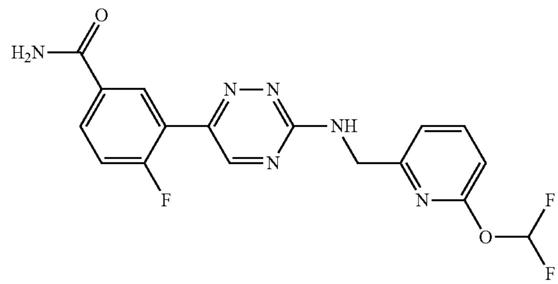 [SMILES: NC(=O)c1ccc(F)c(-c2cnc(NCc3cccc(OC(F)F)n3)nn2)c1] | 391.1 | D |
| 3-[3-({[6-(difluoromethoxy)(2-pyridyl)]ethyl}amino)(1,2,4-triazin-6-yl)]-4-fluorobenzamide | 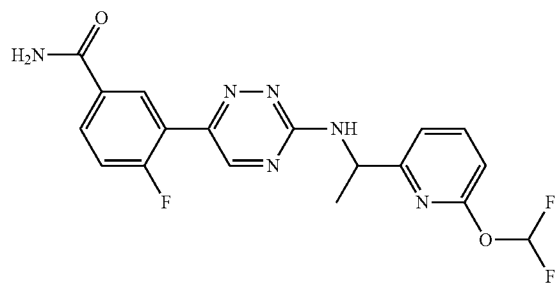 [SMILES: CC(Nc1ncc(-c2cc(C(N)=O)ccc2F)nn1)c1cccc(OC(F)F)n1] | 405.1 | C |
| 1-(3-{[1-(3-fluoro(2-pyridyl))-isopropyl]amino}-1,2,4-triazin-6-yl)pyrazole-4-carboxamide | 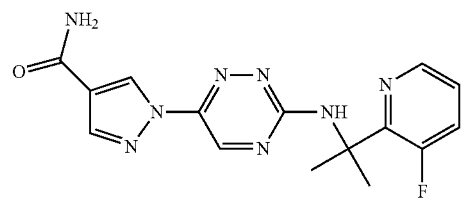 [SMILES: CC(C)(Nc1ncc(-n2cc(C(N)=O)cn2)nn1)c1ncccc1F] | 343.1 | D |
| 1-(3-{[(3-fluoro-2-pyridyl)cyclobutyl]amino}-1,2,4-triazin-6-yl)pyrazole-4-carboxamide | 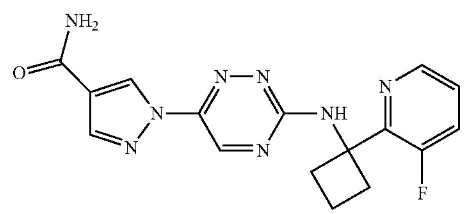 [SMILES: NC(=O)c1cnn(-c2cnc(NC3(c4ncccc4F)CCC3)nn2)c1] | 355.1 | D |
| 1-(3-{[2-(4-fluorophenyl)-2-methylpropyl]amino}-1,2,4-triazin-6-yl)pyrazole-4-carboxamide | 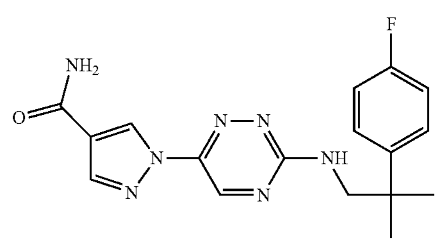 [SMILES: CC(C)(CNc1ncc(-n2cc(C(N)=O)cn2)nn1)c1ccc(F)cc1] | 356.1 | B |
| 1-[3-({[(3-fluoro-2-pyridyl)cyclobutyl]methyl}amino)-1,2,4-triazin-6-yl]pyrazole-4-carboxamide | 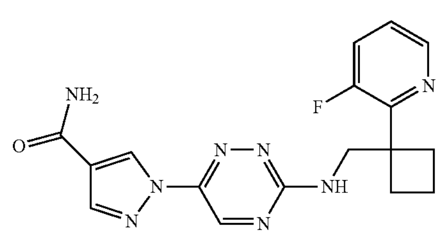 [SMILES: NC(=O)c1cnn(-c2cnc(NCC3(c4ncccc4F)CCC3)nn2)c1] | 369.1 | B |

TABLE 2-continued

| Compound | Structure | m/z (M + H) | Mean AC1.4 |
|---|---|---|---|
| 1-[3-({1-[6-(difluoromethoxy)(2-pyridyl)]-isopropyl}amino)-1,2,4-triazin-6-yl]pyrazole-4-carboxamide | 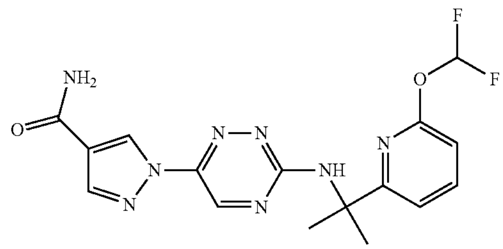 [SMILES: CC(C)(Nc1ncc(-n2cc(C(N)=O)cn2)nn1)c1cccc(OC(F)F)n1] | 391.3 | B |
| 2-[3-({1-[6-(difluoromethoxy)(2-pyridyl)]-isopropyl}amino)-1,2,4-triazin-6-yl]-1,3-thiazole-5-carboxamide | 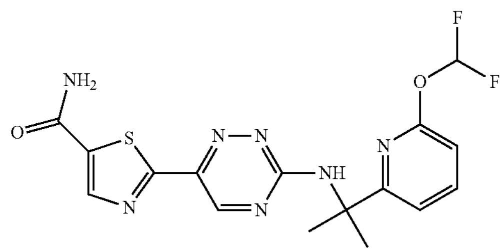 [SMILES: CC(C)(Nc1ncc(-c2ncc(C(N)=O)s2)nn1)c1cccc(OC(F)F)n1] | 408.3 | B |
| 3-(3-{[(2-pyridylcyclobutyl)methyl]amino}-1,2,4-triazin-6-yl)benzenecarbonitrile | 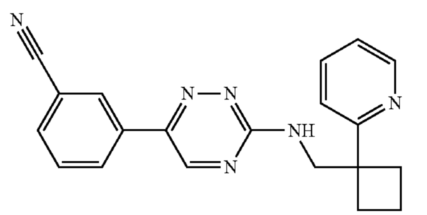 [SMILES: N#Cc1cccc(-c2cnc(NCC3(c4ccccn4)CCC3)nn2)c1] | 343.2 | B |
| 3-(3-{[(2-pyridylcyclobutyl)methyl]amino}-1,2,4-triazin-6-yl)benzamide | 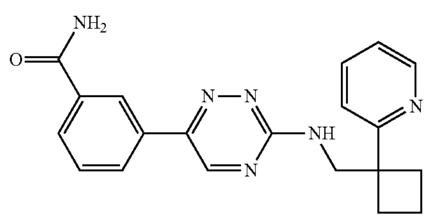 [SMILES: NC(=O)c1cccc(-c2cnc(NCC3(c4ccccn4)CCC3)nn2)c1] | 361.2 | B |
| 3-(3-{[1-(3-fluoro(2-pyridyl))-isopropyl]amino}-1,2,4-triazin-6-yl)benzamide | 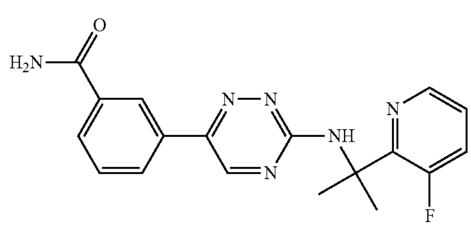 [SMILES: CC(C)(Nc1ncc(-c2cccc(C(N)=O)c2)nn1)c1ncccc1F] | 353.1 | B |
| 4-fluoro-3-(3-{[1-methyl-1-(6-methyl(2-pyridyl))ethyl]amino}(1,2,4-triazin-6-yl))benzamide | 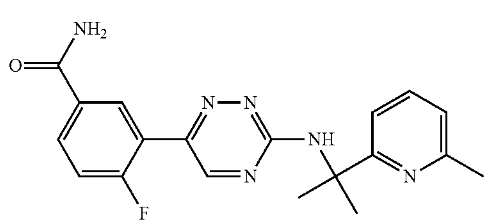 [SMILES: Cc1cccc(C(C)(C)Nc2ncc(-c3cc(C(N)=O)ccc3F)nn2)n1] | 367.1 | C |

TABLE 2-continued

| Compound | Structure | m/z (M + H) | Mean AC1.4 |
|---|---|---|---|
| 3-(3-{[1-(3-chloro(2-pyridyl))-isopropyl]amino}-1,2,4-triazin-6-yl)benzamide | 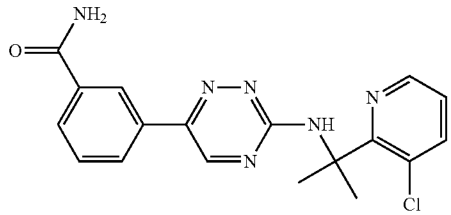 [SMILES: CC(C)(Nc1ncc(-c2cccc(C(N)=O)c2)nn1)c1ncccc1Cl] | 369.1 | B |
| 3-(3-{[1-(3-chloro(2-pyridyl))-isopropyl]amino}(1,2,4-triazin-6-yl))-4-fluorobenzamide | 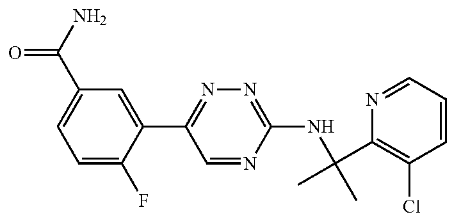 [SMILES: CC(C)(Nc1ncc(-c2cc(C(N)=O)ccc2F)nn1)c1ncccc1Cl] | 387.1 | B |
| 4-fluoro-3-(3-{[1-(5-fluoro-6-methyl(2-pyridyl))-isopropyl]amino}(1,2,4-triazin-6-yl))benzamide | 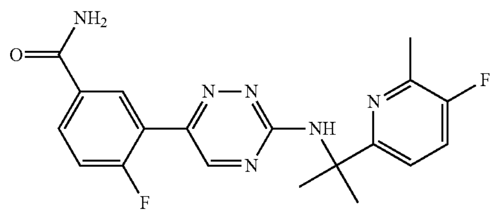 [SMILES: Cc1nc(C(C)(C)Nc2ncc(-c3cc(C(N)=O)ccc3F)nn2)ccc1F] | 385.1 | B |
| 4-fluoro-3-(3-{[1-(3-fluoro(2-pyridyl))-isopropyl]amino}(1,2,4-triazin-6-yl))benzoic acid | 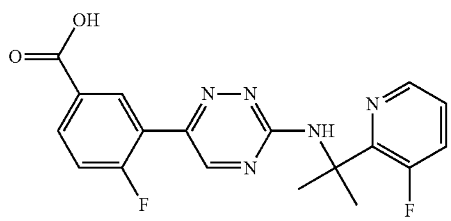 [SMILES: CC(C)(Nc1ncc(-c2cc(C(=O)O)ccc2F)nn1)c1ncccc1F] | 372.2 | C |
| [6-(3-amino-6-fluorophenyl)(1,2,4-triazin-3-yl)][1-(3-fluoro(2-pyridyl))-isopropyl]amine | 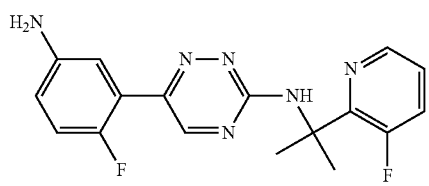 [SMILES: CC(C)(Nc1ncc(-c2cc(N)ccc2F)nn1)c1ncccc1F] | 343.2 | B |
| [4-fluoro-3-(3-{[1-(3-fluoro(2-pyridyl))-isopropyl]amino}(1,2,4-triazin-6-yl))phenyl](methylsulfonyl)amine | 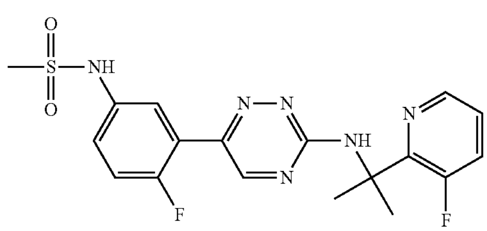 [SMILES: CC(C)(Nc1ncc(-c2cc(NS(C)(=O)=O)ccc2F)nn1)c1ncccc1F] | 421.1 | C |
| 5-(3-{[1-(3-fluoro(2-pyridyl))-isopropyl]amino}-1,2,4-triazin-6-yl)-1H-2-hydroindazol-3-one | 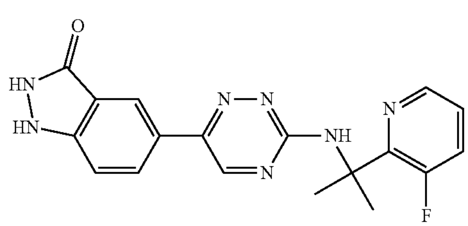 [SMILES: CC(C)(Nc1ncc(-c2ccc3[nH][nH]c(=O)c3c2)nn1)c1ncccc1F] | 366.1 | B |

TABLE 2-continued

| Compound | Structure | m/z (M + H) | Mean AC1.4 |
|---|---|---|---|
| 2-fluoro-5-(3-{[1-(3-fluoro(2-pyridyl))-isopropyl]amino}(1,2,4-triazin-6-yl))benzoic acid | 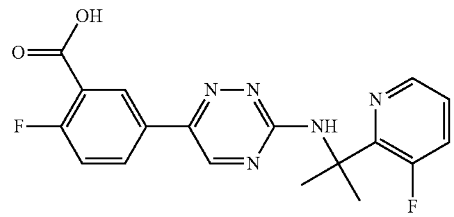 [SMILES: CC(C)(Nc1ncc(-c2ccc(F)c(C(=O)O)c2)nn1)c1ncccc1F] | 372.1 | D |
| 2-fluoro-5-(3-{[1-(3-fluoro(2-pyridyl))-isopropyl]amino}(1,2,4-triazin-6-yl))benzamide | 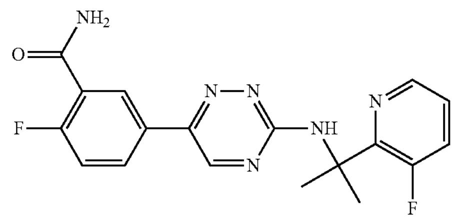 [SMILES: CC(C)(Nc1ncc(-c2ccc(F)c(C(N)=O)c2)nn1)c1ncccc1F] | 371.2 | D |
| N-((2S)-2,3-dihydroxypropyl)[4-fluoro-3-(3-{[1-(3-fluoro(2-pyridyl))-isopropyl]amino}(1,2,4-triazin-6-yl))phenyl]carboxamide | 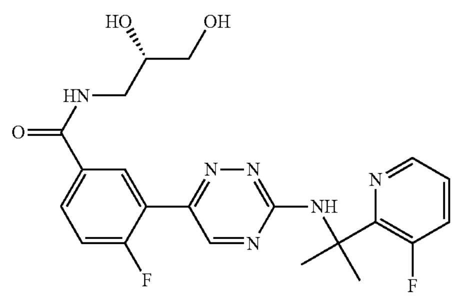 [SMILES: CC(C)(Nc1ncc(-c2cc(C(=O)NC[C@H](O)CO)ccc2F)nn1)c1ncccc1F] | 445.3 | C |
| N-[4-fluoro-3-(3-{[1-(3-fluoro(2-pyridyl))-isopropyl]amino}(1,2,4-triazin-6-yl))phenyl]methoxycarboxamide | 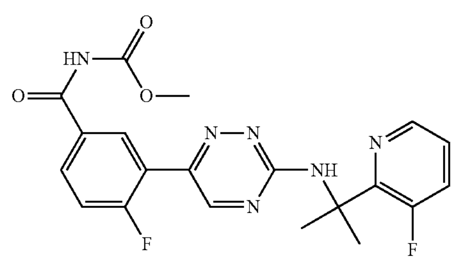 [SMILES: COC(=O)NC(=O)c1ccc(F)c(-c2cnc(NC(C)(C)c3ncccc3F)nn2)c1] | 401.1 | B |
| amino[4-fluoro-3-(3-{[1-(3-fluoro(2-pyridyl))-isopropyl]amino}(1,2,4-triazin-6-yl))phenyl]sulfonamide | 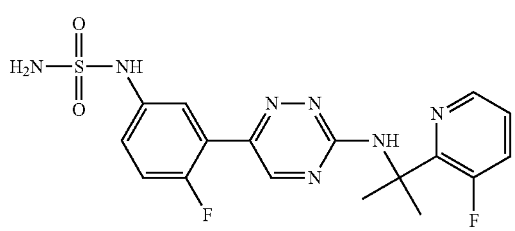 [SMILES: CC(C)(Nc1ncc(-c2cc(NS(N)(=O)=O)ccc2F)nn1)c1ncccc1F] | 422.1 | B |
| 3-[3-({1-[6-(difluoromethyl)(2-pyridyl)]-isopropyl}amino)(1,2,4-triazin-6-yl)]-4-fluorobenzamide | 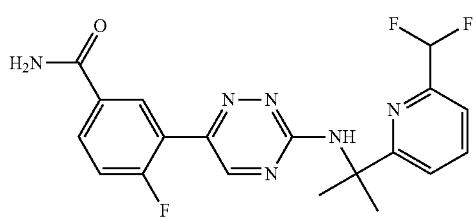 [SMILES: CC(C)(Nc1ncc(-c2cc(C(N)=O)ccc2F)nn1)c1cccc(C(F)F)n1] | 403.1 | B |

TABLE 2-continued

| Compound | Structure | m/z (M + H) | Mean AC1.4 |
|---|---|---|---|
| 3-[3-({1-[6-(difluoromethyl)(2-pyridyl)]-isopropyl}amino)(1,2,4-triazin-6-yl)]-4-fluorobenzenecarbonitrile | 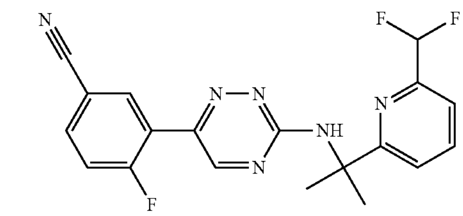 [SMILES: CC(C)(Nc1ncc(-c2cc(C#N)ccc2F)nn1)c1cccc(C(F)F)n1] | 385.1 | B |
| 2-[3-(3-{[1-(3-fluoro(2-pyridyl))-isopropyl]amino}-1,2,4-triazin-6-yl)phenyl]acetamide | 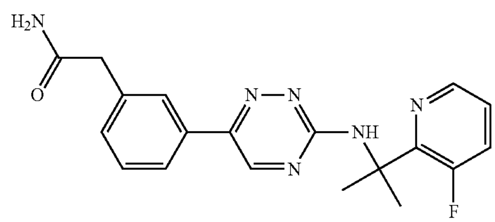 [SMILES: CC(C)(Nc1ncc(-c2cccc(CC(N)=O)c2)nn1)c1ncccc1F] | 367.1 | D |
| methyl 3-fluoro-4-(3-{[1-(3-fluoro(2-pyridyl))-isopropyl]amino}(1,2,4-triazin-6-yl))benzoate | 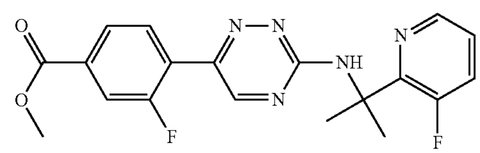 [SMILES: COC(=O)c1ccc(-c2cnc(NC(C)(C)c3ncccc3F)nn2)c(F)c1] | 386.2 | D |
| 3-fluoro-4-(3-{[1-(3-fluoro(2-pyridyl))-isopropyl]amino}(1,2,4-triazin-6-yl))benzamide | 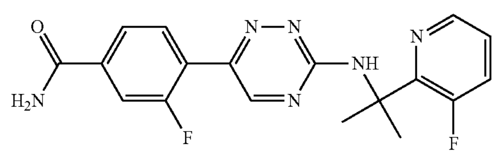 [SMILES: CC(C)(Nc1ncc(-c2ccc(C(N)=O)cc2F)nn1)c1ncccc1F] | 371.2 | D |
| 3-fluoro-4-(3-{[1-(3-fluoro(2-pyridyl))-isopropyl]amino}(1,2,4-triazin-6-yl))benzoic acid | 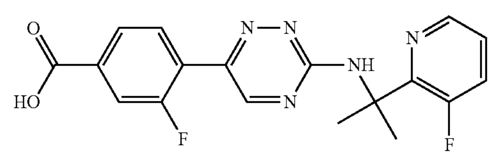 [SMILES: CC(C)(Nc1ncc(-c2ccc(C(=O)O)cc2F)nn1)c1ncccc1F] | 372.2 | D |
| [4-fluoro-3-(3-{[1-(3-fluoro(2-pyridyl))-isopropyl]amino}(1,2,4-triazin-6-yl))phenyl]methan-1-ol | 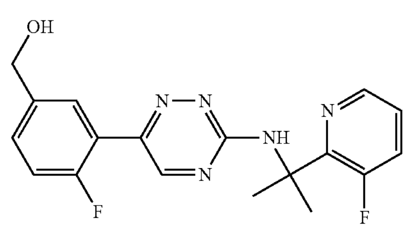 [SMILES: CC(C)(Nc1ncc(-c2cc(CO)ccc2F)nn1)c1ncccc1F] | 358.3 | C |
| {6-[5-(aminomethyl)-2-fluorophenyl](1,2,4-triazin-3-yl)}[1-(3-fluoro(2-pyridyl))-isopropyl]amine | 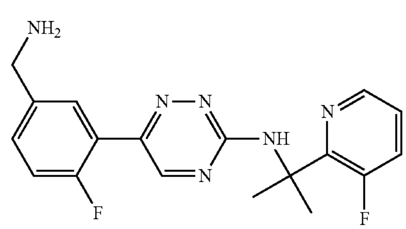 [SMILES: CC(C)(Nc1ncc(-c2cc(CN)ccc2F)nn1)c1ncccc1F] | 357.3 | D |

TABLE 2-continued

| Compound | Structure | m/z (M + H) | Mean AC1.4 |
|---|---|---|---|
| N-{[4-fluoro-3-(3-{[1-(3-fluoro(2-pyridyl))-isopropyl]amino}(1,2,4-triazin-6-yl))phenyl]methyl}acetamide | 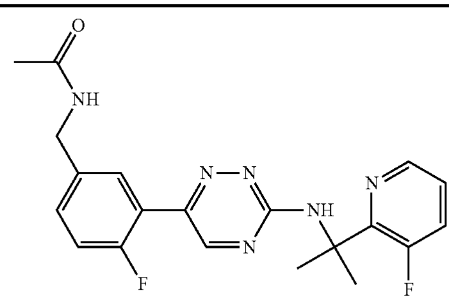 | 399.3 | D |
| 4-fluoro-3-(3-{[1-(3-fluoro-6-methyl(2-pyridyl))-isopropyl]amino}(1,2,4-triazin-6-yl))benzamide | 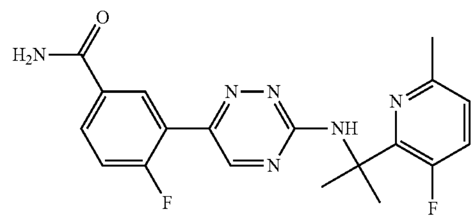 [SMILES: Cc1ccc(F)c(C(C)(C)Nc2ncc(-c3cc(C(N)=O)ccc3F)nn2)n1] | 385.1 | B |
| 2-amino-N-{[4-fluoro-3-(3-{[1-(3-fluoro(2-pyridyl))-isopropyl]amino}(1,2,4-triazin-6-yl))phenyl]methyl}acetamide | 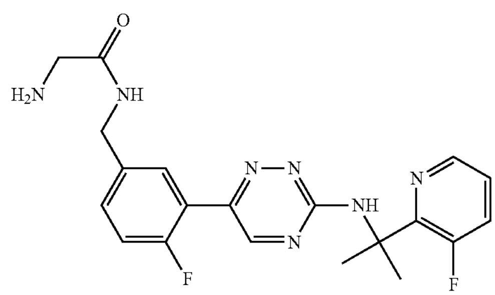 [SMILES: CC(C)(Nc1ncc(-c2cc(CNC(=O)CN)ccc2F)nn1)c1ncccc1F] | 414.2 | B |
| [1-(3-fluoro(2-pyridyl))-isopropyl](6-(1,3-thiazol-2-yl)(1,2,4-triazin-3-yl))amine | 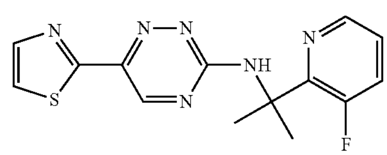 [SMILES: CC(C)(Nc1ncc(-c2nccs2)nn1)c1ncccc1F] | 317.1 | D |
| 4-fluoro-3-[3-({1-methyl-1-[3-(methylsulfonyl)phenyl]ethyl}amino)(1,2,4-triazin-6-yl)]benzamide | 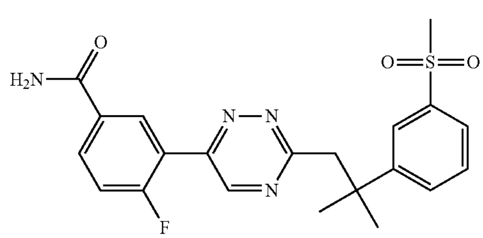 [SMILES: CC(C)(Cc1ncc(-c2cc(C(N)=O)ccc2F)nn1)c1cccc(S(C)(=O)=O)c1] | 430.2 | D |
| methyl 4-fluoro-3-[3-({1-methyl-1-[3-(methylsulfonyl)phenyl]ethyl}amino)(1,2,4-triazin-6-yl)]benzoate | 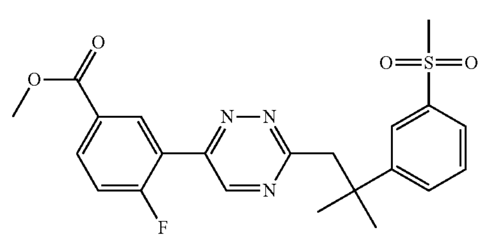 [SMILES: COC(=O)c1ccc(F)c(-c2cnc(CC(C)(C)c3cccc(S(C)(=O)=O)c3)nn2)c1] | 445.2 | D |
| [2-(3-{[1-(3-chloro(2-pyridyl))-isopropyl]amino}-1,2,4-triazin-6-yl)-1,3-thiazol-5-yl]methan-1-ol | 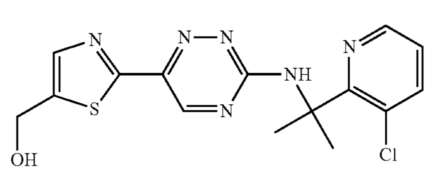 [SMILES: CC(C)(Nc1ncc(-c2ncc(CO)s2)nn1)c1ncccc1Cl] | 363.0 | D |

TABLE 2-continued

| Compound | Structure | m/z (M + H) | Mean AC1.4 |
|---|---|---|---|
| 2-[2-(3-{[1-(3-fluoro(2-pyridyl))-isopropyl]amino}-1,2,4-triazin-6-yl)-1,3-thiazol-5-yl]acetamide | 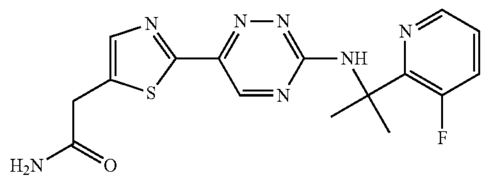 [SMILES: CC(C)(Nc1ncc(-c2ncc(CC(N)=O)s2)nn1)c1ncccc1F] | 374.3 | D |
| 3-[3-({1-[3-(difluoromethyl)(2-pyridyl)]-isopropyl}amino)(1,2,4-triazin-6-yl)]-4-fluorobenzenecarbonitrile | 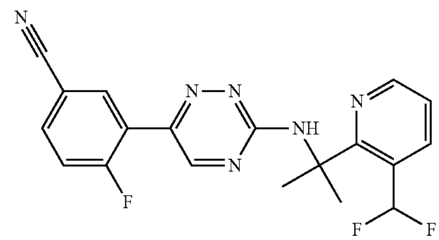 [SMILES: CC(C)(Nc1ncc(-c2cc(C#N)ccc2F)nn1)c1ncccc1C(F)F] | 385.1 | D |
| 3-[3-({1-[3-(difluoromethyl)(2-pyridyl)]-isopropyl}amino)(1,2,4-triazin-6-yl)]-4-fluorobenzamide | 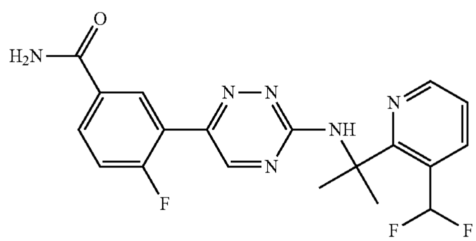 [SMILES: CC(C)(Nc1ncc(-c2cc(C(N)=O)ccc2F)nn1)c1ncccc1C(F)F] | 403.1 | C |
| {6-[5-(aminomethyl)(1,3-thiazol-2-yl)](1,2,4-triazin-3-yl)}[1-(3-chloro(2-pyridyl))-isopropyl]amine | 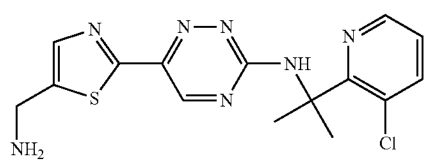 [SMILES: CC(C)(Nc1ncc(-c2ncc(CN)s2)nn1)c1ncccc1Cl] | 362.3 | D |
| N-{[2-(3-{[1-(3-chloro(2-pyridyl))-isopropyl]amino}-1,2,4-triazin-6-yl)-1,3-thiazol-5-yl]methyl}acetamide | 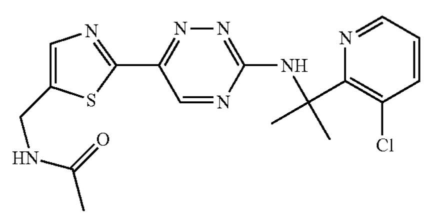 [SMILES: CC(=O)NCc1cnc(-c2cnc(NC(C)(C)c3ncccc3Cl)nn2)s1] | 404.3 | D |
| 1-(3-{[1-(3-chloro(2-pyridyl))-isopropyl]amino}-1,2,4-triazin-6-yl)pyrazole-4-carboxamide | 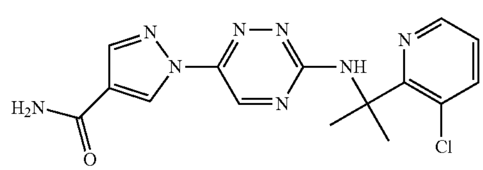 [SMILES: CC(C)(Nc1ncc(-n2cc(C(N)=O)cn2)nn1)c1ncccc1Cl] | 359.3 | D |
| {2-[3-({[3-fluoro-1-(3-fluoro(2-pyridyl))cyclobutyl]methyl}amino)-1,2,4-triazin-6-yl]-1,3-thiazol-5-yl}methan-1-ol | 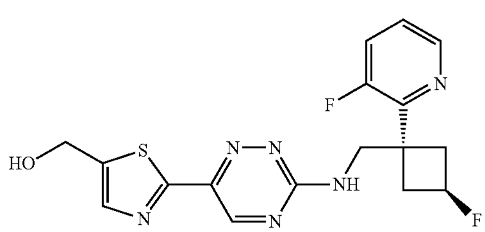 [SMILES: OCc1cnc(-c2cnc(NC[C@]3(c4ncccc4F)C[C@H](F)C3)nn2)s1] | 391.3 | B |

TABLE 2-continued

| Compound | Structure | m/z (M + H) | Mean AC1.4 |
|---|---|---|---|
| 3-[3-({[3-fluoro-1-(3-fluoro(2-pyridyl))cyclobutyl]methyl}amino)-1,2,4-triazin-6-yl]benzamide | 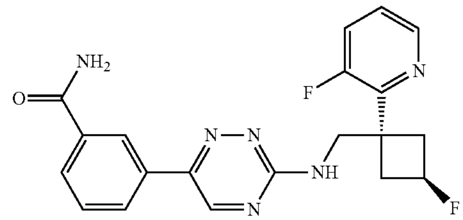 | 397.2 | A |
| {6-[5-(aminomethyl)(1,3-thiazol-2-yl)](1,2,4-triazin-3-yl)}{[3-fluoro-1-(3-fluoro(2-pyridyl))cyclobutyl]methyl}amine | 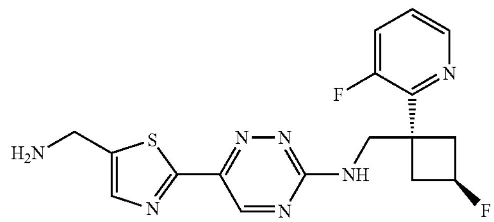 [SMILES: NCc1cnc(-c2cnc(NC[C@]3(c4ncccc4F)C[C@H](F)C3)nn2)s1] | 390.3 | B |
| N-({2-[3-({[3-fluoro-1-(3-fluoro(2-pyridyl))cyclobutyl]methyl}amino)-1,2,4-triazin-6-yl]-1,3-thiazol-5-yl}methyl)acetamide | 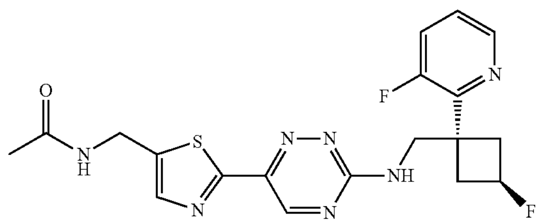 [SMILES: CC(=O)NCc1cnc(-c2cnc(NC[C@]3(c4ncccc4F)C[C@H](F)C3)nn2)s1] | 432.1 | B |
| methyl 3-(3-{[2-(3-chloro(2-pyridyl))-2-methylpropyl]amino}(1,2,4-triazin-6-yl))-4-fluorobenzoate | 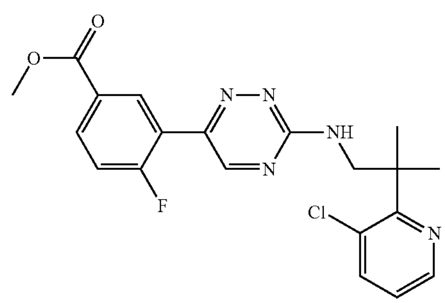 [SMILES: COC(=O)c1ccc(F)c(-c2cnc(NCC(C)(C)c3ncccc3Cl)nn2)c1] | 416.2 | D |
| methyl 3-[3-({[(3-chloro(2-pyridyl))cyclobutyl]methyl}amino)(1,2,4-triazin-6-yl)]-4-fluorobenzoate | 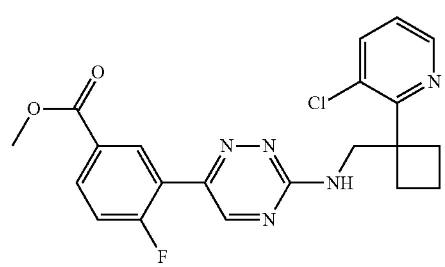 [SMILES: COC(=O)c1ccc(F)c(-c2cnc(NCC3(c4ncccc4Cl)CCC3)nn2)c1] | 428.2 | B |
| methyl 4-fluoro-3-(3-{[(2-pyridylcyclobutyl)methyl]amino}(1,2,4-triazin-6-yl))benzoate | 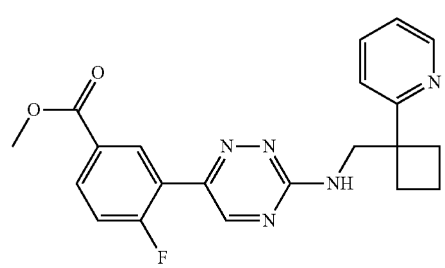 [SMILES: COC(=O)c1ccc(F)c(-c2cnc(NCC3(c4ccccn4)CCC3)nn2)c1] | 394.3 | C |

TABLE 2-continued

| Compound | Structure | m/z (M + H) | Mean AC1.4 |
|---|---|---|---|
| 3-[3-({[(3-chloro(2-pyridyl))cyclobutyl]methyl}amino)(1,2,4-triazin-6-yl)]-4-fluorobenzamide | 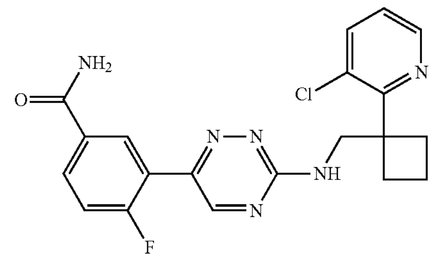 | 413.2 | A |
| 3-(3-{[2-(3-chloro(2-pyridyl))-2-methylpropyl]amino}(1,2,4-triazin-6-yl))-4-fluorobenzamide | 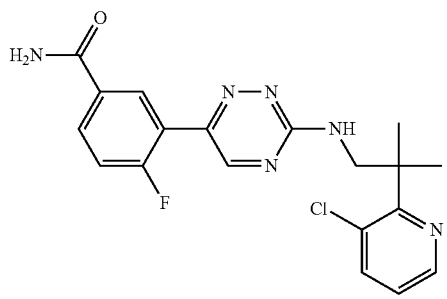 [SMILES: CC(C)(CNc1ncc(-c2cc(C(N)=O)ccc2F)nn1)c1ncccc1Cl] | 401.2 | B |
| 4-fluoro-3-(3-{[(2-pyridylcyclobutyl)methyl]amino}(1,2,4-triazin-6-yl))benzamide | 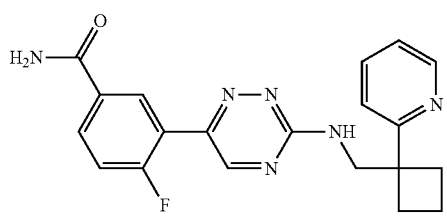 [SMILES: NC(=O)c1ccc(F)c(-c2cnc(NCC3(c4ccccn4)CCC3)nn2)c1] | 379.3 | B |
| 3-[3-({[(3-chloro(2-pyridyl))cyclobutyl]methyl}amino)(1,2,4-triazin-6-yl)]-4-fluorobenzoic acid | 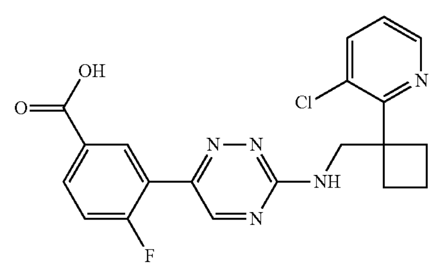 [SMILES: O=C(O)c1ccc(F)c(-c2cnc(NCC3(c4ncccc4Cl)CCC3)nn2)c1] | 414.2 | A |
| 3-(3-{[2-(3-chloro(2-pyridyl))-2-methylpropyl]amino}(1,2,4-triazin-6-yl))-4-fluorobenzoic acid | 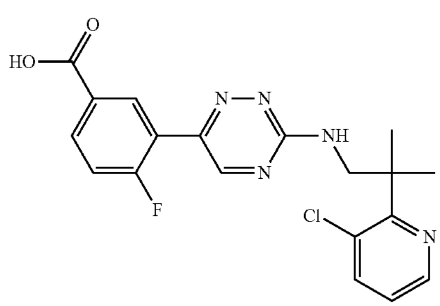 [SMILES: CC(C)(CNc1ncc(-c2cc(C(=O)O)ccc2F)nn1)c1ncccc1Cl] | 402.2 | B |

TABLE 2-continued

| Compound | Structure | m/z (M + H) | Mean AC1.4 |
|---|---|---|---|
| 4-fluoro-3-[3-({[3-fluoro-1-(3-fluoro(2-pyridyl))cyclobutyl]methyl}amino)(1,2,4-triazin-6-yl)]benzamide | 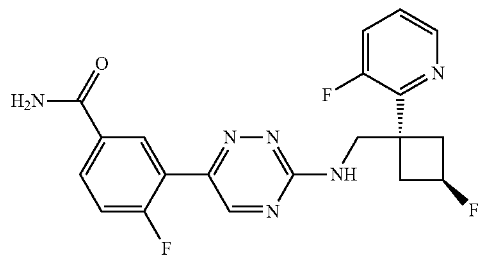 [SMILES: NC(=O)c1ccc(F)c(-c2cnc(NC[C@]3(c4ncccc4F)C[C@H](F)C3)nn2)c1] | 415.1 | A |
| 3-[3-({[1-(3-chloro(2-pyridyl))-3-fluorocyclobutyl]methyl}amino)-1,2,4-triazin-6-yl]benzamide | 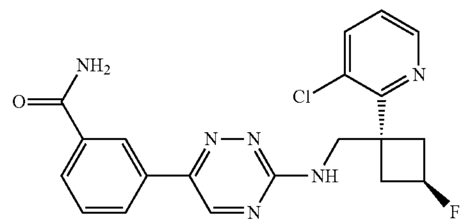 [SMILES: NC(=O)c1cccc(-c2cnc(NC[C@]3(c4ncccc4Cl)C[C@H](F)C3)nn2)c1] | 413.2 | A |
| 3-[3-({[1-(3-chloro(2-pyridyl))-3-fluorocyclobutyl]methyl}amino)(1,2,4-triazin-6-yl)]-4-fluorobenzamide | 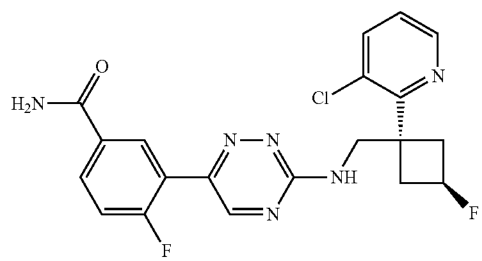 [SMILES: NC(=O)c1ccc(F)c(-c2cnc(NC[C@]3(c4ncccc4Cl)C[C@H](F)C3)nn2)c1] | 431.2 | A |
| 3-[3-({[1-(3-chloro(2-pyridyl))-3-fluorocyclobutyl]methyl}amino)-1,2,4-triazin-6-yl]benzenecarbonitrile | 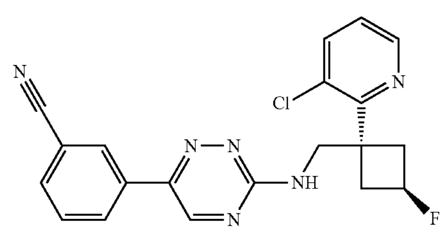 [SMILES: N#Cc1cccc(-c2cnc(NC[C@]3(c4ncccc4Cl)C[C@H](F)C3)nn2)c1] | 395.2 | B |
| 3-[3-({[(3-fluoro-2-pyridyl)cyclobutyl]methyl}amino)-1,2,4-triazin-6-yl]benzamide | 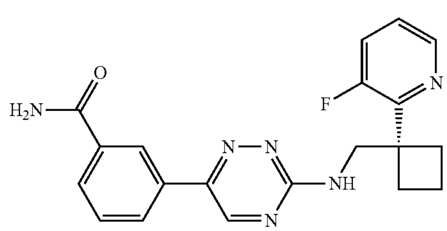 | 379.3 | B |
| 2-{2-[3-({[3-fluoro-1-(3-fluoro(2-pyridyl))cyclobutyl]methyl}amino)-1,2,4-triazin-6-yl]-1,3-thiazol-5-yl}acetamide | 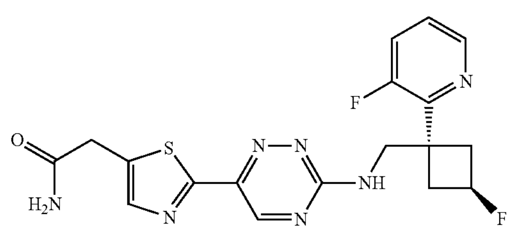 [SMILES: NC(=O)Cc1cnc(-c2cnc(NC[C@]3(c4ncccc4F)C[C@H](F)C3)nn2)s1] | 418.2 | C |

TABLE 2-continued

| Compound | Structure | m/z (M + H) | Mean AC1.4 |
|---|---|---|---|
| 2-{2-[3-({[(3-fluoro-2-pyridyl)cyclobutyl]methyl}amino)-1,2,4-triazin-6-yl]-1,3-thiazol-5-yl}acetamide | 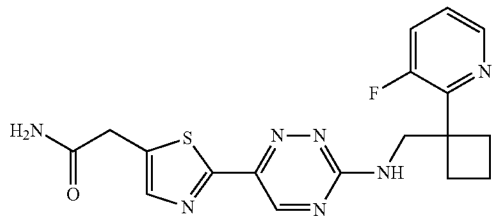 [SMILES: NC(=O)Cc1cnc(-c2cnc(NCC3(c4ncccc4F)CCC3)nn2)s1] | 400.3 | C |
| {2-[3-({[(3-fluoro-2-pyridyl)cyclobutyl]methyl}amino)-1,2,4-triazin-6-yl]-1,3-thiazol-5-yl}methan-1-ol | 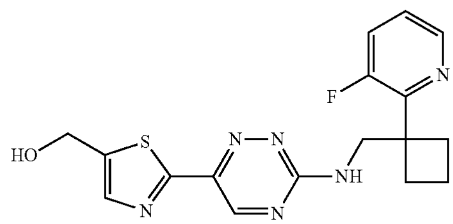 [SMILES: OCc1cnc(-c2cnc(NCC3(c4ncccc4F)CCC3)nn2)s1] | 373.3 | C |
| 4-fluoro-3-[3-({[(3-fluoro(2-pyridyl))cyclobutyl]methyl}amino)(1,2,4-triazin-6-yl)]benzoic acid | 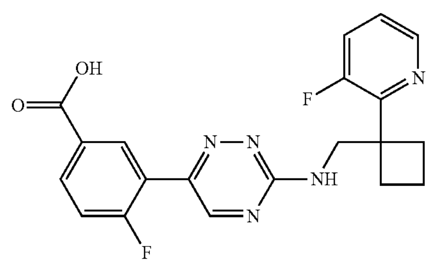 [SMILES: O=C(O)c1ccc(F)c(-c2cnc(NCC3(c4ncccc4F)CCC3)nn2)c1] | 398.1 | B |
| {4-fluoro-3-[3-({[(3-fluoro(2-pyridyl))cyclobutyl]methyl}amino)(1,2,4-triazin-6-yl)]phenyl}-N-methylcarboxamide | 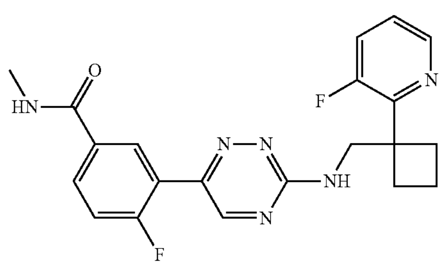 [SMILES: CNC(=O)c1ccc(F)c(-c2cnc(NCC3(c4ncccc4F)CCC3)nn2)c1] | 411.1 | B |
| 4-fluoro-3-[3-({[(3-fluoro(2-pyridyl))cyclobutyl]methyl}amino)(1,2,4-triazin-6-yl)]benzamide | 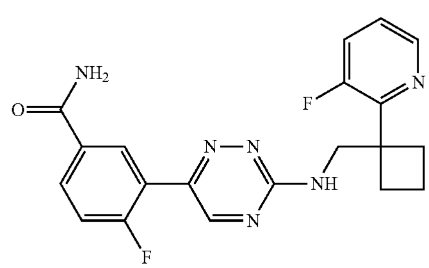 [SMILES: NC(=O)c1ccc(F)c(-c2cnc(NCC3(c4ncccc4F)CCC3)nn2)c1] | 397.1 | A |
| {3-[3-({[1-(3-chloro(2-pyridyl))-3-fluorocyclobutyl]methyl}amino)(1,2,4-triazin-6-yl)]phenyl}-N-methylcarboxamide | 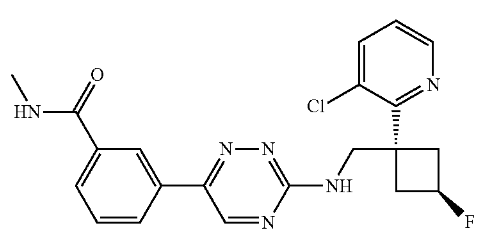 [SMILES: CNC(=O)c1cccc(-c2cnc(NC[C@]3(c4ncccc4Cl)C[C@H](F)C3)nn2)c1] | 427.3 | B |

TABLE 2-continued

| Compound | Structure | m/z (M + H) | Mean AC1.4 |
|---|---|---|---|
| {3-[3-({[1-(3-chloro(2-pyridyl))-3-fluorocyclobutyl]methyl}amino)(1,2,4-triazin-6-yl)]-4-fluorophenyl}-N-methylcarboxamide | 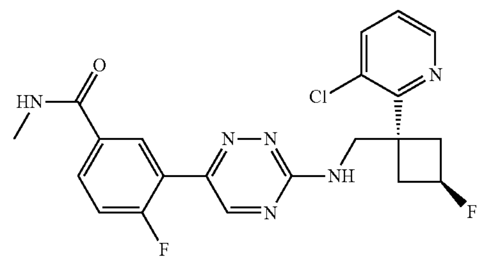 [SMILES: CNC(=O)c1ccc(F)c(-c2cnc(NC[C@]3(c4ncccc4Cl)C[C@H](F)C3)nn2)c1] | 445.2 | A |
| 3-[3-({[1-(3-chloro(2-pyridyl))-3,3-difluorocyclobutyl]methyl}amino)(1,2,4-triazin-6-yl)]-4-fluorobenzamide | 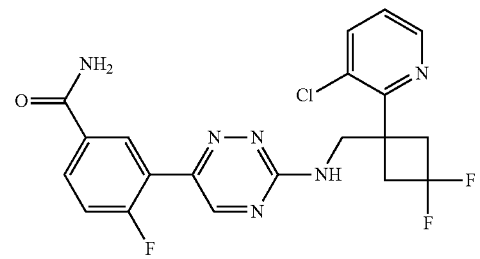 [SMILES: NC(=O)c1ccc(F)c(-c2cnc(NCC3(c4ncccc4Cl)CC(F)(F)C3)nn2)c1] | 449.2 | A |
| {3-[3-({[1-(3-chloro(2-pyridyl))-3,3-difluorocyclobutyl]methyl}amino)(1,2,4-triazin-6-yl)]-4-fluorophenyl}-N-methylcarboxamide | 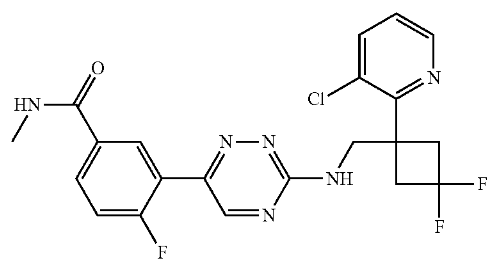 [SMILES: CNC(=O)c1ccc(F)c(-c2cnc(NCC3(c4ncccc4Cl)CC(F)(F)C3)nn2)c1] | 463.2 | B |
| {4-fluoro-3-[3-({[3-fluoro-1-(3-fluoro(2-pyridyl))cyclobutyl]methyl}amino)(1,2,4-triazin-6-yl)]phenyl}-N-methylcarboxamide | 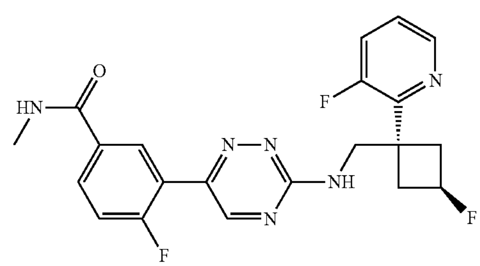 | 429.3 | B |
| {3-[3-({[3-fluoro-1-(3-fluoro(2-pyridyl))cyclobutyl]methyl}amino)(1,2,4-triazin-6-yl)]-4-hydroxyphenyl}-N-methylcarboxamide | 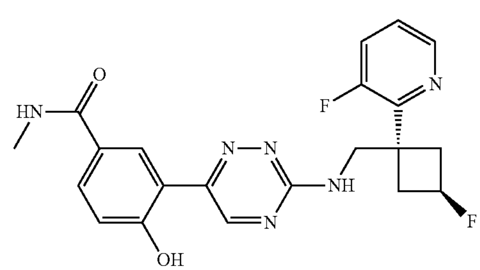 [SMILES: CNC(=O)c1ccc(O)c(-c2cnc(NC[C@]3(c4ncccc4F)C[C@H](F)C3)nn2)c1] | 427.2 | A |
| 3-[3-({[3-fluoro-1-(3-fluoro(2-pyridyl))cyclobutyl]methyl}amino)(1,2,4-triazin-6-yl)]-4-hydroxybenzamide | 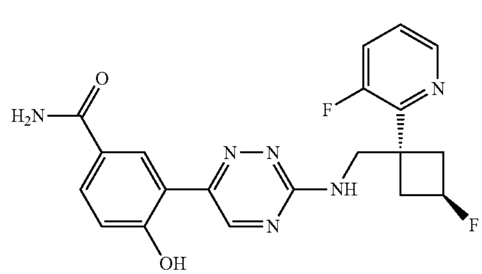 [SMILES: NC(=O)c1ccc(O)c(-c2cnc(NC[C@]3(c4ncccc4F)C[C@H](F)C3)nn2)c1] | 413.2 | A |

TABLE 2-continued

| Compound | Structure | m/z (M + H) | Mean AC1.4 |
|---|---|---|---|
| {3-[3-({[3-fluoro-1-(3-fluoro(2-pyridyl))cyclobutyl]methyl}amino)(1,2,4-triazin-6-yl)]phenyl}-N-methylcarboxamide | 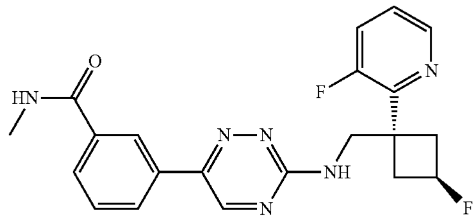 [SMILES: CNC(=O)c1cccc(-c2cnc(NC[C@]3(c4ncccc4F)C[C@H](F)C3)nn2)c1] | 411.3 | B |
| 4-fluoro-3-[3-({[3-fluoro-1-(3-fluoro(2-pyridyl))cyclobutyl]methyl}amino)(1,2,4-triazin-6-yl)]-2-hydroxybenzamide | 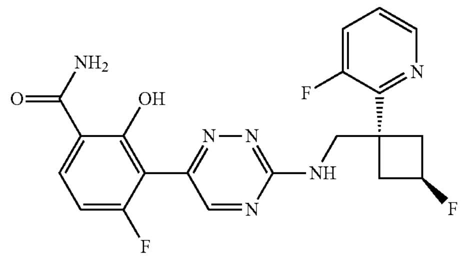 [SMILES: NC(=O)c1ccc(F)c(-c2cnc(NC[C@]3(c4ncccc4F)C[C@H](F)C3)nn2)c1O] | 430.1 | A |

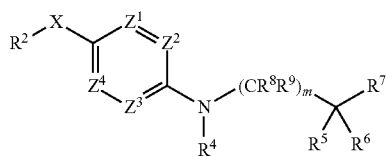

While the present invention has been described with reference to the specific embodiments described herein, it should be understood by those skilled in the art that various changes may be made and equivalents may be substituted without departing from the true spirit and scope of the invention. In addition, modifications may be made to adapt a particular situation, material, composition of matter and/or process to the objective, spirit and scope of the present invention. All such modifications are intended to be within the scope of the claims appended hereto.

What is claimed is:

1. A compound of Formula I:

Formula I or a pharmaceutically acceptable salt thereof, wherein:
$Z^1$, $Z^2$ and $Z^3$ are each N and $Z^4$ is $CR^1$; or $Z^1$, $Z^2$ and $Z^4$ are each N and $Z^3$ is $CR^1$;

$R^1$, at each occurrence, is independently selected from hydrogen, halogen, CN, $C_{1-6}$ alkyl, $C_{1-6}$ haloalkyl, $C(O)OR^a$, $C(O)NR^bR^c$, $OR^a$, $NR^bR^c$, $C_{6-10}$ aryl and 5-10 membered heteroaryl;

$R^2$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl, 5-10 membered heteroaryl and $NR^bR^c$, wherein each of the $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl groups is optionally substituted with 1, 2, 3, 4 or 5 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_nC_{6-10}$ aryl and $(CH_2)_n$5-10 membered heteroaryl groups is optionally substituted with 1, 2, 3, 4 or 5 $R^f$ substituents;

$R^4$ is selected from hydrogen, $C_{1-6}$ alkyl, $C_{1-6}$ haloalkyl, $C(O)R^a$, $C(O)OR^a$, $C(O)NR^bR^c$ and $SO_2R^a$;

$R^5$ and $R^6$ are each independently $C_{1-6}$ alkyl;

or alternatively, $R^5$ and $R^6$ together with the carbon atom to which they are bound form a group selected from $C_{3-8}$ cycloalkyl, $C_{3-8}$ cycloalkenyl, 3-8 membered heterocycloalkyl and 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl;

$R^7$ is selected from $C_{3-8}$ cycloalkyl, $C_{3-8}$ cycloalkenyl, 3-8 membered heterocycloalkyl, 3-8 membered heterocycloalkenyl, $C_{6-10}$ aryl and 5-10 membered heteroaryl, each optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^8$ and $R^9$, at each occurrence, are each independently selected from hydrogen, halogen and $C_{1-6}$ alkyl;

X is a bond;

$R^a$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^b$ and $R^b$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, $C(O)OR^g$, $C(O)NR^iR^j$ and $SO_2R^g$, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents;

$R^d$, at each occurrence, is independently selected from hydrogen and $C_{1-6}$ alkyl;

$R^e$, at each occurrence, is independently selected from hydrogen, CN, OH, $C_{1-6}$ alkoxy, $C_{1-6}$ alkyl and $C_{1-6}$ haloalkyl;

$R^f$, at each occurrence, is independently selected from halogen, CN, $OR^h$, $OC(O)R^h$, $OC(O)OR^h$, $OC(O)NR^iR^j$, $NR^dC(O)R^h$, $NR^dC(O)OR^h$, $NR^dC(O)NR^iR^j$, $NR^dC(O)C(O)NR^iR^j$, $NR^dC(S)R^h$, $NR^dC(S)OR^h$, $NR^dC(S)NR^iR^j$, $NR^dC(NR^e)NR^iR^j$, $NR^dS(O)R^h$, $NR^dSO_2R^h$, $NR^dSO_2NR^iR^j$, $C(O)R^h$, $C(O)OR^h$, $C(O)NR^iR^j$, $C(S)R^h$, $C(S)OR^h$, $C(S)NR^iR^j$, $C(NR^e)NR^iR^j$, $SR^h$, $S(O)R^h$, $SO_2R^h$, $SO_2NR^iR^j$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

or two $R^f$ substituents bound to a single carbon atom, together with the carbon atom to which they are both bound, form a group selected from carbonyl, $C_{3-8}$ cycloalkyl and 3-8 membered heterocycloalkyl;

$R^g$, at each occurrence, is independently selected from $C_{1-6}$ alkyl, $C_{1-6}$ haloalkyl, phenyl, naphthyl, and $C_{7-11}$ aralkyl, each optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^h$, at each occurrence, is independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^k$ substituents;

$R^i$ and $R^j$, at each occurrence, are each independently selected from hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, 5-10 membered heteroaryl, $C(O)R^g$, and $C(O)OR^g$, wherein each of the $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 substituents selected from halogen, CN, OH, $C_{1-6}$ alkoxy, $C_{1-6}$ alkyl and $C_{1-6}$ haloalkyl;

$R^k$, at each occurrence, is independently selected from halogen, CN, oxo, OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, $NHC(O)OC_{7-11}$ aralkyl, $C(O)C_{1-6}$ alkyl, $C(O)C_{7-11}$ aralkyl, $C(O)OC_{1-6}$ alkyl, $C(O)OC_{7-11}$ aralkyl, $C_{1-6}$ alkyl, $C_{1-6}$ haloalkyl, $C_{2-6}$ alkenyl, and $C_{2-6}$ alkynyl, wherein each $C_{1-6}$ alkyl, $C_{2-6}$ alkenyl, $C_{2-6}$ alkynyl, and $C_{7-11}$ aralkyl substituent is optionally substituted with 1, 2 or 3 substituents selected from OH, $C_{1-6}$ alkoxy, $NH_2$, $NH(C_{1-6}$ alkyl), $N(C_{1-6}$ alkyl)$_2$, $NHC(O)C_{1-6}$ alkyl, $NHC(O)C_{7-11}$ aralkyl, $NHC(O)OC_{1-6}$ alkyl, and $NHC(O)OC_{7-11}$ aralkyl;

m is 0, 1 or 2;

n, at each occurrence, independently is 0, 1 or 2;

p is 0, 1 or 2; and q is 0, 1 or 2.

2. The compound of claim 1, or a pharmaceutically acceptable salt thereof, wherein m is 0.

3. The compound of claim 1, or a pharmaceutically acceptable salt thereof, wherein m is 1.

4. The compound of claim 3, or a pharmaceutically acceptable salt thereof, wherein $R^8$ and $R^9$ are each hydrogen.

5. The compound of claim 1, or a pharmaceutically acceptable salt thereof, wherein $R^5$ and $R^6$ are each $C_{1-6}$ alkyl.

6. The compound of claim 5, or a pharmaceutically acceptable salt thereof, wherein $R^5$ and $R^6$ are each methyl.

7. The compound of claim 1, or a pharmaceutically acceptable salt thereof, wherein $R^5$ and $R^6$ together with the carbon atom to which they are bound form a group selected from $C_{3-8}$ cycloalkyl, $C_{3-8}$ cycloalkenyl, 3-8 membered heterocycloalkyl and 3-8 membered heterocycloalkenyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

8. The compound of claim 7, or a pharmaceutically acceptable salt thereof, wherein $R^5$ and $R^6$ together with the carbon atom to which they are bound form $C_{3-8}$ cycloalkyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

9. The compound of claim 8, or a pharmaceutically acceptable salt thereof, wherein $R^5$ and $R^6$ together with the carbon atom to which they are bound form a group selected from cyclopropyl, cyclobutyl, cyclopentyl and cyclohexyl, each optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

10. The compound of claim 9, or a pharmaceutically acceptable salt thereof, wherein $R^5$ and $R^6$ together with the carbon atom to which they are bound form cyclobutyl optionally substituted with 1, 2, 3, 4 or 5 substituents selected from halogen, CN, oxo, $OR^a$, $OC(O)R^a$, $OC(O)OR^a$, $NR^bR^c$, $C(O)R^a$, $C(O)OR^a$, $C(O)NR^bR^c$, $S(O)R^a$, $SO_2R^a$, $SO_2NR^bR^c$, $C_{1-6}$ alkyl and $C_{1-6}$ haloalkyl.

11. The compound of claim 10, or a pharmaceutically acceptable salt thereof, wherein $R^5$ and $R^6$ together with the carbon atom to which they are bound form cyclobutyl optionally substituted with one or two halogens.

12. The compound of claim 11, or a pharmaceutically acceptable salt thereof, wherein $R^5$ and $R^6$ together with the carbon atom to which they are bound form a group selected from cyclobutyl, 3-fluorocyclobutyl and 3,3-difluorocyclobutyl.

13. The compound of claim 1, or a pharmaceutically acceptable salt thereof, wherein $Z^1$, $Z^2$ and $Z^3$ are each N and $Z^4$ is $CR^1$.

14. The compound of claim 1, or a pharmaceutically acceptable salt thereof, wherein $Z^1$, $Z^2$ and $Z^4$ are each N and $Z^3$ is $CR^1$.

15. The compound of claim 1, wherein the compound is of Formula II(e) or II(f), or a pharmaceutically acceptable salt thereof:

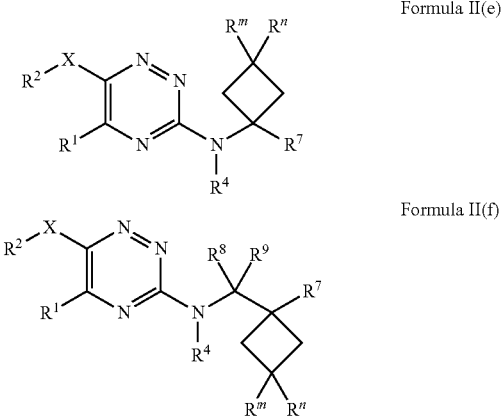

Formula II(e)

Formula II(f)

wherein $R^m$ and $R^n$ are each independently selected from hydrogen, halogen and $C_{1-6}$ alkyl.

16. The compound of claim 1, wherein the compound is of Formula III(e) or III(f), or a pharmaceutically acceptable salt thereof:

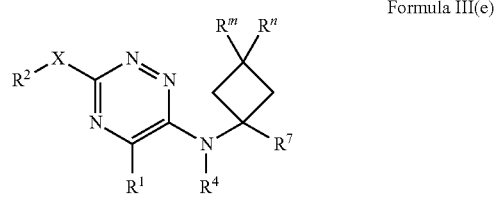

Formula III(e)

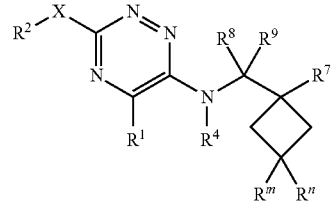

Formula III(f)

wherein $R^m$ and $R^n$ are each independently selected from hydrogen, halogen and $C_{1-6}$ alkyl.

17. The compound of claim 15, or a pharmaceutically acceptable salt thereof, wherein one of $R^m$ and $R^n$ is hydrogen and the other is halogen.

18. The compound of claim 17, or a pharmaceutically acceptable salt thereof, wherein the halogen and $R^7$ are in a trans configuration with respect to one another on the cyclobutyl ring.

19. The compound of claim 17, or a pharmaceutically acceptable salt thereof, wherein the halogen and $R^7$ are in a cis configuration with respect to one another on the cyclobutyl ring.

20. The compound of claim 18, or a pharmaceutically acceptable salt thereof, wherein one of $R^m$ and $R^n$ is hydrogen and the other is fluorine.

21. The compound of claim 1, or a pharmaceutically acceptable salt thereof, wherein $R^7$ is phenyl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

22. The compound of claim 1, or a pharmaceutically acceptable salt thereof, wherein $R^7$ is 5-10 membered heteroaryl optionally substituted with 1, 2, 3, 4 or 5 substituents selected from halogen, CN, oxo, $OR^a$, $OC(O)R^a$, $OC(O)OR^a$, $OC(O)NR^bR^c$, $NR^bR^c$, $NR^dC(O)R^a$, $NR^dC(O)OR^a$, $NR^dC(O)NR^bR^c$, $NR^dC(O)C(O)NR^bR^c$, $NR^dC(S)R^a$, $NR^dC(S)OR^a$, $NR^dC(S)NR^bR^c$, $NR^dC(NR^e)NR^bR^c$, $NR^dS(O)R^a$, $NR^dSO_2R^a$, $NR^dSO_2NR^bR^c$, $C(O)R^a$, $C(O)OR^a$, $C(O)NR^bR^c$, $C(S)R^a$, $C(S)OR^a$, $C(S)NR^bR^c$, $C(NR^e)NR^bR^c$, $SR^a$, $S(O)R^a$, $SO_2R^a$, $SO_2NR^bR^c$, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl, and 5-10 membered heteroaryl, wherein each of the $C_{1-6}$ alkyl, $C_{2-6}$ alkenyl, $C_{2-6}$ alkynyl, $C_{3-8}$ cycloalkyl, $C_{3-8}$ cycloalkenyl, 3-8 membered heterocycloalkyl, 3-8 membered heterocycloalkenyl, $C_{6-10}$ aryl, $C_{7-11}$ aralkyl and 5-10 membered heteroaryl groups is optionally substituted with 1, 2, 3, 4 or 5 $R^f$ substituents.

23. The compound of claim 22, or a pharmaceutically acceptable salt thereof, wherein $R^7$ is pyridyl optionally substituted with 1, 2, 3, 4 or 5 substituents selected from halogen, CN, oxo, $OR^a$, $OC(O)R^a$, $OC(O)OR^a$, $OC(O)NR^bR^c$, NR$^b$R$^c$, NR$^d$C(O)R$^a$, NR$^d$C(O)OR$^a$, NR$^d$C(O)NR$^b$R$^c$, NR$^d$C(O)C(O)NR$^b$R$^c$, NR$^d$C(S)R$^a$, NR$^d$C(S)OR$^a$, NR$^d$C(S)NR$^b$R$^c$, NR$^d$C(NR$^e$)NR$^b$R$^c$, NR$^d$S(O)R$^a$, NR$^d$SO$_2$R$^a$, NR$^d$SO$_2$NR$^b$R$^c$, C(O)R$^a$, C(O)OR$^a$, C(O)NR$^b$R$^c$, C(S)R$^a$, C(S)OR$^a$, C(S)NR$^b$R$^c$, C(NR$^e$)NR$^b$R$^c$, SR$^a$, S(O)R$^a$, SO$_2$R$^a$, SO$_2$NR$^b$R$^c$, C$_{1-6}$ alkyl, C$_{1-6}$ haloalkyl, C$_{2-6}$ alkenyl, C$_{2-6}$ alkynyl, C$_{3-6}$ cycloalkyl, C$_{3-6}$ cycloalkenyl, 3-6 membered heterocycloalkyl, 3-6 membered heterocycloalkenyl, phenyl, naphthyl, C$_{7-11}$ aralkyl, and 5-10 membered heteroaryl, wherein each of the C$_{1-6}$ alkyl, C$_{2-6}$ alkenyl, C$_{2-6}$ alkynyl, C$_{3-8}$ cycloalkyl, C$_{3-8}$ cycloalkenyl, 3-8 membered heterocycloalkyl, 3-8 membered heterocycloalkenyl, C$_{6-10}$ aryl, C$_{7-11}$ aralkyl and 5-10 membered heteroaryl groups is optionally substituted with 1, 2, 3, 4 or 5 R$^f$ substituents.

24. The compound of claim 23, or a pharmaceutically acceptable salt thereof, wherein R$^7$ is 2-pyridyl optionally substituted with 1, 2, 3, 4 or 5 substituents selected from halogen, CN, oxo, OR$^a$, OC(O)R$^a$, OC(O)OR$^a$, OC(O)NR$^b$R$^c$, NR$^b$R$^c$, NR$^d$C(O)R$^a$, NR$^d$C(O)OR$^a$, NR$^d$C(O)NR$^b$R$^c$, NR$^d$C(O)C(O)NR$^b$R$^c$, NR$^d$C(S)R$^a$, NR$^d$C(S)OR$^a$, NR$^d$C(S)NR$^b$R$^c$, NR$^d$C(NR$^e$)NR$^b$R$^c$, NR$^d$S(O)R$^a$, NR$^d$SO$_2$R$^a$, NR$^d$SO$_2$NR$^b$R$^c$, C(O)R$^a$, C(O)OR$^a$, C(O)NR$^b$R$^c$, C(S)R$^a$, C(S)OR$^a$, C(S)NR$^b$R$^c$, C(NR$^e$)NR$^b$R$^c$, SR$^a$, S(O)R$^a$, SO$_2$R$^a$, SO$_2$NR$^b$R$^c$, C$_{1-6}$ alkyl, C$_{1-6}$ haloalkyl, C$_{2-6}$ alkenyl, C$_{2-6}$ alkynyl, C$_{3-6}$ cycloalkyl, C$_{3-6}$ cycloalkenyl, 3-6 membered heterocycloalkyl, 3-6 membered heterocycloalkenyl, phenyl, naphthyl, C$_{7-11}$ aralkyl, and 5-10 membered heteroaryl, wherein each of the C$_{1-6}$ alkyl, C$_{2-6}$ alkenyl, C$_{2-6}$ alkynyl, C$_{3-8}$ cycloalkyl, C$_{3-8}$ cycloalkenyl, 3-8 membered heterocycloalkyl, 3-8 membered heterocycloalkenyl, C$_{6-10}$ aryl, C$_{7-11}$ aralkyl and 5-10 membered heteroaryl groups is optionally substituted with 1, 2, 3, 4 or 5 R$^f$ substituents.

25. The compound of claim 1, or a pharmaceutically acceptable salt thereof, wherein R$^2$ is phenyl optionally substituted with 1, 2, 3, 4 or 5 substituents selected from halogen, CN, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

26. The compound of claim 1, or a pharmaceutically acceptable salt thereof, wherein R$^2$ is 5-10 membered heteroaryl optionally substituted with 1, 2, 3, 4 or 5 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

27. The compound of claim 26, or a pharmaceutically acceptable salt thereof, wherein R$^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with 1, 2, 3 or 4 substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

28. The compound of claim 27, or a pharmaceutically acceptable salt thereof, wherein R$^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with a substituent selected from (CH$_2$)$_n$C(O)OR$^a$ and (CH$_2$)$_n$C(O)NR$^b$R$^c$; and optionally substituted with 1, 2 or 3 additional substituents selected from halogen, CN, oxo, (CH$_2$)$_n$OR$^a$, (CH$_2$)$_n$OC(O)R$^a$, (CH$_2$)$_n$OC(O)OR$^a$, (CH$_2$)$_n$OC(O)NR$^b$R$^c$, (CH$_2$)$_n$NR$^b$R$^c$, (CH$_2$)$_n$NR$^d$C(O)R$^a$, (CH$_2$)$_n$NR$^d$C(O)OR$^a$, (CH$_2$)$_n$NR$^d$C(O)NR$^b$R$^c$, (CH$_2$)$_n$NR$^d$C(O)C(O)NR$^b$R$^c$, (CH$_2$)$_n$NR$^d$C(S)R$^a$, (CH$_2$)$_n$NR$^d$C(S)OR$^a$, (CH$_2$)$_n$NR$^d$C(S)NR$^b$R$^c$, (CH$_2$)$_n$NR$^d$C(NR$^e$)NR$^b$R$^c$, (CH$_2$)$_n$NR$^d$S(O)R$^a$, (CH$_2$)$_n$NR$^d$SO$_2$R$^a$, (CH$_2$)$_n$NR$^d$SO$_2$NR$^b$R$^c$, (CH$_2$)$_n$C(O)R$^a$, (CH$_2$)$_n$C(O)OR$^a$, (CH$_2$)$_n$C(O)NR$^b$R$^c$, (CH$_2$)$_n$C(S)R$^a$, (CH$_2$)$_n$C(S)OR$^a$, (CH$_2$)$_n$C(S)NR$^b$R$^c$, (CH$_2$)$_n$C(NR$^e$)NR$^b$R$^c$, (CH$_2$)$_n$SR$^a$, (CH$_2$)$_n$S(O)R$^a$, (CH$_2$)$_n$SO$_2$R$^a$, (CH$_2$)$_n$SO$_2$NR$^b$R$^c$, C$_{1-6}$ alkyl, C$_{1-6}$ haloalkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl, wherein each of the C$_{1-6}$ alkyl, C$_{2-6}$ alkenyl, C$_{2-6}$ alkynyl, (CH$_2$)$_n$C$_{3-8}$ cycloalkyl, (CH$_2$)$_n$3-8 membered heterocycloalkyl, (CH$_2$)$_n$phenyl, (CH$_2$)$_n$naphthyl and (CH$_2$)$_n$5-10 membered heteroaryl groups is optionally substituted with 1, 2, 3, 4 or 5 R$^f$ substituents.

29. The compound of claim 28, or a pharmaceutically acceptable salt thereof, wherein R$^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with (CH$_2$)$_n$C(O)NR$^b$R$^c$.

30. The compound of claim 27, or a pharmaceutically acceptable salt thereof, wherein R$^2$ is selected from pyridyl, pyrimidyl, pyrazyl, pyridazyl, triazyl, furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is $C_{1-6}$ alkyl or 3-8 membered heterocycloalkyl, each optionally substituted with 1, 2 or 3 additional substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_nNR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

31. The compound of claim 30, or a pharmaceutically acceptable salt thereof, wherein $R^2$ is selected from furanyl, pyrrolyl, thiophenyl, thiazolyl, isothiazolyl, thiadiazolyl, oxazolyl, isoxazolyl, oxadiazolyl, imidazolyl, triazolyl and tetrazolyl, each optionally substituted with $(CH_2)_nNR^dC(O)R^a$, wherein $R^a$ is selected from $C_{1-6}$ alkyl, $C_{1-6}$ alkyl-OH and $C_{1-6}$ alkyl-NH$_2$, each optionally substituted with 1, 2 or 3 additional substituents selected from halogen, CN, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl.

32. The compound of claim 26, or a pharmaceutically acceptable salt thereof, wherein $R^2$ is selected from indolyl, indazolyl, benzimidazolyl, benzoxazolyl and benzoisoxazolyl, each optionally substituted with 1, 2, 3 or 4 substituents selected from halogen, CN, oxo, $(CH_2)_nOR^a$, $(CH_2)_nOC(O)R^a$, $(CH_2)_nOC(O)OR^a$, $(CH_2)_nOC(O)NR^bR^c$, $(CH_2)_nNR^bR^c$, $(CH_2)_nNR^dC(O)R^a$, $(CH_2)_nNR^dC(O)OR^a$, $(CH_2)_nNR^dC(O)NR^bR^c$, $(CH_2)_nNR^dC(O)C(O)NR^bR^c$, $(CH_2)_nNR^dC(S)R^a$, $(CH_2)_nNR^dC(S)OR^a$, $(CH_2)_nNR^dC(S)NR^bR^c$, $(CH_2)_n{''}NR^dC(NR^e)NR^bR^c$, $(CH_2)_nNR^dS(O)R^a$, $(CH_2)_nNR^dSO_2R^a$, $(CH_2)_nNR^dSO_2NR^bR^c$, $(CH_2)_nC(O)R^a$, $(CH_2)_nC(O)OR^a$, $(CH_2)_nC(O)NR^bR^c$, $(CH_2)_nC(S)R^a$, $(CH_2)_nC(S)OR^a$, $(CH_2)_nC(S)NR^bR^c$, $(CH_2)_nC(NR^e)NR^bR^c$, $(CH_2)_nSR^a$, $(CH_2)_nS(O)R^a$, $(CH_2)_nSO_2R^a$, $(CH_2)_nSO_2NR^bR^c$, $C_{1-6}$ alkyl, $C_{1-6}$ haloalkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl, wherein each of the $C_{1-6}$ alkyl, $C_{2-6}$ alkenyl, $C_{2-6}$ alkynyl, $(CH_2)_nC_{3-8}$ cycloalkyl, $(CH_2)_n$3-8 membered heterocycloalkyl, $(CH_2)_n$phenyl, $(CH_2)_n$naphthyl and $(CH_2)_n$5-10 membered heteroaryl groups is optionally substituted with 1, 2, 3, 4 or 5 $R^f$ substituents.

33. The compound of claim 1, or a pharmaceutically acceptable salt thereof, wherein $R^1$, at each occurrence, is selected from hydrogen, halogen, CN, $CF_3$ and methyl.

34. The compound of claim 33, or a pharmaceutically acceptable salt thereof, wherein $R^1$, at each occurrence, is hydrogen.

35. The compound of claim 1, or a pharmaceutically acceptable salt thereof, wherein $R^4$ is hydrogen.

36. A pharmaceutical composition comprising a compound of claim 1, or a pharmaceutically acceptable salt thereof, and one or more pharmaceutical carriers or excipients.

37. The pharmaceutical composition of claim 36, wherein the pharmaceutical composition is formulated for oral, sublingual, subcutaneous, parenteral, intravenous, intranasal, topical, transdermal, intraperitoneal, intramuscular, intrapulmonary, vaginal, rectal, or intraocular administration.

38. The pharmaceutical composition of claim 37, wherein the pharmaceutical composition is formulated for oral administration.

39. A method for the treatment of a neuromuscular disorder comprising administering to a patient in need thereof a therapeutically effective amount of a compound of claim 1, or a pharmaceutically acceptable salt thereof.

40. The method of claim 39, wherein the neuromuscular disorder is selected from Amyotrophic Lateral Sclerosis (ALS), Spinal Muscular Atrophy (SMA) and myasthenia gravis.

41. A method for the treatment of a disease selected from peripheral vascular disease and peripheral arterial disease, comprising administering to a patient in need thereof a therapeutically effective amount of a compound of claim 1, or a pharmaceutically acceptable salt thereof.

42. The compound of claim 1 selected from:
4-fluoro-3-(3-{[1-(4-fluorophenyl)-isopropyl]amino}(1,2,4-triazin-6-yl))benzamide;
3-[3-({1-[6-(difluoromethoxy)(2-pyridyl)]-isopropyl}amino)(1,2,4-triazin-6-yl)]-4-fluorobenzamide;
4-fluoro-3-(3-{[1-(3-fluoro(2-pyridyl))-isopropyl]amino}(1,2,4-triazin-6-yl))benzamide;
1-(3-{[1-(3-fluoro(2-pyridyl))-isopropyl]amino}-1,2,4-triazin-6-yl)pyrazole-4-carboxamide;
1-[3-({1-[6-(difluoromethoxy)(2-pyridyl)]-isopropyl}amino)-1,2,4-triazin-6-yl]pyrazole-4-carboxamide;
2-[3-({1-[6-(difluoromethoxy)(2-pyridyl)]-isopropyl}amino)-1,2,4-triazin-6-yl]-1,3-thiazole-5-carboxamide;
3-(3-{[1-(3-fluoro(2-pyridyl))-isopropyl]amino}-1,2,4-triazin-6-yl)benzamide;
4-fluoro-3-(3-{[1-methyl-1-(6-methyl(2-pyridyl))ethyl]amino}(1,2,4-triazin-6-yl))benzamide;
3-(3-{[1-(3-chloro(2-pyridyl))-isopropyl]amino}-1,2,4-triazin-6-yl)benzamide;
3-(3-{[1-(3-chloro(2-pyridyl))-isopropyl]amino}(1,2,4-triazin-6-yl))-4-fluorobenzamide;
4-fluoro-3-(3-{[1-(5-fluoro-6-methyl(2-pyridyl))-isopropyl]amino}(1,2,4-triazin-6-yl))benzamide;
4-fluoro-3-(3-{[1-(3-fluoro(2-pyridyl))-isopropyl]amino}(1,2,4-triazin-6-yl))benzoic acid;
[6-(3-amino-6-fluorophenyl)(1,2,4-triazin-3-yl)][1-(3-fluoro(2-pyridyl))-isopropyl]amine;
[4-fluoro-3-(3-{[1-(3-fluoro(2-pyridyl))-isopropyl]amino}(1,2,4-triazin-6-yl))phenyl](methylsulfonyl)amine;
5-(3-{[1-(3-fluoro(2-pyridyl))-isopropyl]amino}-1,2,4-triazin-6-yl)-1H-2-hydroindazol-3-one;
2-fluoro-5-(3-{[1-(3-fluoro(2-pyridyl))-isopropyl]amino}(1,2,4-triazin-6-yl))benzoic acid;
2-fluoro-5-(3-{[1-(3-fluoro(2-pyridyl))-isopropyl]amino}(1,2,4-triazin-6-yl))benzamide;

N-((2S)-2,3-dihydroxypropyl)[4-fluoro-3-(3-{[1-(3-fluoro(2-pyridyl))-isopropyl]amino}(1,2,4-triazin-6-yl))phenyl]carboxamide;
N-[4-fluoro-3-(3-{[1-(3-fluoro(2-pyridyl))-isopropyl]amino}(1,2,4-triazin-6-yl))phenyl]methoxycarboxamide;
amino[4-fluoro-3-(3-{[1-(3-fluoro(2-pyridyl))-isopropyl]amino}(1,2,4-triazin-6-yl))phenyl]sulfonamide;
3-[3-({1-[6-(difluoromethyl)(2-pyridyl)]-isopropyl}amino)(1,2,4-triazin-6-yl)]-4-fluorobenzamide;
3-[3-({1-[6-(difluoromethyl)(2-pyridyl)]-isopropyl}amino)(1,2,4-triazin-6-yl)]-4-fluorobenzenecarbonitrile;
2-[3-(3-{[1-(3-fluoro(2-pyridyl))-isopropyl]amino}-1,2,4-triazin-6-yl)phenyl]acetamide;
methyl 3-fluoro-4-(3-{[1-(3-fluoro(2-pyridyl))-isopropyl]amino}(1,2,4-triazin-6-yl))benzoate;
3-fluoro-4-(3-{[1-(3-fluoro(2-pyridyl))-isopropyl]amino}(1,2,4-triazin-6-yl))benzamide;
3-fluoro-4-(3-{[1-(3-fluoro(2-pyridyl))-isopropyl]amino}(1,2,4-triazin-6-yl))benzoic acid;
[4-fluoro-3-(3-{[1-(3-fluoro(2-pyridyl))-isopropyl]amino}(1,2,4-triazin-6-yl))phenyl]methan-1-ol;
{6-[5-(aminomethyl)-2-fluorophenyl](1,2,4-triazin-3-yl)}[1-(3-fluoro(2-pyridyl))-isopropyl]amine;
N-{[4-fluoro-3-(3-{[1-(3-fluoro(2-pyridyl))-isopropyl]amino}(1,2,4-triazin-6-yl))phenyl]methyl}acetamide;
4-fluoro-3-(3-{[1-(3-fluoro-6-methyl(2-pyridyl))-isopropyl]amino}(1,2,4-triazin-6-yl))benzamide;
2-amino-N-{[4-fluoro-3-(3-{[1-(3-fluoro(2-pyridyl))-isopropyl]amino}(1,2,4-triazin-6-yl))phenyl]methyl}acetamide;
[1-(3-fluoro(2-pyridyl))-isopropyl](6-(1,3-thiazol-2-yl)(1,2,4-triazin-3-yl))amine;
4-fluoro-3-[3-({1-methyl-1-[3-(methylsulfonyl)phenyl]ethyl}amino)(1,2,4-triazin-6-yl)]benzamide;
methyl 4-fluoro-3-[3-({1-methyl-1-[3-(methylsulfonyl)phenyl]ethyl}amino)(1,2,4-triazin-6-yl)]benzoate;
[2-(3-{[1-(3-chloro(2-pyridyl))-isopropyl]amino}-1,2,4-triazin-6-yl)-1,3-thiazol-5-yl]methan-1-ol;
2-[2-(3-{[1-(3-fluoro(2-pyridyl))-isopropyl]amino}-1,2,4-triazin-6-yl)-1,3-thiazol-5-yl]acetamide;
3-[3-({1-[3-(difluoromethyl)(2-pyridyl)]-isopropyl}amino)(1,2,4-triazin-6-yl)]-4-fluorobenzenecarbonitrile;
3-[3-({1-[3-(difluoromethyl)(2-pyridyl)]-isopropyl}amino)(1,2,4-triazin-6-yl)]-4-fluorobenzamide;
{6-[5-(aminomethyl)(1,3-thiazol-2-yl)](1,2,4-triazin-3-yl)}[1-(3-chloro(2-pyridyl))-isopropyl]amine;
N-{[2-(3-{[1-(3-chloro(2-pyridyl))-isopropyl]amino}-1,2,4-triazin-6-yl)-1,3-thiazol-5-yl]methyl}acetamide;
1-(3-{[1-(3-chloro(2-pyridyl))-isopropyl]amino}-1,2,4-triazin-6-yl)pyrazole-4-carboxamide;
or a pharmaceutically acceptable salt thereof.

43. The compound of claim 1 selected from:
3-(3-{[2-(4-fluorophenyl)-2-methylpropyl]amino}-1,2,4-triazin-6-yl)benzamide;
[6-(3-amino(1H-indazol-5-yl))(1,2,4-triazin-3-yl)][2-(4-fluorophenyl)-2-methylpropyl]amine;
3-(6-{[2-(4-fluorophenyl)-2-methylpropyl]amino}-1,2,4-triazin-3-yl)benzamide;
2-fluoro-5-(3-{[2-(4-fluorophenyl)-2-methylpropyl]amino}(1,2,4-triazin-6-yl))benzamide;
(6-(1H-indazol-5-yl)(1,2,4-triazin-3-yl))[2-(3-fluoro(2-pyridyl))-2-methylpropyl]amine;
1-(3-{[2-(4-fluorophenyl)-2-methylpropyl]amino}-1,2,4-triazin-6-yl)pyrazole-4-carboxamide;
methyl 3-(3-{[2-(3-chloro(2-pyridyl))-2-methylpropyl]amino}(1,2,4-triazin-6-yl))-4-fluorobenzoate;
3-(3-{[2-(3-chloro(2-pyridyl))-2-methylpropyl]amino}(1,2,4-triazin-6-yl))-4-fluorobenzamide;
3-(3-{[2-(3-chloro(2-pyridyl))-2-methylpropyl]amino}(1,2,4-triazin-6-yl))-4-fluorobenzoic acid;
or a pharmaceutically acceptable salt thereof.

44. The compound of claim 1 selected from:
4-fluoro-3-(3-{[[(fluoro(2-pyridyl))cyclobutyl]amino}(1,2,4-triazin-6-yl))benzamide;
4-fluoro-3-(3-{[(4-fluorophenyl)cyclobutyl]amino}(1,2,4-triazin-6-yl))benzamide;
3-[3-({[6-(difluoromethoxy)(2-pyridyl)]cyclobutyl}amino)(1,2,4-triazin-6-yl)]-4-fluorobenzamide;
{[6-(difluoromethoxy)(2-pyridyl)]cyclobutyl}[6-(5-bromo-2-fluorophenyl)(1,2,4-triazin-3-yl)]amine;
1-(3-{[(3-fluoro-2-pyridyl)cyclobutyl]amino}-1,2,4-triazin-6-yl)pyrazole-4-carboxamide;
or a pharmaceutically acceptable salt thereof.

45. The compound of claim 1 selected from:
3-[6-({[(4-fluorophenyl)cyclobutyl]methyl}amino)-1,2,4-triazin-3-yl]benzamide;
2-fluoro-5-[3-({[(3-fluoro(2-pyridyl))cyclobutyl]methyl}amino)(1,2,4-triazin-6-yl)]benzenecarbonitrile;
(6-(1H-indazol-5-yl)(1,2,4-triazin-3-yl)){[(3-fluoro(2-pyridyl))cyclobutyl]methyl}amine;
[6-(3-amino(1H-indazol-5-yl))(1,2,4-triazin-3-yl)]{[(3-fluoro(2-pyridyl))cyclobutyl]methyl}amine;
[6-(4-bromophenyl)(1,2,4-triazin-3-yl)]{[(3-fluoro(2-pyridyl))cyclobutyl]methyl}amine;
[6-(4-aminophenyl)(1,2,4-triazin-3-yl)]{[(3-fluoro(2-pyridyl))cyclobutyl]methyl}amine;
1-[3-({[(3-fluoro-2-pyridyl)cyclobutyl]methyl}amino)-1,2,4-triazin-6-yl]pyrazole-4-carboxamide;
3-(3-{[(2-pyridylcyclobutyl)methyl]amino}-1,2,4-triazin-6-yl)benzenecarbonitrile;
3-(3-{[(2-pyridylcyclobutyl)methyl]amino}-1,2,4-triazin-6-yl)benzamide;
{2-[3-({[3-fluoro-1-(3-fluoro(2-pyridyl))cyclobutyl]methyl}amino)-1,2,4-triazin-6-yl]-1,3-thiazol-5-yl}methan-1-ol;
3-[3-({[3-fluoro-1-(3-fluoro(2-pyridyl))cyclobutyl]methyl}amino)-1,2,4-triazin-6-yl]benzamide;
{6-[5-(aminomethyl)(1,3-thiazol-2-yl)](1,2,4-triazin-3-yl)}{[3-fluoro-1-(3-fluoro(2-pyridyl))cyclobutyl]methyl}amine;
N-({2-[3-({[3-fluoro-1-(3-fluoro(2-pyridyl))cyclobutyl]methyl}amino)-1,2,4-triazin-6-yl]-1,3-thiazol-5-yl}methyl)acetamide;
methyl 3-[3-({[(3-chloro(2-pyridyl))cyclobutyl]methyl}amino)(1,2,4-triazin-6-yl)]-4-fluorobenzoate;
methyl 4-fluoro-3-(3-{[(2-pyridylcyclobutyl)methyl]amino}(1,2,4-triazin-6-yl))benzoate;
3-[3-({[(3-chloro(2-pyridyl))cyclobutyl]methyl}amino)(1,2,4-triazin-6-yl)]-4-fluorobenzamide;
4-fluoro-3-(3-{[(2-pyridylcyclobutyl)methyl]amino}(1,2,4-triazin-6-yl))benzamide;
3-[3-({[(3-chloro(2-pyridyl))cyclobutyl]methyl}amino)(1,2,4-triazin-6-yl)]-4-fluorobenzoic acid;
4-fluoro-3-[3-({[3-fluoro-1-(3-fluoro(2-pyridyl))cyclobutyl]methyl}amino)(1,2,4-triazin-6-yl)]benzamide;
3-[3-({[1-(3-chloro(2-pyridyl))-3-fluorocyclobutyl]methyl}amino)-1,2,4-triazin-6-yl]benzamide;

3-[3-({[1-(3-chloro(2-pyridyl))-3-fluorocyclobutyl]methyl}amino)(1,2,4-triazin-6-yl)]-4-fluorobenzamide;

3-[3-({[1-(3-chloro(2-pyridyl))-3-fluorocyclobutyl]methyl}amino)-1,2,4-triazin-6-yl]benzenecarbonitrile;

3-[3-({[(3-fluoro-2-pyridyl)cyclobutyl]methyl}amino)-1,2,4-triazin-6-yl]benzamide;

2-{2-[3-({[3-fluoro-1-(3-fluoro(2-pyridyl))cyclobutyl]methyl}amino)-1,2,4-triazin-6-yl]-1,3-thiazol-5-yl}acetamide;

2-{2-[3-({[(3-fluoro-2-pyridyl)cyclobutyl]methyl}amino)-1,2,4-triazin-6-yl]-1,3-thiazol-5-yl}acetamide;

{2-[3-({[(3-fluoro-2-pyridyl)cyclobutyl]methyl}amino)-1,2,4-triazin-6-yl]-1,3-thiazol-5-yl}methan-1-ol;

4-fluoro-3-[3-({[(3-fluoro(2-pyridyl))cyclobutyl]methyl}amino)(1,2,4-triazin-6-yl)]benzoic acid;

{4-fluoro-3-[3-({[(3-fluoro(2-pyridyl))cyclobutyl]methyl}amino)(1,2,4-triazin-6-yl)]phenyl}-N-methylcarboxamide;

4-fluoro-3-[3-({[(3-fluoro(2-pyridyl))cyclobutyl]methyl}amino)(1,2,4-triazin-6-yl)]benzamide;

{3-[3-({[1-(3-chloro(2-pyridyl))-3-fluorocyclobutyl]methyl}amino)(1,2,4-triazin-6-yl)]phenyl}-N-methylcarboxamide;

{3-[3-({[1-(3-chloro(2-pyridyl))-3-fluorocyclobutyl]methyl}amino)(1,2,4-triazin-6-yl)]-4-fluorophenyl}-N-methylcarboxamide;

3-[3-({[1-(3-chloro(2-pyridyl))-3,3-difluorocyclobutyl]methyl}amino)(1,2,4-triazin-6-yl)]-4-fluorobenzamide;

{3-[3-({[1-(3-chloro(2-pyridyl))-3,3-difluorocyclobutyl]methyl}amino)(1,2,4-triazin-6-yl)]-4-fluorophenyl}-N-methylcarboxamide;

{4-fluoro-3-[3-({[3-fluoro-1-(3-fluoro(2-pyridyl))cyclobutyl]methyl}amino)(1,2,4-triazin-6-yl)]phenyl}-N-methylcarboxamide;

{3-[3-({[3-fluoro-1-(3-fluoro(2-pyridyl))cyclobutyl]methyl}amino)(1,2,4-triazin-6-yl)]-4-hydroxyphenyl}-N-methylcarboxamide;

3-[3-({[3-fluoro-1-(3-fluoro(2-pyridyl))cyclobutyl]methyl}amino)(1,2,4-triazin-6-yl)]-4-hydroxybenzamide;

{3-[3-({[3-fluoro-1-(3-fluoro(2-pyridyl))cyclobutyl]methyl}amino)(1,2,4-triazin-6-yl)]phenyl}-N-methylcarboxamide;

4-fluoro-3-[3-({[3-fluoro-1-(3-fluoro(2-pyridyl))cyclobutyl]methyl}amino)(1,2,4-triazin-6-yl)]-2-hydroxybenzamide;

or a pharmaceutically acceptable salt thereof.

\* \* \* \* \*